US006433137B1

(12) United States Patent
Johnson et al.

(10) Patent No.: US 6,433,137 B1
(45) Date of Patent: Aug. 13, 2002

(54) **TUP1 SEQUENCES FROM *CANDIDA ALBICANS* AND METHODS FOR SCREENING AGENTS FOR INHIBITING VIRULENCE IN *CANDIDA ALBICANS* USING TUP1**

(75) Inventors: Alexander D. Johnson; Burkhard Braun, both of San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/108,857

(22) Filed: Jul. 1, 1998

Related U.S. Application Data

(60) Provisional application No. 60/051,552, filed on Jul. 2, 1997.

(51) Int. Cl.⁷ .................................................. C07K 1/00
(52) U.S. Cl. ........................ 530/350; 530/350; 530/300; 530/387; 530/371; 435/69.1; 435/254.2; 435/483; 435/6; 435/252.3; 435/320.1; 435/325; 536/23.2
(58) Field of Search ............................. 435/69.1, 254.2, 435/483, 6, 252.3, 320.1, 325; 530/300, 387, 350, 371; 536/23.2

(56) References Cited

U.S. PATENT DOCUMENTS

| | | | |
|---|---|---|---|
| 4,683,195 A | 7/1987 | Mullis et al. | 435/6 |
| 4,683,202 A | 7/1987 | Mullis | 435/91 |
| 4,754,065 A | 6/1988 | Levenson et al. | 562/564 |
| 4,800,159 A | 1/1989 | Mullis et al. | 435/172.3 |

OTHER PUBLICATIONS

Cannon et al., "Oral Candida: Clearance, colonization, or candidiasis?" *J. Dental Res.* 74(5):1152–1161 (1995).
Current Protocols in Molecular Biology (Ausubel et al., eds.) Suppl. 30, Section 7.7.18–19, Table 7.7.1 (1987).
de Bernardis et al., "Filamentous growth and elevated vaginopathic potential of a nongermanative variant of *Candida albicans* expressing low virulence in systemic infection" *Infect. Immun.* 61(4):1500–1508 (1993).
Dudley, M.N., "Introduction to the Symposium" *Pharmacotherapy* 10(6):133S (1990).
Dupont, P.F., "*Candida albicans*, the opportunist" *J. Am. Podiatric Med. Assn.* 85(2):104–115 (1995).
Edmondson et al., "Repression domain of the yeast global repressor Tup1 interacts directly with histones H3 and H4" *Genes Dev.* 10(10):1247–1259 (1996).
Fidel, Jr., P.L. .and Sobel, J.D. "Immunopathogenesis of recurrent vulvovaginal candidiasis" *Clin. Micro. Rev.* 9(3):335–348 (1996).
Fidel et al., "A murine model of *Candida glabrata* vaginitis" *J. Infec. Disease* 173(2):425–431 (1996).
Fidel et al., "Candida–specific cell–mediated immunity is demonstrable in mice with experimental vaginal candidiasis" *Infect. Immun.* 61(5):1990–1995 (1993).

Fonzi, W.A. and Irwin, M.Y., "Isogenic strain construction and gene mapping in *Candida albicans*" *Genetics* 134(3):717–728 (1993).
Fox et al., "Fluconazole resistant Candida in AIDS" *J. Infect.* 22(2):201–204 (1991).
Gietz et al., "Studies on the transformation of intact yeast cells by the LiAc/SS–DNA/PEG procedure", *Yeast* 11(4):355–360 (1995).
Gillum et al., "Isolation of the *Candida albicans* gene of orotidine–5'–phosphate decarboxylase by complementation of *S. cerevisiae* ura3 and *E. coli* pyrF mutations" *Mol. Gen. Genet.* 198:179–182 (1984).
Gow, N.A.R. and Gooday, G.W., "A model for the germ tube formation and mycelial growth form of *Candida albicans*" *Sabouraudia: J. Med. Vet. Mycol.* 22:137–143 (1984).
Hartley et al., "A deduced gene product from the Drosophila neurogenic locus, Enhancer of split, shows homology to mammalian G–protein βsubunit" *Cell* 55:785–795 (1988).
Herlyn et al., "Anti–idiotypic antibodies bear the internal image of a human tumor antigen" *Science* 232:100–102 (1986).
Hill et al., "DMSO enhanced whole cell yeast transformation" *Nucleic Acids Res.* 19(20):5791 (1991).
Horn et al., "Cancer gene therapy using plasmid DNA: Purification of DNA for human trials" *Human Gene Ther.* 6(5):565–573 (1995).
Keleher et al., "Ssn6–Tup1 is a general repressor of transcription in yeast" *Cell* 68:709–719 (1992).
Kerridge, D., "Fungal dimorphism: A sideways look" in: Dimorphic Fungi in Biology and Medicine, Vanden Bossche et al., eds., Plenum Press, New York, pp. 3–10 (1993).
Komachi et al., "The WD repeats of Tup1 interact with the homeo domain protein α2" *Genes Dev.* 8:2857–2867 (1994).
Lemontt et al., "Pleiotropic mutations at the Tup1 locus that affect the expression of mating–type–dependent functions in *Saccharomyces cerevisiae*" *Genetics* 94:899–920 (1980).
Llevadot et al., "Genomic organization of TUPLE1/HIRA: A gene implicated in DiGeorge syndrome" *Mammalian Genome* 7:911–914 (1996).

(List continued on next page.)

Primary Examiner—Karen Cochrane Carlson
Assistant Examiner—Hope A. Robinson
(74) Attorney, Agent, or Firm—Morrison & Foerster LLP

(57) ABSTRACT

The present invention provides TUP1 polynucleotides, including TUP1 polynucleotides encoding Tup1, and Tup1 polypeptides, from *Candida albicans*. Disruption of TUP1 function in *C. albicans* is associated with filamentous formation as well as low infectivity. These TUP1 polynucleotide and Tup1 polypeptide sequences (and anti-Tup1 antibodies derived from Tup1 polypeptides) may be used in methods of detecting *C. albicans* sequences in a biological sample. Further, the invention provides methods for screening agents which may control *C. albicans* virulence and compositions comprising these agents. The invention also provides methods of obtaining gene(s) and/or gene product (s) which are involved in a TUP1 pathway, as well as methods of controlling *C. albicans* virulence by comprising TUP1 function.

33 Claims, 10 Drawing Sheets-

OTHER PUBLICATIONS

Marquis et al., "Strain–dependent differences in susceptibility in mice to experimental candidosis" *J. Infect. Dis.* 154(5):906–909 (1986).

Merrifield, R.B., "Solid phase peptide synthesis" *J. Am. Chem. Soc.* 85:2149–2154 (1963).

Odds, F.C., "Candida species and virulence" *ASM News* 60(6):313–318 (1994).

Odds, F.C., "Morphogenesis in *Candida albicans*" *Crit. Rev. Microbiol.* 12(1):45–93 (1985).

Odds, F.C., "Pathogenesis of Candida infections" *J. Am. Acad. Dermatol.* 31:S2–S5 (1994).

Ohama et al., "Non–universal decoding of the leucine colon CUG in several Candida species" *Nucl. Acids Res.* 21(17):4039–4045 (1993).

Oi, V.T. and Morrison, S.L., "Chimeric antibodies" *BioTechniques* 4(3):214–221 (1986).

Paya, C.V., "Fungal infections in solid–organ transplantation" *Clin. Infect. Dis.* 16:677–688 (1993).

Posnett et al., "A novel method for producing anti–peptide antibodies" *J. Biol. Chem.* 263(4):1719–1725 (1988).

Redd et al., "A complex composed of Tup1 and Ssn6 represses transcription in Vitro" *J. Biol. Chem.* 272(17):11193–11197 (1997).

Rubin, R.H., "Fungal and bacterial infections in the immunocompromised host" *Eur. J. Clin. Micro. Infect. Dis.* 12(Suppl. 1):S42–S48 (1993).

Scherer, S. and Magee, P.T., "Genetics of *Candida albicans*" *Microbiological Rev.* 54(3):226–241 (1990).

Sheperd, M.G., "Pathogenicity of morphological and auxotropic mutants of *Candida albicans* in experimental infections" *Infect. Immunity* 50(2):541–544 (1985).

Simon et al., "Diversity of G proteins in signal transduction" *Science* 252:802–808 (1991).

Spira et al., "The identification of monoclonal class switch variants by sib selection and an ELISA assay" *J. Immunol. Meth.* 74:307–315 (1984).

Steplewski et al., "Isolation and characterization of anti–monosialoganglioside monoclonal antibody 19–9 class–switch variants" *Proc. Natl. Acad. Sci. USA* 82:8653–8657 (1985).

Stitt et al., "The anticoagulation factor protein S and its relative, Gas6, are ligands for the Tyro 3/Ax1 family of receptor tyrosine kinases" *Cell* 80:661–670 (1995).

Tam, J.P., "High–density multiple antigen–peptide system for preparation of antipeptide antibodies" *Meth. Enzymol.* 168:7–15 (1989).

Tzamarias, D. and Struhl, K. "Functional dissection of the yeast Cy8–Tup1 transcriptional co–repressor complex" *Nature* 369:758–761 (1994).

Wahi, M. and Johnson, A.D., "Identification of genes required for α2 repression in *Saccharomyces cerevisiae*" *Genetics* 140:79–90 (1995).

Wall et al., "The structure of the G protein heterodimer $G_{i\alpha 1}\beta_{1\gamma 2}$" *Cell* 83:1047–1058 (1995).

Warren, N.G. and Shadomy, H.J., "Yeasts of medical importance" in Manual of Clinical Microbiology, 5th ed., Chapter 60, pp. 617–629 (1991).

Weinberg, K. and Parkman, R., "Severe combined immunodeficiency due to a specific defect in the production of interleukin–2" *N. Eng. J. Med.* 332(24):1718–1723, 1741–1743 (1990).

Williams, F.E. and Trumbly, R.J. "Characterization of TUP1, a mediator of glucose repression in *Saccharomyces cerevisiae*" *Mol. Cell. Biol.* 10(12):6500–6511 (1990).

Yochem, J. and Byers, B., "Structural comparison of the yeast cell division cycle gene CDC4 and a related pseudogene" *J. Mol. Biol.* 195:233–245 (1987).

Williams et al. Mollecular and Cellular Biology, vol. 10, pp. 6500–6511, Dec. 1990.

Fujita et al., Gene, vol. 89, pp. 93–99, 1990.

Alignments.

Komachi et al. (1997). "Residues in the WD repeats of tup1 required for interaction with α2," *Mol. and Cell. Biol.* 17(10):6023–6028.*

Lo et al. (1997). "Nonfilamentous *C. albicans* mutants are avirulent," *Cell.* 90: 939–949.*

Braun, B.R. and Johnson, A.D., "Control of Filament Formation in *Candida albicans* by the Transcriptional Repressor TUP1" *Science* 277:105109 (Jul. 1997).

* cited by examiner

Blastospores     Pseudohypha

True Hypha

Figure 2A

```
ScTUP1   1  - - M T A S V S N T Q N K L N E L L D A I R Q E F L Q V S Q E A N T Y   33
CaTUP1   1  M S M Y P Q R T Q H Q Q R L T E L L D A I K T E F D Y A S N E A S S F   35

ScTUP1  34  R L Q N Q K D Y D F K M N Q O L A E M Q Q I R N T V Y E L E L T H R K   68
CaTUP1  36  K - K V Q E D Y D S K Y Q O O A A E M Q Q I R Q T V Y D L E L A H R K   69

ScTUP1  69  M K D A Y E A E I K H L K L G L E Q R D H Q I A S L T V Q Q Q Q Q Q Q  103
CaTUP1  70  I K E A Y E E E I L R L K N E L D T R D R Q M K N - G F Q Q Q Q Q Q Q  103

ScTUP1 104  Q Q Q Q V Q Q H L Q Q Q Q Q Q Q L A A A S A S V P V A Q Q P P A T T S A  138
CaTUP1 104  Q Q Q Q Q Q Q - - Q Q Q Q Q Q Q I V A - - - - - - - - - - P P A P P A  126

ScTUP1 139  T A T P A A N T T T G S P S A F P V Q A S R P N L V G S Q L P T T L  173
CaTUP1 127  P P T - - - - - - - - - - - - - - - - - - - - - - - - - - - P V T S L  134

ScTUP1 174  P V V S S N A Q Q Q L P Q Q Q L Q Q Q Q L Q Q Q Q P P P Q V S V A P L  208
CaTUP1 135  S V I - - - - - - - - - - - - - - - - - - - - - - - - - - - - - - - -  137

ScTUP1 209  S N T A I N G S P T S K E T T T L P S V K A P E S T L K E T E P E N N  243
CaTUP1 138  - - - - - - - - - - - - - - - - - - - - - - - - - - - - - - - - - -  137

ScTUP1 244  N T S K I N D T G S A T T A T T T T A T E T E I K P K E E D A T P A S  278
CaTUP1 138  - - - - - - - - - - - - - - - - - - - - - - - - - - - - - - - - - -  137

ScTUP1 279  L H Q D H Y L V P Y N Q R A N H S K P I P P F L L D L D S Q S V P D A  313
CaTUP1 138  - D K S Q Y I V N P T Q R A N H V K E I P P F L Q D L D I A K A N P E  171

ScTUP1 314  L K K Q T N D Y Y I L Y N P A L P R E I D V E L H K S L D H T S V V C  348
CaTUP1 172  F K K Q H L E Y Y V L Y N P A F S K D L D I D M V H S L D H S S V V C  206

ScTUP1 349  C V K F S N D G E Y L A T G C N K T T Q V Y R V S D G S L V A R L S D  383
CaTUP1 207  C V R F S R D G K F I A T G C N K T T Q V F N V T T G E L V A K L I D  241

ScTUP1 384  D S A A N N H R N S I T E N N T T T S T D N N T M T T T T T T T I T T  418
CaTUP1 242  E S S N E N - - - - - K D D N T T - - - - - - - - - - - - - - - - - -  253

ScTUP1 419  T A M T S A A E L A K D V E N L N T S S S P S S D L Y I R S V C F S P  453
CaTUP1 254  - - - - - - - - - - - - - - - - - - - - A S G D L Y I R S V C F S P  267

ScTUP1 454  D G K F L A T G A E D R L I R I W D I E N R K I V M I L Q G H E Q D I  488
CaTUP1 268  D G K L L A T G A E D K L I R I W D L S T K R I I K I L R G H E Q D I  302

ScTUP1 489  Y S L D Y F P S G D K L V S G S G D R T V R I W D L R T G Q C S L T L  523
CaTUP1 303  Y S L D F F P D G D R L V S G S G D R S V R I W D L R T S Q C S L T L  337

ScTUP1 524  S I E D G V T T V A V S P G D G K Y I A A G S L D R A V R V W D S E T  558
CaTUP1 338  S I E D G V T T V A V S P - D G K L I A A G S L D R T V R V W D S T T  371

ScTUP1 559  G F L V E R L D S E N E S G T G H K D S V Y S V V F T R D G Q S V V S  593
CaTUP1 372  G F L V E R L D S G N E N G N G H E D S V Y S V A F S N N G E Q I A S  406

ScTUP1 594  G S L D R S V K L W N L Q N A N N K S D S K T P N S G T C E V T Y I G  628
CaTUP1 407  G S L D R T V K L W H L E - - - G K S D K K - - - - S T C E V T Y I G  434

ScTUP1 629  H K D F V L S V A T T Q N D E Y I L S G S K D R G V L F W D K K S G N  663
CaTUP1 435  H K D F V L S V C C T P D N E Y I L S G S K D R G V I F W D Q A S G N  469

ScTUP1 664  P L L M L Q G H R N S V I S V A V A N G S S L G P E Y N V F A T G S G  698
CaTUP1 470  P L L M L Q G H R N S V I S V A V S L N S K - G T E - G I F A T G S G  502

ScTUP1 699  D C K A R I W K Y K K I A P N                                          714
CaTUP1 503  D C K A R I W K W T K K                                                515
```

Figure 6(A)

(xi) SEQUENCE DESCRIPTION: SEQ ID NO.:1:

```
AGATCTTGGG  CAGTGACAGC  TTTACTACTC  TACAGTCAAA  CCCCTCTTCT  CCCCTCTTCT   60
AAACATTGTC  ACTACATTCT  TTATTAATTA  GATTGCAAGT  TACTATGCAA  AAACTATATG  120
TAGAGTAAAT  AAAAACAAAG  AGGGGGCCGA  TAATAGATCA  CTCGATATAC  CCCATGACAG  180
TTGTGTGTCT  AACTACACTC  CTGATTAGAG  TTCGCAAGAA  ATTGTGCTCC  ACACGACTAT  240
TCCAATTCGT  AAAAAATCTG  CCATTTGAAA  AAAGCGCACC  CCCTGTTCAA  AAAAAACCAC  300
GAAAAAACAA  CACAACTTCT  TCCATCCCCA  CCAGCA ATG  TCA ATG TAT  CCC CAA     354
                                          Met         Ser Met Tyr  Pro Gln
                                          1                        5
```

```
CGC ACC CAG CAC CAA CAA CGT TTG ACA GAG TTG TTG GAT GCA ATC AAA  402
Arg Thr Gln His Gln Gln Arg Leu Thr Glu Leu Leu Asp Ala Ile Lys
        10              15                  20

ACT GAA TTC GAC TAC GCC TCA AAC GAA GCA AGC AGT TTC AAA AAG GTC  450
Thr Glu Phe Asp Tyr Ala Ser Asn Glu Ala Ser Ser Phe Lys Lys Val
        25              30                  35

CAA GAA GAT TAT GAC TCA AAG TAC CAA CAA CAA GCT TCC GAA ATG CAA  498
Gln Glu Asp Tyr Asp Ser Lys Tyr Gln Gln Gln Ala Ala Glu Met Gln
        40              45                  50

CAA ATC CGC CAA ACA GTG TAT GAC TTG GAG TTG GCC CAT AGA AAA ATC  546
Gln ile Arg Gln Thr Val Tyr Asp Leu Glu Leu Ala His Arg Lys Ile
55              60                  65                      70

AAA GAG GCA TAC GAG GAA GAG ATA TTG AGG TTA AAG AAC GAG TTG GAC  594
Lys Glu Ala Tyr Glu Glu Glu Ile Leu Arg Leu Lys Asn Glu Leu Asp
            75                  80                  85

ACT AGA GAC AGG CAA ATG AAG AAT GGC TTC CAA CAA CAA CAG CAA CAG  642
Thr Arg Asp Arg Gln Met Lys Asn Gly Phe Gln Gln Gln Gln Gln Gln
        90                  95                  100

CAA CAA CAG CAA CAA CAA CAG CAA CAG CAG CAA CAA CAA CAG ATT GTC  690
Gln Gln Gln Gln Gln Gln Gln Gln Gln Gln Gln Gln Gln Ile Val
        105                 110                 115

GCA CCA CCT GCC GCC CCA CCT GCT CCA CCA ACC CCG GTC ACA TCA TTA  738
Ala Pro Pro Ala Ala Pro Pro Ala Pro Pro Thr Pro Val Thr Ser Leu
        120             125                 130

TCG GTT ATC GAC AAG TCA CAA TAC ATT GTC AAC CCC ACC CAA AGA GCT  786
```

Figure 6(B)

```
    Ser Val Ile Asp Lys Ser Gln Tyr Ile Val Asn Pro Thr Gln Arg Ala
    135             140                 145                 150

AAC CAC GTC AAG GAA ATC CCA CCA TTC TTG CAA GAT TTA GAC ATT GCC  834
    Asn His Val Lys Glu Ile Pro Pro Phe Leu Gln Asp Leu Asp Ile Ala
                    155                 160                 165

AAA GCC AAC CCC GAG TTC AAG AAA CAG CAC CTC GAA TAC TAT GTG TTG  882
    Lys Ala Asn Pro Glu Phe Lys Lys Gln His Leu Glu Tyr Tyr Val Leu
                170                 175                 180

TAC AAC CCA GCG TTC TCC AAA GAC TTG GAT ATT GAC ATG GTC CAC TCC  930
    Tyr Asn Pro Ala Phe Ser Lys Asp Leu Asp Ile Asp Met Val His Ser
            185                 190                 195

TTA GAC CAC TCG TCA GTT GTT TGC TGC GTG AGA TTT TCC AGA GAC GGC  978
    Leu Asp His Ser Ser Val Val Cys Cys Val Arg Phe Ser Arg Asp Gly
        200                 205                 210

AAG TTC ATC GCC ACC GGT TGC AAC AAA ACC ACC CAA GTG TTC AAT GTC 1026
    Lys Phe Ile Ala Thr Gly Cys Asn Lys Thr Thr Gln Val Phe Asn Val
    215                 220                 225                 230

ACC ACC GGA GAG TTG GTC GCC AAA TTG ATT GAC GAG TCC TCC AAC GAA 1074
    Thr Thr Gly Glu Leu Val Ala Lys Leu Ile Asp Glu Ser Ser Asn Glu
                    235                 240                 245

AAC AAA GAC GAC AAC ACC ACC GCC TCA GGC GAC TTG TAC ATC AGA TCT 1122
    Asn Lys Asp Asp Asn Thr Thr Ala Ser Gly Asp Leu Tyr Ile Arg Ser
                250                 255                 260

GTG TGT TTC TCC CCT GAC GGA AAA CTC TTG GCG ACA GGT GCA GAA GAC 1170
    Val Cys Phe Ser Pro Asp Gly Lys Leu Leu Ala Thr Gly Ala Glu Asp
            265                 270                 275

AAG TTG ATT AGA ATC TGG GAT TTG AGC ACA AAG AGA ATT ATC AAA ATC 1218
    Lys Leu Ile Arg Ile Trp Asp Leu Ser Thr Lys Arg Ile Ile Lys Ile
        280                 285                 290

TTG AGG GCC CAC GAA CAA GAC ATT TAC TCG TTA GAC TTT TTC CCT GAT 1266
    Leu Arg Gly His Glu Gln Asp Ile Tyr Ser Leu Asp Phe Phe Pro Asp
    295                 300                 305                 310

GGC GAT AGG TTG GTT TCA GGC TCC GGC GAT AGG TCA GTC AGA ATC TGG 1314
    Gly Asp Arg Leu Val Ser Gly Ser Gly Asp Arg Ser Val Arg Ile Trp
                    315                 320                 325

GAC TTG AGA ACC TCC CAG TGT TCC TTG ACT TTG TCG ATC GAA GAC GGC 1362
    Asp Leu Arg Thr Ser Gln Cys Ser Leu Thr Leu Ser Ile Glu Asp Gly
                330                 335                 340

GTC ACC ACC GTG GCC GTC TCC CCC GAC GGC AAA CTC ATT GCT GCC GGC 1410
```

Figure 6(C)

```
            Val Thr Thr Val Ala Val Ser Pro Asp Gly Lys Leu Ile Ala Ala Gly
                    345                 350                 355

TCA TTA GAT AGA ACC GTT AGA GTG TGG GAC TCA ACT ACC GGG TTC TTG  1458
Ser Leu Asp Arg Thr Val Arg Val Trp Asp Ser Thr Thr Gly Phe Leu
        360                 365                 370

GTC GAA CGC TTA GAC TCC GGC AAC GAA AAC GGC AAT GGC CAC GAA GAT  1506
Val Glu Arg Leu Asp Ser Gly Asn Glu Asn Gly Asn Gly His Glu Asp
375                 380                 385                 390

TCA GTC TAC TCT GTC GCC TTC TCC AAC AAC GGC GAA CAA ATC GCT TCC  1554
Ser Val Tyr Ser Val Ala Phe Ser Asn Asn Gly Glu Gln Ile Ala Ser
                395                 400                 405

GGG TCC TTA GAC AGA ACC GTC AAG TTG TGG CAC TTG GAA GGC AAG TCC  1602
Gly Ser Leu Asp Arg Thr Val Lys Leu Trp His Leu Glu Gly Lys Ser
        410                 415                 420

GAC AAA AAG TCG ACC TGC GAG GTA ACC TAC ATT GGC CAC AAG GAC TTT  1650
Asp Lys Lys Ser Thr Cys Glu Val Thr Tyr Ile Gly His Lys Asp Phe
            425                 430                 435

GTT TTG TCG GTC TGC TGT ACC CCC GAC AAC GAG TAC ATT TTG TCG GGC  1698
Val Leu Ser Val Cys Cys Thr Pro Asp Asn Glu Tyr Ile Leu Ser Gly
        440                 445                 450

TCA AAG GAC CGT GGT GTC ATT TTC TGC GAC CAA TCT TCA GGT AAC CCA  1746
Ser Lys Asp Arg Gly Val Ile Phe Cys Asp Gln Ala Ser Gly Asn Pro
455                 460                 465                 470

TTG TTG ATG TTG CAG GGC CAC CGC AAC TCG GTC ATC GCA GTC GCT GTA  1794
Leu Leu Met Leu Gln Gly His Arg Asn Ser Val Ile Ser Val Ala Val
                475                 480                 485

TCC CTA AAC TCA AAG GGA ACC GAA GGT ATC TTC GCT ACA GGT AGT GGC  1842
Ser Leu Asn Ser Lys Gly Thr Glu Gly Ile Phe Ala Thr Gly Ser Gly
            490                 495                 500

GAT TGT AAA GCC AGA ATT TGG AAA TGG AC  AAA AAA TAAGTGTGTA GTATAT  1894
Asp Cys Lys Ala Arg Ile Trp Lys Trp Thr Lys Lys
        505                 510

ATATATGTGA GAAAAAAAAA CACCACCAAA AAAAAAAATT TTTTTCGTAA CAACCCACCA  1954
TCAATGTACT CTGCTTCTGT CACAGCACCC GTCAACATCG CCGTAAGTAA AAACAAGACC  2014
AACCATCAAT TGAATCTCTA CTAACGTACT TAGACCCTTA AGTATTGGGG GAAACGAGAC  2074
AAGTCGTTGA ACTTGCCCAC CAACTCGTCC ATCTGCGTCA CCTTATCCCA AGACGATTTG  2134
CGAACCCTTG ACAACCGCCT TCTGCATCTG GAATCATTCG AAAAAAGACC AATTGCGGCT  2194
CAATGGCAAA GTCGGGAATC ATTAGATTCC TCCACGTCCC TCAAGCGTGT TTAAGCAGGA  2254
CTTGGAGAAA AGTTTACG                                                2272
```

TUP1 SEQUENCES FROM CANDIDA ALBICANS AND METHODS FOR SCREENING AGENTS FOR INHIBITING VIRULENCE IN CANDIDA ALBICANS USING TUP1

CROSS-REFERENCE TO RELATED APPLICATIONS

This application claims the benefit of U.S. Provisional Application Serial No. 60/051,552, filed Jul. 2, 1997.

STATEMENT OF RIGHTS TO INVENTIONS MADE UNDER FEDERALLY SPONSORED RESEARCH

This invention was made in part during work supported by a grant from the National Institutes of Health (NIH) RO1 GM 37049. The government has certain rights in the invention.

TECHNICAL FIELD

This invention relates to the field of polynucleotides and polypeptides. More specifically, this invention relates to TUP1 polynucleotides from *Candida albicans*, Tup1 polypeptides, and methods using these polynucleotides and polypeptides, especially for screening candidate anti-fungal agents.

BACKGROUND OF THE INVENTION

The yeast Candida is a ubiquitous human commensal, known as the causative agent of candidiasis. The majority of the diseases are caused by the species *Candida albicans*. It is the most prevalent commensal and opportunistic fungal pathogen of humans, causing common superficial infections as well as more serious systemic and organ infections. Cannon et al. (1995) *J. Dental Research*. 74:1152–1161. Exposure to *C. albicans* at or shortly after birth results in lifelong colonization in the host tissues, such as the gastrointestinal tract, oral cavity and genital area. It has been noted that approximately 75% of women would suffer from vaginal candidiasis at some stage in their lifetime. Bossche et al. (1993) *Fungal Dimorphism* 3–10; Fidel et al. (1996) *Clin. Micro. Rev.* 9(3):335–348. Whereas *C. albicans* infection often remains localized to the initial sites of contact in healthy individuals, *C. albicans* cells can invade submucosal vessels, disseminate hematogenously and become life-threatening, especially to immunocompromised patients. The invasive forms of *C. albicans* infection are not only dangerous in their own right, but they are believed to facilitate infections by other opportunistic pathogens.

In the last decades, the incidence of severe and systemic candidiasis has increased dramatically because of the growing number of immunocompromised patients suffering from AIDS, diabetes, cancer and other conditions. In addition, the widespread use of immunosuppressants for organ transplant patients, the common practice of radiation and chemotherapy for treating malignancies, as well as the growing size of the aging population have increased the morbidity of this opportunistic pathogen. For reviews, see Rubin et al. (1993) *Eur. J Clin. Microbiol. Infect. Dis.* 12 Suppl. 1, 542; Dudley et al. (1990) *Pharmacotherapy* 10:133; Paya (1993) *Clin. Infect. Dis.* 16:677–688; Rubin (1993) *Eur. J Clin. Micro. Infect. Dis.* 12 Suppl. 1: S42–S48.

Despite decades of intensive study, the properties of *C. albicans* that contribute to its virulence are only beginning to be understood. Among the most investigated virulence factors are adherence, production of hydrolytic enzymes and adoption of various cell morphologies. Odds et al. (1994) *Am. Soc. Microbiol. News* 60:313–318. The ability of *C. albicans* to adhere to the host surfaces probably allows initial colonization and infection of the host tissues. Secretion of a variety of hydrolytic enzymes which are capable of degrading proteins and lipids is thought to generate tissue cavitation and thereby facilitate deeper penetration. The morphological transition between various forms of *C. albicans* is also considered a key determinant of virulence.

*C. albicans* cells can exist in a variety of shapes, ranging from elipsoidal budding yeast cells (also known as blastopores) to cylindrical hyphae (also known as filaments) in which cells remain attached to each other after dividing and thereby form long branched strings of connected cells (FIG. 1). Transitions between these forms take place by outgrowth of new cells with the altered morphology, rather than remodeling of pre-existing cells. The ability of *C. albicans* to adopt these different morphologies is thought to allow the fungus to adapt to, and possibly travel to, different host micro-environments. Odds et al. (1988) Candida and Candidosis (Bailliere Tindall, London, 2nd ed.); Odds et al. (1994); Odds et al. (1994) *J. Am. Acad. Dermatol.* 31:52. The regulation of cellular morphology is in response to environmental conditions. In vitro studies have shown that most *C. albicans* strains assume filamentous forms when they are subjected to either unfavorable growth conditions, such as nutrient-poor media and high $CO_2:O_2$ ratio, or host-related conditions, such as high temperature (37° C.) and mammalian serum (10%). Conversely, rich media, low temperatures and aerated conditions promote blastospore growth. Intermediate conditions can induce various pseudohyphal forms as well as true hyphae. For reviews, see Odds et al. (1988) Candida and Candidosis, Bailliere Tindall, London, ed. 2nd; Odds et al *Crit. Rev Microbiol.* (1985) 12:45; Gow et al. (1984) *Sabouraudia* 22:137. The pseudohyphal cells are elongated but still elipsoidal in shape, whereas the true hyphal cells are cylindrical and separated by perpendicular septal walls. Very little is known about the genetic identity of regulators controlling the morphological transition of *C. albicans*.

The ability of *C. albicans* to adopt these different morphologies is thought to contribute to colonization and dissemination within host tissues and thereby to promote infection. Odds (1988); Odds (1994) *J. Am. Acad. Dermatol.* 31:S2. It has been commonly suggested that the hyphal form is invasive and pathogenic, while the blastospore is the commensal non-pathogenic form. However, all morphological forms have been found within infected tissues. Histopathological examination of candidiasis lesions indicates that hyphae are not always present. More recent studies have shown that commensal *C. albicans* does not exist uniquely in the blastopore form. In fact, sometimes invading *C. albicans* cells are seen exclusively as the budding yeast form. Odds et al. (1994) *Am. Soc. Microbiol. News* 60:313–318. Despite the uncertainty with regard to the relative roles these two distinct forms of *C. albicans* have in fungal virulence, phenotypic switching represents a remarkable adaptation that *C. albicans* has acquired to cope with different host microenvironments. Identifying the genetic components that regulate the morphological transition are therefore of great significance for identifying the role of this transition in pathogenesis and developing potential therapeutic agents of candidiasis.

Current therapy available for systemic candidiasis is limited to the use of anti-fungal agents. In practice, the arsenal of anti-fungal drugs is based on a few antimycotics, such as flucytosine, amphotericin B and azole derivatives.

Many of these antimycotics are somewhat water insoluble which restrict their bioavailability and present problems in intravenous formulation. In addition, they cause serious and often difficult side effects, such as renal toxicity, bone marrow destruction, as well as unpleasant symptoms such as fever and shivering. Furthermore, the chronic use of these anti-fungal agents has led to the emergence of drug-resistant strains of Candida, which can cause fatal relapse of the disease. Dupont et al. (1995) *J. Am. Podiatric Med. Assn.* 85:104–115; Fox et al. (1991) *J. Infect. Dis.* 22:201–204; Scheife (1990) *Pharmacotherapy* 10:S133–S183. Taken together, anti-fungal therapy alone is inadequate for treating chronic candiasis. The availability of recombinant cytokines, such as interleukin-2, provides an alternative way to stimulate the cell-mediated immunity of infected individuals. However, this type of cytokine replacement therapy for fungal infections remains highly experimental. Weinberg et al. (1990) *N. Eng. J. Med.* 332: 1718.

*S. cerevisiae* Tup1 encoded by the TUP1 gene is a member of a family of WD repeat containing proteins. Tup1, along with the SSN6 protein, represses sets of genes involved in a variety of cellular processes, including glucose repression, mating, sporulation and flocculation. The gene targets of TUP1 regulation are each regulated by a distinct upstream DNA-binding protein, and each DNA-binding protein recruits to the promoter a complex containing the TUP1 protein. The biochemical mechanisms by which TUP1 in *S. cerevisiae* mediates transcriptional repression are yet not well understood. Tzamarias et al. (1994) *Nature* 369: 758; Komachi et al. *Genes Dev.* 8: 2857; Wahi et al. (1995) *Genetics* 140: 79–90; Edmondson et al. (1996) *Genes Dev.* 10: 1247.

In addition to the *S. cerevisiae* TUP1 gene, TUP1 homologs in higher eukaryotes such as human, mouse and chicken have been identified and found to be highly diverged from *S. cerevisiae* TUP1. Virtually nothing is known about the biological functions of these genes. The genomic organization of the human TUP1, however, has been characterized. It is located on chromosome 22q11, within the Digeorge syndrome critical region. Hemizygosity of this region results in DiGeorge syndrome, which is a developmental disorder characterized by aplasia or hypoplasia of the thymus and parathyroid glands, as well as conotruncal cardiac malformations. Llevadot et al. (1996) *Mammalian Genome* 7: 911–914.

In view of the alarming prevalence of life-threatening candidiasis among immunocompromised patients and the lack of satisfactory agents to treat this condition, there is a pressing need for developing better therapeutic agents to combat *C. albicans* infections.

All publications cited herein are hereby incorporated by reference in their entirety.

SUMMARY OF THE INVENTION

This invention provides *C. albicans* TUP1 gene polynucleotide sequences, Tup1 polypeptides encoded by these sequences, antibodies that bind to these polypeptides, compositions comprising any of the above, as well as methods using the polynucleotides, polypeptides, and/or antibodies.

Accordingly, in one aspect, the invention includes an isolated polynucleotide comprising a sequence encoding a Tup1 polypeptide from *C. albicans*, wherein the polypeptide complements a tup1 mutation in a yeast cell. The Tup1 polypeptide encoded is found within the sequence depicted in SEQ ID NO:2, including from about 190 to about 465, about 1 to about 465, about 1 to about 512 of SEQ ID NO:2, as well as the entire sequence of SEQ ID NO:2.

In another aspect, the invention provides isolated polynucleotides based on the sequence depicted in SEQ ID NO:1, and as such may comprise nucleotides from about 904 to about 1728, from about 354 to about 1728 of SEQ ID NO:1, as well as the entire sequence of SEQ ID NO:1.

In another aspect, the invention provides an isolated polynucleotide comprising the polynucleotide sequence of SEQ ID NO:1. In another aspect, the isolated polynucleotide comprises a region of at least 20 contiguous nucleotides, with the region having at least 80%, preferably at least 85%, sequence identity with a sequence depicted in SEQ ID NO:1. In other embodiments, the invention provides an isolated polynucleotide comprising a region of at least 20 contiguous nucleotides, with the region (and/or isolated polypeptide comprsing this region) able to hybridize under stringent conditions to a sequence depicted in SEQ ID NO:1, particularly SEQ ID NO:1.

In another aspect, the invention includes cloning vectors, expression vectors, host cells, and compositions comprising any of the above polynucleotides.

In another aspect, the invention provides an isolated polypeptide comprising a Tup1 polypeptide sequence from *C. albicans*, wherein the polypeptide complements a tup1 mutation in a yeast cell. In one embodiment, the polypeptide comprises about amino acid 190 to about 465 of SEQ ID NO:2. In another embodiment, the polypeptide comprises about amino acid 1 to about amino acid 465 of SEQ ID NO:2. In another embodiment, the polypeptide comprises the sequence of SEQ ID NO:2.

In another aspect, the invention includes compositions comprising any of the polypeptides of the invention.

In another aspect, the invention provides purified antibodies that are capable of specifically binding to a polypeptide of the invention. In another aspect, the invention provides a monoclonal antibody capable of specifically binding to a polypeptide of the invention.

In another aspect, the invention provides an isolated *C. albicans* cell having compromised TUP1 function.

In another aspect, the invention provides a method for detecting a polynucleotide from *C. albicans* in a sample comprising the steps of (a) contacting polynucleotide from *C. albicans* from a sample with a polynucleotide of this invention under conditions that permit the formation of a stable duplex; and (b) detecting the stable duplex formed in step (a), if any.

The invention also provides a method for detecting a polynucleotide from *C. albicans* in a sample comprising the steps of (a) conducting an amplification reaction on a polynucleotide in the sample using a primer consisting of a fragment of the polynucleotide sequence of SEQ ID NO:2; and (b) detecting the presence of amplified copies of the polynucleotide, if any.

The invention also provides a method for detecting an anti-*C. albicans* Tup1 antibody in a biological sample, comprising the steps of: (a) contacting antibody from the sample with a polypeptide of this invention under conditions which permit formation of a stable antigen-antibody complex; and (b) detecting said stable complexes formed in step (a), if any.

The invention also provides a method for detecting a *C. albicans* Tup1 polypeptide in a biological sample, comprising the steps of: (a) contacting polypeptide from the biological sample with an antibody of this invention under conditions that permit the formation of a stable antigen-antibody complex; and (b) detecting said stable complexes formed in step (a), if any.

In another aspect, the invention provides methods for identifying an agent that may control virulence in *C. albicans*. These methods may be in vitro or in vivo (i.e., cell-based). In one embodiment, the invention provides a method for identifying an agent that may control virulence in *C. albicans*, said method comprising:

(a) contacting at least one agent to be tested with a suitable host cell that has TUP1 function;

(b) analyzing at least one characteristic which is associated with loss of TUP1 function in said host cell, wherein an agent is identified by its ability to elicit at least one such characteristic.

In another embodiment, the invention provides a method for identifying an agent that may control virulence in *C. albicans*, said method comprising:

(a) introducing a polynucleotide encoding *C. albicans* Tup1 or a functional fragment thereof into a suitable host cell that otherwise lacks TUP1 function, wherein TUP1 function is restored in said host cell;

(b) contacting said host cell of step (a) with at least one agent to be tested;

(c) analyze at least one characteristic which is associated with loss of TUP1 function in said host cell, wherein an agent is identified by its ability to elicit at least one such characteristic.

In another aspect, the invention provides compositions for controlling virulence in *C. albicans* comprising any agent identified by the screening methods above.

In another aspect, the invention provides kits for detection or quantification of (a) a polynucleotide comprising a TUP1 polynucleotide from *C. albicans*; or (b) a *C. albicans* polypeptide; or (c) an anti-*C. albicans* antibody in a biological sample. These kits contain (a) a polynucleotide of the invention; or (b) an antibody of the invention; or (c) a polypeptide of the invention, respectively.

In another aspect, the invention provides methods of inhibiting virulence of *C. albicans* comprising compromising *C. albicans* TUP1 function.

In another aspect, the invention provides a method of isolating a polynucleotide sequence from *C. albicans* that is associated with *C. albicans* TUP1 function, said method comprising identifying a transcribed polynucleotide which is repressed upon *C. albicans* TUP1 expression.

BRIEF DESCRIPTION OF THE DRAWINGS

FIGS. 2A and 2B compare TUP1 gene products between *C. albicans* and *S. cerevisiae*. FIG. 2A (SEQ ID NO:2 and SEQ ID NO:3) compares the amino acid sequences of TUP1 polypeptide (based on translation from the DNA sequences). Identical residues are denoted by blocks. FIG. 2B is a schematic diagram depicting the relative arrangement of their N-terminal conserved domains (hatched) and their C-terminal WD40 repeated motifs (filled).

FIG. 3A is a diagram of the *C. albicans* TUP1 locus showing the open reading frame as a box containing conserved sequence elements (as in FIG. 2B). The top line represents the original genomic clone, the insert of plasmid p371. The second line represents the disruption fragment contained on p383C. The third line represents the rescuing fragment carried on p405, and the last line corresponds to the frameshift mutant (p418), created by filling in the indicated EcoRI site of p405.

FIGS. 6(a) through 6(c) (SEQ ID NO:1) depict the DNA sequence and translated amino acid sequence of *C. albicans* TUP1 gene.

MODES FOR CARRYING OUT THE INVENTION

Figure 1:
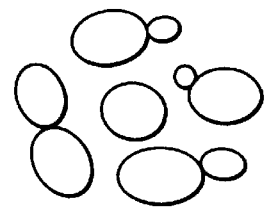
FIG. 1 is a schematic drawing depicting the major morphologies of *C. albicans*: blastospores, pseudohypha, and true hypha.
Figure 1:
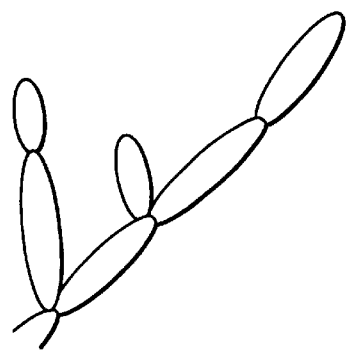
Figure 1:
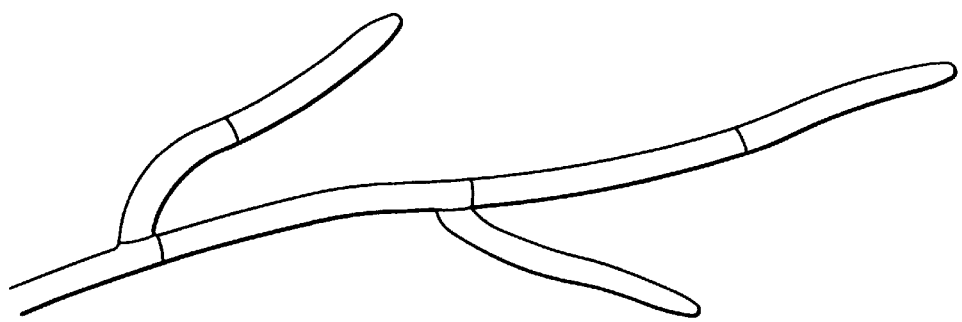

We have discovered and cloned the TUP1 gene from the pathogenic yeast *C. albicans* and have discovered that this gene plays a key role in controlling filamentous growth of *C. albicans*. The transition from blastophore to filamentous form may play a significant role in the pathogenicity of this organism. Further, we have found that *C. albicans* cells lacking TUP1 function display poor infectivity in mice. This indicates that discovery of agents that compromise *C. albicans* TUP1 function may have useful anti-fungal activity. This novel basis for identifying such agents is particularly important because these agents may well be less toxic than currently used anti-fungal agents due to: (a) the TUP1 human gene homolog is highly diverged from yeast TUP1 and (b) this (and other downstream) gene(s) is associated with the filamentous growth are particularly found in fungal (yeast) systems, as opposed to more fundamental functions (i.e., functions shared across wide ranges of organisms, such as yeast and human) such as DNA replication.

Accordingly, the invention provides TUP1 polynucleotide sequences, including polynucleotides encoding the TUP1 gene product Tup1. These polynucleotide sequences are useful as probes, for example, for detecting the presence of *C. albicans* in a biological sample. They are also useful for producing TUP1 or fragments thereof. The invention also provides Tup1 polypeptides which are useful, inter alia, for making antibodies or for detection of *C. albicans* in a biological sample and as a basis for rational drug design. Further, the invention provides antibodies raised against Tup1 or fragments of Tup1. The invention also provides methods using the TUP1 polynucleotides of the invention, such as methods of detecting the presence of *C. albicans* in a biological sample. Other methods of the invention include screening methods for identifying agents that compromise *C. albicans* TUP1 function and methods for identifying genes and gene products which are regulated by TUP1 or are otherwise involved in a TUP1 pathway. These and other embodiments will be described in more detail below.

Definitions

As used herein, "TUP1" or "TUP1 gene" refers to the *C. albicans* TUP1 gene described herein. Unless otherwise specified, the terms "TUP1" and "*C. albicans* TUP1" are interchangeable. When referring to TUP1 (i.e., the TUP1 gene) from another organism, such as *S. cerevisiae*, the reference to TUP1 will include reference to that organism (for example, "*S. cerevisiae* TUP1"). As is understood in the art, the TUP1 gene includes, not only the coding sequences, but also 5' and 3' flanking sequences, as shown in SEQ ID NO: 1. A "fragment" of TUP1 is a portion of the TUP1 gene, and as such may contain coding and/or non-coding sequences. Preferably, a fragment of TUP1 comprises at least 10 contiguous nucleotides, more preferably at least 15, more preferably at least 25, more preferably at least 30, more preferably at least 50, more preferably at least 100 contiguous nucleotides.

"Tup1" refers to a protein (polypeptide) product encoded in the *C. albicans* TUP1 gene. The sequence of full-length Tup1 is shown in SEQ ID NO: 2 as well as FIG. 2. Unless otherwise specified, the terms "Tup1" and "*C. albicans* Tup1" are interchangeable. When referring to Tup1 (i.e., the product of the TUP1 gene) in another organism, (for example, the reference to Tup1 will refer to that organism (i.e., "*S. cerevisiae* Tup1"). A "fragment" of full-length Tup1 is a portion of the TUP1 gene product. It is understood that Tup1 may exist in more than one form, such as a single Tup1 polypeptide, an assembly of at least one Tup1 polypeptide, and/or within a complex (i.e., comprising multi-subunits) containing at least one Tup1 polypeptide with at least one other polypeptide.

A "TUP1 polynucleotide" refers to any of the polynucleotide embodiments described herein and is based on the TUP1 gene polynucleotide sequence (SEQ ID NO:1). A "Tup1 polypeptide" refers to a polypeptide product encoded by or within TUP1; thus, a "Tup1 polypeptide" refers to any of the polypeptide embodiments described herein, including full-length Tup1.

"TUP1 function" refers to an activity or characteristic associated with expression of TUP1. The nature of these activity(s) or characteristic(s) depend upon the organism in which TUP1 function is found but appear to stem from transcriptional regulation (i.e. repression) of certain genes. These activities and characteristics include, but are not limited to, expression of TUP1 (i.e., transcription and translation of Tup1), binding other proteins (particularly DNA binding proteins), regulation (whether induction or repression) of certain genes, and particular phenotypic characteristics. These activities and characteristics will be described in more detail below. Because TUP1 exerts control over a number of other genes, it is understood that the term "TUP1 function" encompasses results and characteristics that stem from TUP1 expression which include affecting gene expression of any gene(s) that is regulated by TUP1 gene product or an active fragment thereof. For example, if gene A is repressed by expression of TUP1, then lack of expression of gene A is a function of TUP1. Conversely, expression of gene A indicates a compromise of TUP1 function.

As used herein, a characteristic which is associated with a "compromise of TUP1 function" is a characteristic which is associated with a decrease in TUP1 function. This decrease may range from partial to total loss, or knockout, of TUP1 function. Characteristics associated with a compromise of TUP1 function depend upon the organism for which this is being assessed and will be discussed in detail below. Compromise of TUP1 function can occur as a result of an effect at any point along any pathway in which TUP1 exerts control, from transcription of the TUP1 gene, to TUP1 expression (i.e., transcription and/or translation), to affecting regulation of any gene(s) under TUP1 control, to activity (i.e.) associated with regulation of these gene(s).

A polypeptide or polynucleotide (used interchangeably in this context) that "complements" a tup1 mutation in a yeast cell substitutes, or provides, a function of TUP1. A "tup1" mutation uses standard terminology in the art and refers to a mutation in the TUP1 gene, which may impart either partial to total loss of TUP1 function. Complementation is a term well-understood in the art, and as used herein refers to the ability of a polynucleotide (via its encoded polypeptide) to restore at least one function associated with wild type TUP1.

As used herein, a "polynucleotide" is a polymeric form of nucleotides of any length, which contain deoxyribonucleotides, ribonucleotides, and/or their analogs. The terms "polynucleotide" and "nucleotide" as used herein are used interchangeably. Polynucleotides may have any three-dimensional structure, and may perform any function, known or unknown. The term "polynucleotide" includes double-, single-stranded, and triple-helical molecules. Unless otherwise specified or required, any embodiment of the invention described herein that is a polynucleotide encompasses both the double-stranded form and each of two complementary single-stranded forms known or predicted to make up the double stranded form. Not all linkages in a polynucleotide need be identical.

The following are non-limiting examples of polynucleotides: a gene or gene fragment, exons, introns, mRNA, tRNA, rRNA, ribozymes, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs. The use of uracil as a substitute for thymine in a deoxyribonucleic acid is also considered an analogous form of pyrimidine.

If present, modification to the nucleotide structure may be imparted before or after assembly of the polymer. The sequence of nucleotides may be interrupted by non-nucleotide components. A polynucleotide may be further modified after polymerization, such as by conjugation with a labeling component. Other types of modifications included in this definition are, for example, "caps", substitution of one or more of the naturally occurring nucleotides with an analog, internucleotide modifications such as, for example, those with uncharged linkages (e.g., methyl phosphonates, phosphotriesters, phosphoamidates, cabamates, etc.) and with charged linkages (e.g., phosphorothioates, phosphorodithioates, etc.), those containing pendant moieties, such as, for example, proteins (e.g., nucleases, toxins, antibodies, signal peptides, ploy-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide(s).

Further, any of the hydroxyl groups ordinarily present in the sugars may be replaced by phosphonate groups, phosphate groups, protected by standard protecting groups, or activated to prepare additional linkages to additional nucleotides, or may be conjugated to solid supports. The 5' and 3' terminal OH groups can be phosphorylated or substituted with amines or organic capping group moieties of from 1 to 20 carbon atoms. Other hydroxyls may also be derivatized to standard protecting groups.

Polynucleotides can also contain analogous forms of ribose or deoxyribose sugars that are generally known in the art, including, but not limited to, 2'-O-methyl-, 2'-O-allyl, 2'-fluoro- or 2'-azido-ribose, carbocyclic sugar analogs, α-anomeric sugars, epimeric sugars such as arabinose, xyloses or lyxoses, pyranose sugars, furanose sugars, sedoheptuloses, acyclic analogs and a basic nucleoside analogs such as methyl riboside.

Although conventional sugars and bases will be used in applying the method of the invention, substitution of analogous forms of sugars, purines and pyrimidines can be advantageous in designing a final product, as can alternative backbone structures like a polyamide backbone.

A polynucleotide or polynucleotide region has a certain percentage (for example, 80%, 85%, 90%, or 95%) of "sequence identity" to another sequence means that, when aligned, that percentage of bases are the same in comparing the two sequences. This alignment and the percent homology or sequence identity can be determined using software programs known in the art, for example those described in *Current Protocols in Molecule Biology* (F. M. Ausubel et al., eds., 1987) Supplement 30, section 7.718, Table 7.7.1. A preferred alignment program is ALIGN Plus (Scientific and Educational Software, Pennsylvania).

A nucleotide is said to "encode" a polypeptide if, in its native state or when manipulated by methods well known to those skilled in the art, it can be transcribed and/or translated to produce the polypeptide or a fragment thereof. For purposes of this invention, and to avoid cumbersome referrals to complementary strands, the anti-sense (or complementary) strand of such a polynucleotide is also said to encode the sequence; that is, a polynucleotide sequence that "encodes" a polypeptide includes both the conventional coding strand and the complementary sequence (or strand).

A "primer" is a short polynucleotide, generally with a free 3'-OH group, that binds to a target potentially present in a sample of interest by hybridizing with the target, and thereafter promoting polymerization of a polynucleotide complementary to the target.

A "probe" when used in the context of polynucleotide manipulation refers to a polynucleotide which is provided as a reagent to detect a target potentially present in a sample of interest by hybridizing with the target. Usually, a probe will comprise a label or a means by which a label can be attached, either before or subsequent to the hybridization reaction. Suitable labels include, but are not limited to radioisotopes, fluorochromes, chemiluminescent compounds, dyes, and enzymes.

"Transformation" or "transfection" refers to the insertion of an exogenous polynucleotide into a host cell, irrespective of the method used for the insertion, for example, lipofection, transduction, infection or electroporation. The exogenous polynucleotide may be maintained as a non-integrated vector, for example, a plasmid, or alternatively, may be integrated into the host cell genome.

The terms "polypeptide", "oligopeptide", "peptide" and "protein" are used interchangeably herein to refer to polymers of amino acids of any length. The polymer may be linear or branched, it may comprise modified amino acids, it may be interrupted by non-amino acids, and it may be assembled into a complex of more than one polypeptide chain. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art. It is understood that, because the polypeptides of this invention are based upon an antibody, the polypeptides can occur as single chains or associated chains.

A polypeptide "fragment" (also called a "region") of Tup1 (or a "Tup1 fragment" or "Tup1 region") is a polypeptide comprising an amino acid sequence of Tup1 that has at least 5 contiguous amino acids of a sequence of Tup 1, more preferably at least 10 contiguous amino acids, more preferably at least about 15 contiguous amino acids, even more preferably at least about 25 contiguous amino acids, even more preferably at least about 30 contiguous amino acids, even more preferably at least about 40 contiguous amino acids. A Tup1 fragment may be characterized as having any of the following functions: (a) ability to bind another protein, particularly a protein associated with gene regulation; (b) ability to elicit a humoral and/or cellular immune response; (c) ability to regulate (i.e., repress or induce) another gene in the pathway regulated by TUP1; (d) ability to elicit a characteristic associated with TUP1 function. For purposes of this invention, it is understood that a Tup1 fragment does not have the same amino acid sequence as *S. cerevisiae* Tup1.

A "fusion polypeptide" is a polypeptide comprising regions in a different position than occurs in nature. The regions may normally exist in separate proteins and are brought together in the fusion polypeptide, or they may normally exist in the same protein but are placed in a new arrangement in the fusion polypeptide.

A "functionally preserved" variant of a TUP1 polynucleotide or Tup1 polypeptide is a TUP1 or Tup1 sequence which retains at least one aspect of TUP1 function. Functionally preserved variants can be due to differences in linear sequence, arising from, for example, single base mutation (s), addition(s), deletion(s), and/or modification(s) of the bases. The difference can also arise from changes in the sugar(s) and/or linkage(s) between the bases. Regarding polypeptides, functionally preserved variants may arise, for example, by conservative and/or non-conservative amino acid substitutions, amino acid analogs, and deletions. As described in Example 3, deletion of a portion of the amino acid sequence of the full-length Tup1 polypeptide did not destroy Tup1 function. The function that is preserved depends upon the relevant function being considered. For example, if a TUP1 polynucleotide is considered for a probe, then the ability of a variant polynucleotide sequence to hybridize to the target is the relevant function. If a polynucleotide is considered for its ability to encode a Tup1 polypeptide (or fragment thereof), then the ability of a variant sequence to encode the same polypeptide is the relevant function. If a Tup1 polypeptide is considered for its ability to bind to a particular entity (such as an antibody or another protein), then the ability of a variant sequence to encode a polypeptide with equivalent binding characteristics that is relevant.

A "vector" is a self-replicating nucleic acid molecule that transfers an inserted nucleic acid molecule into and/or between host cells. The term includes vectors that function primarily for insertion of a nucleic acid molecule into a cell, replication of vectors that function primarily for the replication of nucleic acid, and expression vectors that function for transcription and/or translation of the DNA or RNA. Also included are vectors that provide more than one of the above functions.

"Expression vectors" are defined as polynucleotides which, when introduced into an appropriate host cell, can be transcribed and translated into a polypeptide(s). An "expression system" usually connotes a suitable host cell comprised of an expression vector that can function to yield a desired expression product.

A "host cell" includes an individual cell or cell culture which can be or has been a recipient for vector(s) or for incorporation of nucleic acid molecules and/or proteins. Host cells include progeny of a single host cell, and the progeny may not necessarily be completely identical (in morphology or in genomic of total DNA complement) to the original parent cell due to natural, accidental, or deliberate mutation. A host cell includes cells transfected in vivo with a polynucleotide(s) of this invention.

As used herein, "expression" includes transcription and/or translation.

A "biological sample" encompasses a variety of sample types obtained from an individual and can be used in a diagnostic or monitoring assay. The definition encompasses blood and other liquid samples of biological origin, solid tissue samples such as a biopsy specimen or tissue cultures or cells derived therefrom, and the progeny thereof. The definition also includes samples that have been manipulated in any way after their procurement, such as by treatment with reagents, solubilization, or enrichment for certain components, such as proteins or polynucleotides. The term "biological sample" encompasses a clinical sample, and also includes cells in culture, cell supernatants, cell lysates, serum, plasma, biological fluid, and tissue samples.

"Heterologous" means derived from (i.e., obtained from) a genotypically distinct entity from the rest of the entity to which it is being compared. For example, a polynucleotide may be placed by genetic engineering techniques into a plasmid or vector derived from a different source, thus becoming a heterologous polynucleotide. A promoter which is linked to a coding sequence with which it is not naturally linked is a heterologous promoter.

An "isolated" or "purified" polynucleotide, polypeptide, antibody or cell is one that is substantially free of the materials with which it is associated in nature. By substantially free is meant at least 50%, preferably at least 70%, more preferably at least 80%, and even more preferably at least 90% free of the materials with which it is associated in nature. As used herein, an "isolated" polynucleotide or polypeptide also refers to recombinant polynucleotides or polypeptides, which, by virtue of origin or manipulation: (1) are not associated with all or a portion of a polynucleotide or polypeptide with which it is associated in nature, (2) are linked to a polynucleotide or polypeptide other than that to which it is linked in nature, or (3) does not occur in nature, or (4) in the case of polypeptides arise from expression of recombinant polynucleotides.

A "reagent" polynucleotide, polypeptide, or antibody, is a substance provided for a reaction, the substance having some known and desirable parameters for the reaction. A reaction mixture may also contain a "target", such as a polynucleotide, antibody, polypeptide, or assembly of polypeptides that the reagent is capable of reacting with. For example, in some types of diagnostic tests, the presence and/or amount of the target in a sample is determined by adding a reagent, allowing the reagent and target to react, and measuring the amount of reaction product (if any). In the context of clinical management, a "target" may also be a cell, collection of cells, tissue, or organ that is the object of an administered substance, such as a pharmaceutical compound.

A "stable duplex" of polynucleotides, or a "stable complex" formed between any two or more components in a biochemical reaction, refers to a duplex or complex that is sufficiently long-lasting to persist between formation of the duplex or complex and subsequent detection, including any optional washing steps or other manipulation that may take place in the interim.

As used herein, the term "agent" means a biological or chemical compound such as a simple or complex organic or inorganic molecule, a peptide, a protein, oligonucleotide, polynucleotide, carbohydrate, or lipoprotein. A vast array of compounds can be synthesized, for example oligomers, such as oligopeptides and oligonucleotides, and synthetic organic compounds based on various core structures, and these are also included in the term "agent". In addition, various natural sources can provide compounds for screening, such as plant or animal extracts, and the like. Compounds can be tested singly or in combination with one another. "Controlling virulence" means that an agent may impair the ability of a $C.$ $albicans$ cell to become pathogenic. "Virulence" is a term well understood in the art and means an ability to invade, infect, multiply, spread, and/or colonize host to the detriment of the host. "Virulence" and "pathogenicity" and "infectivity" are used interchangeably herein. An agent which may control virulence in $C.$ $albicans$ is one which is selected by the screening methods described herein and may, upon further study, prove to control $C.$ $albicans$ virulence and may even exert therapeutic activity.

An "individual" is a vertebrate, preferably a mammal, more preferably a human. Mammals include, but are not limited to, farm animals, sport animals, and pets.

A "vaccine" is a pharmaceutical composition for human or animal use, which is administered with the intention of conferring the recipient with a degree of specific immunological reactivity, or immune response, against a particular target, or group of targets. The immunological reactivity may be antibodies or cells (particularly B cells, plasma cells, T helper cells, and cytotoxic T lymphocytes and their precursors) that are immunologically reactive against the target or any combination thereof. For purposes of this invention, the target is Tup1 polypeptide(s) (whether full length or functional fragment thereof). Immunological reactivity may be desired for experimental purposes, for treatment, or for the elimination of a particular substance.

An "antibody" (interchangeably used in plural form) is an immunoglobulin molecule capable of specific binding to a target, such as a polypeptide, through at least one antigen recognition site, located in the variable region of the immunoglobulin molecule. As used herein, the term encompasses not only intact antibodies, but also fragments thereof (such as Fab, Fab', F(ab')$_2$, Fv, single chain (ScFv), mutants thereof, fusion proteins, humanized antibodies, and any other modified configuration of the immunoglobulin molecule that comprises an antigen recognition site of the required specificity.

"Immunological recognition" or "immunological reactivity" refers to the specific binding of a target through at least one antigen recognition site in an immunoglobulin or a related molecule, such as a B cell receptor or a T cell receptor.

The term "antigen" refers to the target molecule that is specifically bound by an antibody through its antigen recognition site. The antigen may, but need not be chemically related to the immunogen that stimulated production of the antibody. The antigen may be polyvalent, or it may be a monovalent hapten. Examples of kinds of antigens that can be recognized by antibodies include polypeptides, polynucleotides, other antibody molecules, oligosaccharides, complex lipids, drugs, and chemicals.

An "immunogen" is an antigen capable of stimulating production of an antibody when injected into a suitable host, usually a mammal. Compounds may be rendered immunogenic by many techniques known in the art, including crosslinking or conjugating with a carrier to increase valency, mixing with a mitogen to increase the immune response, and combining with an adjuvant to enhance presentation.

General Techniques

The practice of the present invention will employ, unless otherwise indicated, conventional techniques of molecular biology (including recombinant techniques), microbiology, cell biology, biochemistry and immunology, which are within the skill of the art. Such techniques are explained fully in the literature, such as: "Molecular Cloning: A Laboratory Manual", second edition (Sambrook et al., 1989); "Oligonucleotide Synthesis" (M. J. Gait, ed., 1984); "Animal Cell Culture" (R. I. Freshney, ed., 1987); "Methods in Enzymology" (Academic Press, Inc.); "Handbook of Experimental Immunology" (D. M. Wei & C. C. Blackwell, eds.); "Gene Transfer Vectors for Mammalian Cells" (J. M. Miller & M. P. Calos, eds., 1987); "Current Protocols in Molecular Biology" (F. M. Ausubel et al., eds., 1987); "PCR: The Polymerase Chain Reaction", (Mullis et al., eds., 1994); "Current Protocols in Immunology" (J. E. Coligan et al., eds., 1991).

For techniques related to *C. albicans* and other yeast, see, inter alia, *Guide to Yeast Genetics and Molecular Biology*, Guthrie and Fink (eds.) (1991) Vol. 194; Fonzi et al. (1993) *Genetics* 134: 717–728 and references therein.

Polynucleotides of the Invention

The present invention provides TUP1 polynucleotides, including TUP1 polynucleotides encoding *C. albicans* Tup1 (i.e., a Tup1 polypeptide), polynucleotides from the flanking region(s) of TUP1, vectors containing these polynucleotides, host cells containing these polynucleotides, and compositions comprising these polynucleotides. These polynucleotides are isolated and/or produced by chemical and/or recombinant methods, or a combination of these methods. Unless specifically stated otherwise, the term "polynucleotides" shall include all embodiments of the polynucleotides of this invention.

The polynucleotides of this invention are useful as probes, primers, in expression systems, and in screening systems. Especially useful applications of the polynucleotides will be discussed below.

Figure 2B:
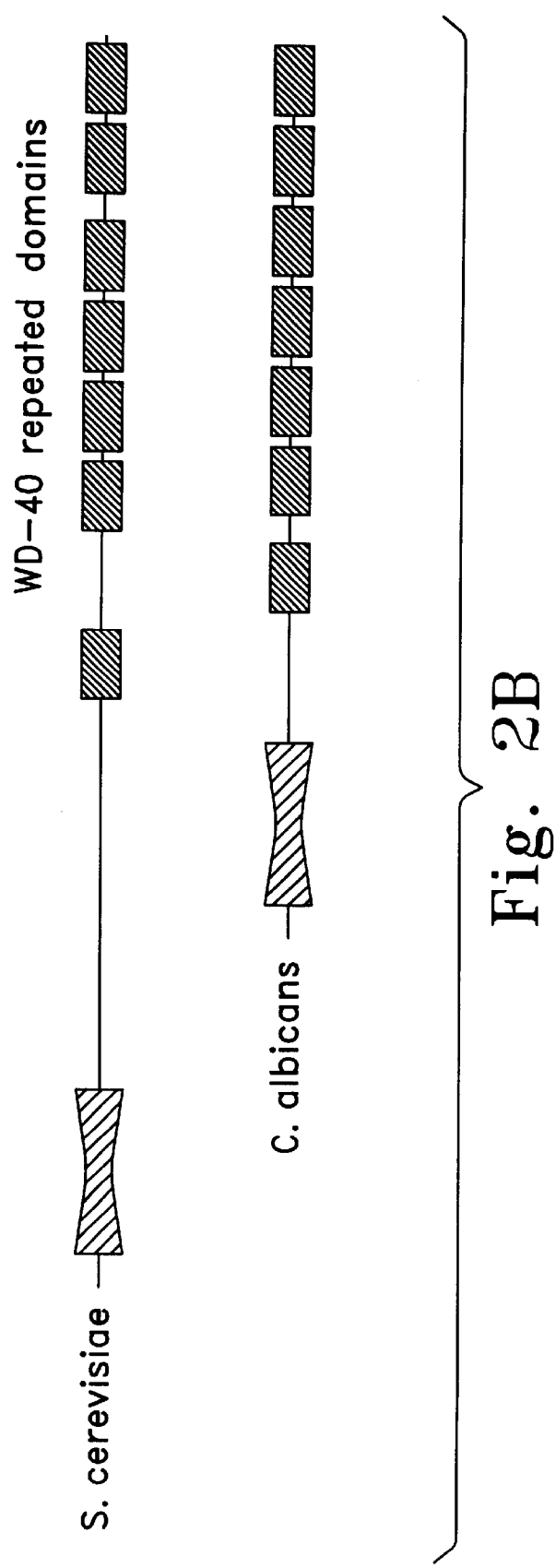

The cloning of *C. albicans* TUP1 gene is described in Example 1. A comparison between *C. albicans* and *S. cerevisiae* TUP1 gene products is provided in FIG. 2. There is a 67% identity over the entire amino acid sequence (FIG. 2A). Major conserved features are the seven WD40 repeats at the COOH-terminus of TUP1 and the $NH_2$ terminus, including a proximal glutamine-rich segment (FIG. 2B). WD40 amino acid sequence repeats are found in many eukaryotic proteins, including β subunits of heterotrimeric G-proteins, Wall et al. (1995) *Cell* 83:1047, transducin-like enhancer of split (TLE) protein (Hartley et al. (1988) *Cell* 55:785–795), and CDC4 (Yochem et al. (1987) *J. Mole. Biol.* 195:233–245).

By constructing a homozygous tup1 deletion (knockout) mutant TUP1 function has been identified as controlling filamentous growth in *C. albicans*, as shown in Example 3. The conversion between the non-filamentous and filamentous state is considered to play an important role in pathogenesis of *C. albicans*. Significantly, *C. albicans* TUP1 complements *S. cerevisiae* TUP1 function (i.e., *C. albicans* Tup 1 functions in *S. cerevisiae* when expressed in an *S. cerevisiae* strain deficient in Tup1 function), as shown in Example 2, allowing convenient screening assays to be performed using *S. cerevisiae*.

Accordingly, the present invention provides an isolated polynucleotide that contains a sequence encoding a Tup1 polypeptide from *C. albicans* wherein the polypeptide complements a tup1 mutation in a yeast cell. The yeast cell may be, for example, *S. cerevisiae* or *C. albicans*, although any of the yeast cells described herein may be suitable, as long as they have a TUP1 gene. For example, the invention includes an idolsted polyncueltode encoding at least 7, preferably at least 10, preferably at least 15, preferably at least 20, preferably at least 25, contiguous amino acids, of a sequence depicted in SEQ ID NO:1, wherein the encoded polypeptide complements a tup1 mutation in a yeast cell.

The complementation may be to any function associated with TUP1, and need not complement all functions associated with TUP1. For example, because one aspect of TUP1 function is a gene repressor, particularly in *S. cerevisiae* and *C. albicans*, complementation may be evidenced by repression of a gene that is regulated by TUP1. Because one aspect of TUP1 function in *C. albicans* is repression of filamentous growth, complementation in this cell system may be evidenced by reduction of filamentous growth. Because one aspect of TUP1 function in *C. albicans* is virulence (as evidenced by lack of infectivity or virulence in a tup1 knockout; Example 4), complementation may be evidenced by an increase in virulence.

Aspects of TUP1 function depend on the particular cell in which complementation is being assayed, and also include phenotypes associated with TUP1 function, such as a certain cell shape, lack of temperature sensitivity, presence or absence of filamentous growth patterns, mating characteristics, and presence or absence of flocculence (clumping) growth patterns. This list is non-limiting, and various aspects of TUP1 function in various cell types are described herein, any of which are suitable for complementation.

As noted above, *C. albicans* full-length Tup1 contains a series of WD40 repeat motifs. Simon et al. (1991) *Science* 252:802–808. Similar motifs are also present in *S. cerevisiae* Tup1 as well as other proteins. A single WD40 repeat has been shown to be capable of binding to the SSN6 protein which is found tightly complexed with *S. cerevisiae* Tup1. Redd et al. (1997) *J. Biol. Chem.* 272: 11193–11197. It is likely that these WD40 repeat regions play a role in *C. albicans* Tup1 function, particularly in binding other proteins. Accordingly, in one embodiment, the invention encompasses a polynucleotide comprising a polynucleotide encoding at least one WD40 repeat element within SEQ ID NO:2, provided that this WD40 encoding nucleotide sequence is different than that found in *S. cerevisiae* Tup1. FIG. 2 shows that putative WD40 regions from *C. albicans* contain different sequences than that of *S. cerevisiae*. In another embodiment, the Tup1 polypeptide encoded within the polynucleotide is the sequence from about 190 to about 465 of SEQ ID NO:2. This embodiment encompasses 6 putative WD40 repeat regions. According to Example 2, the last putative repeat region is not necessary for complementation of *S. cerevisiae* tup1.

In another embodiment, the Tup1 polypeptide encoded within the polynucleotide is the sequence from about 1 to 465 of SEQ. ID. NO:2. This partial coding sequence was shown to complement *S. cerevisiae* tup1 (Example 2), indicating that fragments of *C. albicans* Tup1 are functional.

In another embodiment, the Tup1 polypeptide encoded within the polynucleotide is the sequence from about 1 to about 512 of SEQ ID NO:2.

In another embodiment, the invention includes an isolated polynucleotide comprising nucleotides about 904 to about 1728 of SEQ ID NO:1. In another embodiment, the invention includes an isolated polynucleotide comprising nucleotides about 354 to about 1728 of SEQ ID NO:1. In another embodiment, the invention provides an isolated polynucleotide comprising the polynucleotide sequence of SEQ ID NO:1.

The invention includes modifications to the TUP1 polynucleotides described above such as deletions, substitutions, additions, or changes in the nature of any nucleic acid moieties. A "modification" is any difference in nucleotide sequence as compared to a polynucleotide shown herein to encode a Tup1 polypeptide, and/or any difference in terms of the nucleic acid moieties of the polynucleotide(s). Such changes can be useful to facilitate cloning and modifying expression of TUP1 polynucleotides. Such changes also can be useful for conferring desirable properties to the polynucleotide(s), such as stability. The definition of polynucleotide provided herein gives examples of these modifications. Hence, the invention also includes functionally-preserved variants of the nucleic acid sequences disclosed herein, which include nucleic acid substitutions, additions, and/or deletions.

The invention encompasses TUP1 polynucleotides including full-length (unprocessed), processed, coding, non-coding or portions thereof, provided that these polynucleotides contain a region encoding at least a portion of Tup1. Also embodied are the mRNA and cDNA sequences and fragments thereof that include a portion Tup1 encoding segment.

The invention also encompasses polynucleotides encoding for functionally equivalent variants and derivatives of full-length Tup1 and functionally equivalent fragments thereof which may enhance, decrease or not significantly affect properties of the polypeptides encoded thereby, provided that these functionally equivalent variants do not have the same amino acid sequence as in *S. cerevisiae* Tup1 (FIG. 2A.). For instance, changes in a DNA sequence that do not change the encoded amino acid sequence, as well as those that result in conservative substitutions of amino acid residues, non-deleterious non-conservative substitutions, one or a few amino acid deletions or additions, and substitution of amino acid residues by amino acid analogs are those which will not significantly affect properties of the encoded polypeptide. Nucleotide substitutions that do not alter the amino acid residues encoded can be useful for optimizing gene expression in different systems. Suitable substitutions are known to those of skill in the art and are made, for instance, to reflect preferred codon usage in the particular expression systems. In another example, alternatively spliced polynucleotides can give rise to a functionally equivalent fragment or variant of Tup1. Alternatively processed polynucleotide sequence variants are defined as polynucleotide sequences corresponding to mRNAs that differ in sequence for one another but are derived from the same genomic region, for example, mRNAs that result from: 1) the use of alternative promoters; 2) the use of alternative polyadenylation sites; or 3) the use of alternative splice sites.

The TUP1 polynucleotides of the invention also include polynucleotides encoding other Tup1 fragments. The polynucleotides encoding Tup1 fragments are useful, for example, as probes, therapeutic agents, and as a template for encoding various functional and/or binding domains of Tup1. Accordingly, the invention includes a polynucleotide that comprises a region of at least 15 contiguous nucleotides, more preferably at least about 20 contiguous nucleotides, more preferably at least about 25 contiguous nucleotides, more preferably at least about 35 contiguous nucleotides, more preferably at least about 50 contiguous nucleotides, even more preferably at least about 75 contiguous nucleotides, even more preferably at least about 100 contiguous nucleotides, even more preferably at least about 200 contiguous nucleotides, even more preferably at least about 300 contiguous nucleotides.

Another embodiment of the invention is isolated polynucleotoides comprising a region of at least 20 contiguous nucleotides, with the region having at least 80% sequence identity with a sequence depicted in SEQ ID NO:1. The region may also have 85% sequence identity, preferably 90% sequence identity, more preferably 95% sequence identity. Further, the invention includes polynucleotides comprising longer regions having at least 80%, preferably 85%, preferably 90%, more preferably 95% sequence identity with a sequence depicted in SEQ ID NO:1. These regions may comprise at least 25 contiguous nucleotides, 30 contiguous nucleotides, 50 contiguous nucleotides, 60 contiguous nucleotides, 75 contiguous nucleotides, or 100 contiguous nucleotides. Another embodiment of the invention is an isolated polynucleotide comprising a sequence with which a sequence of at least contained of at least 20 contiguous nucleotides depicted in SEQ ID NO:1 is 80% identical. These embodiments may also have larger regions and/or higher sequence identity (as discussed above)

In terms of hybridization conditions, the higher the sequence identity required, the more stringent are the hybridization conditions if such sequences are determined by their ability to hybridize to a sequence of SEQ ID NO:1. Accordingly, the invention also includes polynucleotides that are able to hybridize to at sequence comprising at least 20 contiguous nucleotides (or more, such as at least 25, 35, 40, 45, 50, 60, 75 or 100 contiguous nucleotides) of SEQ ID NO:1. The hybridization conditions would be stringent, i.e., 80° C. (or higher temperature) and 6M SSC (or less concentrated SSC). For discussion regarding hybridization reactions, see below.

The invention also includes an isolated polynucleotide comprising a sequence of at least 20 contiguous nucleotides (or more, such as 25, 35, 40, 45, 50, 60, 75, or 100 contiguous nucleotides) that hybridizes with a polynucleotide (such as DNA or RNA) having the sequence depicted in SEQ ID NO:1 under conditions where it does not hybridize from other polynucleotides from a mammalian cell, preferably a human cell. These embodiments are particularly useful in the diagnostic (detection) context.

In another embodiment, the invention includes a polynucleotide sequence comprising at least 15, preferably 20, more preferably 25, more preferably 35, more preferably 50, still more preferably 75 contiguous nucleotides of the non-coding (i.e., flanking) regions of SEQ ID NO:1. These embodiments may be particularly useful as diagnostic probes.

Hybridization reactions can be performed under conditions of different "stringency". Conditions that increase stringency of a hybridization reaction of widely known and published in the art. See, for example, Sambrook et al. (1989). Examples of relevant conditions include (in order of increasing stringency): incubation temperatures of 25° C., 37° C., 50° C. and 68° C.; buffer concentrations of 10×SSC, 6×SSC, 1×SSC, 0.1×SSC (where SSC is 0.15 M NaCl and 15 mM citrate buffer) and their equivalents using other buffer systems; formamide concentrations of 0%, 25%, 50%, and 75%; incubation times from 5 minutes to 24 hours; 1, 2, or more washing steps; wash incubation times of 1, 2, or 15 minutes; and wash solutions of 6×SSC, 1×SSC, 0.1×SSC, or deionized water. "$T_m$" is the temperature in degrees Centigrade at which 50% of a polynucleotide duplex made of complementary strands hydrogen bonded in antiparallel direction by Watson-Crick base pairing dissociates into single strands under conditions of the experiment. $T_m$ may be predicted according to a standard formula, such as:

$$T_m = 81.5 + 16.6 \log[X^+] + 0.41 (\%G/C) - 0.61 (\%F) - 600/L$$

where [$X^+$] is the cation concentration (usually sodium ion, $Na^+$) in mol/L; (%G/C) is the number of G and C residues as a percentage of total residues in the duplex; (%F) is the percent formamide in solution (wt/vol); and L is the number of nucleotides in each strand of the duplex.

Compositions containing TUP1 polynucleotides are encompassed by this invention. The invention also provides compositions comprising a vector(s) containing a TUP1 polynucleotide as well as compositions comprising a host cell containing a TUP1 polynucleotide, as described herein. When these compositions are to be used pharmaceutically, they are combined with a pharmaceutically acceptable excipient. Examples of pharmaceutically acceptable excipients are known in the art. When these compositions are to be used for detection, they are combined with a suitable substance such as a buffer, and they contain an amount effective to allow detection.

Preparation of TUP1 Polynucleotides

The polynucleotides of this invention can be obtained using chemical synthesis, recombinant methods, or PCR.

Methods of chemical polynucleotide synthesis are well known in the art and need not be described in detail herein. One of skill in the art can use the sequences provided herein and a commercial DNA synthesizer to produce a desired DNA sequence.

For preparing TUP1 polynucleotides using recombinant methods, a polynucleotide comprising a desired sequence can be inserted into a suitable vector, and the vector in turn can be introduced into a suitable host cell for replication and amplification. Polynucleotides may be inserted into host cells by any means known in the art. Cells are transformed by introducing an exogenous polynucleotide by direct uptake, endocytosis, transfection, F-mating or electroporation. Once introduced, the exogenous polynucleotide can be maintained within the cell as a non-integrated vector (such as a plasmid) or integrated into the host cell genome. The polynucleotide so amplified can be isolated from the host cell by methods well known within the art. See, e.g., Sambrook et al. (1989).

Alternatively, PCR allows reproduction of DNA sequences. PCR technology is well known in the art and is described in U.S. Pat. Nos. 4,683,195, 4,800,159, 4,754,065 and 4,683,202, as well as PCR: *The Polymerase Chain Reaction*, Mullis et al. eds., Birkauswer Press, Boston (1994).

RNA can be obtained by using the isolated DNA in an appropriate vector and inserting it into a suitable host cell. When the cell replicates and the DNA is transcribed into RNA, the RNA can then be isolated using methods well known to those of skill in the art, as set forth in Sambrook et al., (1989), for example.

If used as a vaccine (i.e., pharmaceutical composition for eliciting an immune response), plasmids containing TUP1 polynucleotides are preferably prepared as described by Horn et al. ((1995) *Human Gene Therapy* 6:565–573) which produces a pharmaceutical grade plasmid DNA suitable for administration.

Cloning and Expression Vectors Comprising a TUP1 Polynucleotide

The present invention further includes a variety of vectors (i.e., cloning and expression vectors) having cloned therein TUP1 polynucleotide(s). These vectors can be used for expression of recombinant polypeptides as well as a source of TUP1 polynucleotides. Cloning vectors can be used to obtain replicate copies of the TUP1 polynucleotides they contain, or as a means of storing the polynucleotides in a depository for future recovery. Expression vectors (and host cells containing these expression vectors) can be used to obtain polypeptides produced from the polynucleotides they contain. They may also be used where it is desirable to express Tup 1 polypeptides in an individual, such as for eliciting an immune response via the polypeptide(s) encoded in the expression vector(s). Suitable cloning and expression vectors include any known in the art, e.g., those for use in bacterial, mammalian, yeast and insect expression systems. Specific vectors and suitable host cells are known in the art and need not be described in detail herein. For example, see Gacesa and Ramji, Vectors, John Wiley & Sons (1994).

Cloning and expression vectors typically contain a selectable marker (for example, a gene encoding a protein necessary for the survival or growth of a host cell transformed with the vector), although such a marker gene can be carried on another polynucleotide sequence co-introduced into the host cell. Only those host cells into which a selectable gene has been introduced will survive and/or grow under selective conditions. Typical selection genes encode protein(s) that (a) confer resistance to antibiotics or other toxins substances, e.g., ampicillin, neomycyin, methotrexate, etc.; (b) complement auxotrophic deficiencies; or (c) supply critical nutrients not available from complex media. The choice of the proper marker gene will depend on the host cell, and appropriate genes for different hosts are known in the art. Cloning and expression vectors also typically contain a replication system recognized by the host.

Suitable cloning vectors may be constructed according to standard techniques, or may be selected from a large number of cloning vectors available in the art. While the cloning vector selected may vary according to the host cell intended to be used, useful cloning vectors will generally have the ability to self-replicate, may possess a single target for a particular restriction endonuclease, and/or may carry genes for a marker that can be used in selecting clones containing the vector. Suitable examples include plasmids and bacterial viruses, e.g., pUC18, pUC19, Bluescript (e.g., pBS SK+) and its derivatives, mp18, mp19, pBR322, pMB9, ColE1, pCR1, RP4, phage DNAs, and shuttle vectors such as pSA3 and pAT28. These and many other cloning vectors are available from commercial vendors such as BioRad, Strategene, and Invitrogen. The Examples provided herein also provide examples of cloning vectors.

Expression vectors generally are replicable polynucleotide constructs that contain a polynucleotide encoding a Tup1 polypeptide of interest. The polynucleotide encoding the Tup1 polypeptide is operatively linked to suitable transcriptional controlling elements, such as promoters, enhancers and terminators. For expression (i.e., translation), one or more translational controlling elements are also usually required, such as ribosome binding sites, translation initiation sites, and stop codons. These controlling elements (transcriptional and translational) may be derived from TUP1 polynucleotides (i.e., the TUP1 gene), or they may be heterologous (i.e., derived from other genes and/or other organisms). A polynucleotide sequence encoding a signal peptide can also be included to allow a Tup1 polypeptide to cross and/or lodge in cell membranes or be secreted from the cell. A number of expression vectors suitable for expression in eukaryotic cells including yeast, avian, and mammalian cells are known in the art. The Examples provided herein contain a number of examples of expression vectors for yeast systems, particularly S. cerevisiae and C. albicans. For instance, pRD53 can be used for Gal-induced expression in S. cerevisiae. Other common vectors, such as YEp13 and the Sikorski series pRS303–306, 313–316, 423–426 can also be used. Vectors pDBV52 and pDBV53 are suitable for expression in C. albicans.

The vectors containing the polynucleotides of interest can be introduced into the host cell by any of a number of appropriate means, including electroporation, transfection employing calcium chloride, rubidium chloride, calcium phosphate, DEAE-dextran, or other substances; microprojectile bombardment; lipofection; and infection (where the vector is an infectious agent, such as vaccinia virus). The choice of means of introducing vectors or TUP1 polynucleotides will often depend on the host cell.

Host Cells Transformed with TUP1 Polynucleotides

Another embodiment of this invention are host cells transformed with (i.e., comprising) TUP1 polynucleotides and/or vectors having TUP1 polynucleotide(s) sequences, as described above. Both prokaryotic and eukaryotic host cells may be used. Prokaryotic hosts include bacterial cells, for example E. coli, B. subtilis and mycobacteria. E. coli cells are particularly useful for producing Tup1 polypeptides. Komachi et al. (1994) Genes Dev. 8: 2857–2867. Among eukaryotic hosts are yeast, insect, avian, plant and mammalian cells. Host systems are known in the art and need not be described in detail herein. Examples of fungi (including yeast) host cells are S. cerevisiae, Kluyveromyces lactis (K. lactis), species of Candida including C. albicans and C. glabrata, C. maltosa, C. utilis, C. stellatoidea, C. parapsilosis, C. tropicalus, Neurospora crassas, Aspergillus nidulans, Schizosaccharomyces pombe (S. pombe), Pichia pastoris, and Yarowia lipolytica.

The host cells of this invention can be used, inter alia, as repositories of TUP1 polynucleotides and/or vehicles for production of TUP1 polynucleotides and/or polypeptides.

Uses for and Methods Using TUP1 Polynucleotides

The polynucleotides of this invention have several uses. TUP1 polynucleotides are useful, for example, in expression systems for the recombinant production of TUP1 or TUP1 fragments. They are also useful as hybridization probes to assay for the presence of TUP1 polynucleotide (or related) sequences in a sample using methods well known to those in the art. Further, TUP1 polynucleotides are also useful as primers to effect amplification of desired polynucleotides. The TUP1 polynucleotides of this invention may also be useful as vaccines.

TUP1 polynucleotides of this invention can be used as primers for amplification of polynucleotides encoding TUP1 or a fragment thereof, such as in a polymerase chain reaction (PCR). PCR has been described above. The conditions for carrying out PCR reactions depend on the specificity desired, which in turn can be adjusted by the primer used and the reaction conditions. Such adjustments are known in the art and need not be discussed in detail herein.

The TUP1 polynucleotides of this invention can be used in expression systems to produce Tup1 polypeptides or recombinant forms of Tup1 polypeptides, which have enhanced, equivalent, or different, desirable properties. These recombinant forms are made by using routine methods in the art. Examples of recombinant forms of Tup1 polypeptides include, but are not limited to, fusion proteins. Fusion proteins may be used to regulate the expression of other genes in C. albicans or related fungi. Fusion proteins may also facilitate purification.

TUP1 polynucleotides may also be used in diagnostic (i.e., detection) and screening methods, described in more detail below. Further, TUP1 polynucleotide may be used to obtain other genes and gene products regulated by TUP1 or otherwise involved in a TUP1 pathway, as described below.

Polypeptides of the Invention

The present invention encompasses C. albicans Tup1 polypeptide sequences. The polypeptides may comprise any novel region (i.e., not disclosed in the public domain as of the filing date of the original application of this series) of SEQ ID NO: 2. The Tup1 polypeptides of this invention are identified and characterized by any of the following criteria: (a) ability to bind (interact with) another protein, particularly a protein involved in gene regulation; (b) ability to elicit a humoral and/or cellular immune response in an individual; (c) ability to elicit certain characteristic(s) that are associated with TUP1 function; (d) ability to regulate other genes. Unless specifically stated, the term "polypeptide(s)" shall include all polypeptide embodiments of this invention.

The polypeptides have a variety of uses, including their use as a diagnostic tool for detecting antibodies against C. albicans, their use in making antibodies that bind to these polypeptides, their use as an antigen for vaccines (i.e., pharmaceutical compositions that elicit an immune response in an individual), their use as an agent to screen pharmaceutical candidates (both in vitro and in vivo), their use in rational (i.e., structure-based) drug design, their use in isolating other gene(s) and gene product(s) that are regulated by TUP1, as well as other possible therapeutic uses (for example, if full-length Tup 1 exerts its action by binding to another protein, a Tup1 polypeptide that binds competitively to Tup1 could compromise TUP1 function as a competitive inhibitor and thus exert anti-fungal, preferably therapeutic, activity). The Tup1 polypeptides may also be used to identifying proteins especially those from C. albicans that bind (or interact physically) with Tup1 which could thus themselves be drug targets.

The amino acid sequence of full-length Tup1 is shown in SEQ ID NO:2 as well as FIG. 2. There is a 67% sequence identity to S. cerevisiae Tup1. Further, both proteins contain a series of WD40 repeats, as discussed above. Komachi et al. (1994).

In one embodiment, the invention includes an isolated polypeptide comprising a Tup1 polypeptide from *C. albicans*, wherein the polypeptide complements a tup1 mutation in a yeast cell. The yeast cell may be any yeast cell which normally contains a TUP1 gene, such as *S. cerevisiae*, *C. albicans*, and other yeast cells that have been listed herein.

Complementation of a tup1 mutation has been described above and likewise applies in this context. Briefly, complementation may be to any function of TUP1 (which depends upon the cell under consideration), such as repression of certain genes, certain growth characteristics, certain infectivity characteristics (in the case of *C. albicans* in particular), and certain other phenotypes. Accordingly, the invention includes complementation as evidenced by any one of the characteristics associated with TUP1 function, such as repression of a gene that is regulated by TUP1, reduction of filamentous growth (in the case of *C. albicans*), and increase in virulence (in the case of *C. albicans*). These are representative examples only, as it is known that TUP1 exerts function on a number of levels, as described herein.

In another embodiment, the invention provides polypeptides which comprise at least one WD40 repeat (FIG. 2). Accordingly, the invention includes the following: (a) a polypeptide comprising the sequence between about 190 to about 228; about 254 to about 285; about 285 to about 328; about 328 to about 369; about 375 to about 417; about 425 to about 465; or about 465 to about 510 of SEQ ID NO:2; (b) a polypeptide comprising the sequence between about amino acid 190 to about 465 of SEQ ID NO:2; (c) a polypeptide comprising the sequence from about amino acid 190 to about amino acid 510 of SEQ ID NO:2.

In another embodiment, the Tup1 polypeptide referred to above comprises about amino acid 1 to about amino acid 465 of SEQ ID NO:2. In another embodiment, the complementing Tup1 polypeptide comprises about amino acid 190 to about 465 of SEQ ID NO:1. In another embodiment, the complementing Tup1 polypeptide comprises the sequence of SEQ ID NO:2.

The size of the Tup1 polypeptide fragments may vary widely, as the length required to effect activity could be as small as, for example, a 5-mer amino acid sequence to effect an immune response, or a 30-mer to 40-mer amino acid sequence to effect binding via a WD40 repeat region. The maximum length generally is not detrimental to effecting activity. The minimum size must be sufficient to provide a desired function. Thus, the invention includes polypeptide fragments of full-length Tup1 comprising a portion of the amino acid sequence depicted in SEQ ID NO:2 in which the Tup1 polypeptide is about 15, preferably 25, more preferably 50 more preferably 75, more preferably 100, more preferably 150, amino acids in length. As is evident to one skilled in the art, these Tup 1 polypeptides, regardless of their size, may also be associated with, or conjugated with, other substances or agents to facilitate, enhance, or modulate function and/or specificity of a Tup1 polypeptide.

The invention includes modifications to Tup1 polypeptides including functionally equivalent fragments of the Tup1 polypeptides which do not significantly affect their properties and variants which have enhanced or decreased activity, provided that these sequences are different from that of *S. cerevisiae* Tup 1. Modification of polypeptides is routine practice in the art and need not be described in detail herein. Examples of modified polypeptides include polypeptides with conservative substitutions of amino acid residues, one or more deletions or additions of amino acids which do not significantly deleteriously change the functional activity, or use of chemical analogs. Amino acid residues which can be conservatively substituted for one another include but are not limited to: glycine/alanine; valine/isoleucine/leucine; asparagine/glutamine; aspartic acid/glutamic acid; serine/threonine; lysine/arginine; and phenylalanine/tryosine. These polypeptides also include glycosylated and nonglycosylated polypeptides, as well as polypeptides with other post-translational modifications, such as, for example, glycosylation with different sugars, acetylation, and phosphorylation. Preferably, the amino acid substitutions would be conservative, i.e., the substituted amino acid would possess similar chemical properties as that of the original amino acid. Such conservative substitutions are known in the art, and examples have been provided above. Amino acid modifications can range from changing or modifying one or more amino acids to complete redesign of a region, such as the variable region. Changes in the variable region can alter binding affinity and/or specificity. Other methods of modification include using coupling techniques known in the art, including, but not limited to, enzymatic means, oxidative substitution and chelation. Modifications can be used, for example, for attachment of labels for immunoassay, such as the attachment of radioactive moieties for radioimmunoassay. Modified Tup1 polypeptides are made using established procedures in the art and can be screened using standard assays known in the art.

The invention also encompasses fusion proteins comprising one or more Tup1 polypeptides. For purposes of this invention, a Tup1 fusion protein contains one or more Tup1 polypeptides and another amino acid sequence to which it is not attached in the native molecule, for example, a heterologous sequence or a homologous sequence from another region. Useful heterologous sequences include, but are not limited to, sequences that provide for secretion from a host cell, enhance immunological reactivity, or facilitate the coupling of the polypeptide to an immunoassay support or a vaccine carrier. For instance, a Tup1 polypeptide can be fused with a bioresponse modifier. Examples of bioresponse modifiers include, but are not limited to, cytokines or lymphokines such as GM-CSF, interleukin-2 (IL-2), interleukin 4 (IL-4), and γ-interferon. Accordingly, the invention includes Tup1 fusion polypeptides that contain GM-CSF or IL-2. Another useful heterologous sequence is one which facilitates purification. Examples of such sequences are known in the art and include those encoding epitopes such as Myc, HA (derived from influenza virus hemagglutinin), His-6, or FLAG. Other heterologous sequences that facilitate purification are derived from proteins such as glutathione S-transferase (GST), maltose-binding protein (MBP), or the Fc portion of immunoglobulin.

The invention also encompasses polymeric forms of Tup1 polypeptides, preferably full-length Tup1 polypeptides. As used herein, a polymeric form of a Tup1 polypeptide contains a plurality (i.e., more than one) of Tup1 polypeptides. In one embodiment, linear polymers of Tup1 polypeptides are provided. These Tup1 linear polymers may be conjugated to carrier. These linear polymers can comprise multiple copies of a single Tup1 polypeptide, or combinations of different Tup1 polypeptides, and can have tandem Tup1 polypeptides, or Tup1 polypeptides separated by other amino acid sequences. These linear polymers can be made using standard recombinant methods well known in the art. In another embodiment, Tup1 multiple antigen peptides Maps) are provided. Maps have a small immunologically inert core having radically branching lysine dendrites, onto which a number of Tup1 polypeptides can be anchored (i.e., covalently attached). Posnett et al. (1988) *J. Biol. Chem.* 263:1719–1725; Tam (1989) *Meth. Enz.* 168:7–15. The result is a large macromolecule having a high molar ratio of Tup1 polypeptides to core. maps are useful, efficient immunogens as well as useful antigens for assays such as ELISA. Tup1 maps can be made synthetically and can be obtained commercially (Quality Controlled Biochemicals, Inc. Hopkinton, Mass.). In a typical MAP system, a core matrix is made up of three levels of lysine and eight amino acids for anchoring Tup1 polypeptides. The MAP may be synthesized by any method known in the art, for example. a solid-phase method, for example, R. B. Merrifield (1963) *J. Am. Chem. Soc.* 85:2149.

In another embodiment, Tup1 polypeptides can be conjugated with carrier or label. For example, in instances where the Tup1 polypeptide is correctly configured so as to provide a binding site, but is too small to be immunogenic, the polypeptide may be linked to a suitable carrier. A number of techniques for obtaining such linkage are known in the art and need not be described in detail herein. Any carrier can be used which does not itself induce the production of antibodies harmful to the host. Suitable carriers are typically large, slowly metabolized macromolecules such as proteins; polysaccharides, such as latex functionalized sepharose, agarose, cellulose, cellulose beads and the like; polymeric amino acids, such as polyglutamic acid, polylysine, and the like; amino acid copolymers; and inactive virus particles or attenuated bacteria, such as Salmonella. Especially useful protein substrates are serum albumins, keyhole limpet hemacyanin, immunoglobulin molecules, thyroglobulin, ovalbumin, tetanus toxoid, and other proteins well known to those of skill in the art. Labels are known in the art and are described herein.

Tup1 polypeptides of the invention can be identified and/or characterized in a number of ways. For example, a Tup1 polypeptide can be tested for its ability to bind to, for instance, another protein (such as an antibody or a protein associated with gene regulation by interacting with full-length Tup1). Alternatively, Tup1 polypeptide(s) can be tested for its ability to elicit an immune response, whether humoral or cellular. A Tup1 polypeptide may also be tested for its ability to elicit one or more characteristics associated with TUP1 function, including the ability to complement loss of TUP1 function in an organism such as *C. albicans*, *S. cerevisiae*, *K. lactis*, or any other organism known to exhibit TUP1 function. It is understood that only one of these properties need be present in order for a polypeptide to come within this invention, although more than one of these properties may be present. See, e.g., Example 2. Screening such polypeptides is well within the skill of the art.

The ability of a Tup1 polypeptide to bind (i.e., interact with) another protein can be assessed using standard techniques in the art. Binding of a Tup1 polypeptide to an antibody may be assessed, for example, by RIA (i.e., by reacting radiolabelled Tup1 polypeptide with an antibody that is coated on microtiter plates). In another procedure, binding to an antibody is determined by competitive immunoassay. For example, a fragment is tested for its ability to interfere with the binding between the antibody and another polypeptide known to bind to the antibody. This assay may be conducted by labeling one of the components (i.e., antibody or polypeptide known to bind to the antibody), and optionally immobilizing the other member of the binding pair on a solid support for ease of separation. The test fragment is incubated with labeled region, and then the mixture is presented to the immobilized target to determine if the test fragment is able to inhibit binding.

In the case of testing whether the Tup1 polypeptide binds to another protein, for instance, a protein known to be involved in a TUP1 pathway, or a protein known to bind to Tup1, assays to detect binding are known in the art and need not be described in detail herein. For instance, a protein is immobilized on a suitable column. Extracts or solutions containing the test Tup1 polypeptide are then run through the column, and a determination is made whether the Tup1 polypeptide was retained on the column. Conversely, the Tup1 polypeptides can be immobilized on a column and cell extracts or lysates are allowed to run through the column.

For characterizing a Tup1 polypeptide for its ability to complement *S. cerevisiae* TUP1 function (i.e., substitute for *S. cerevisiae* Tup1), a candidate Tup1 polypeptide is tested for its ability to exhibit an activity associated with *S. cerevisiae* TUP1 expression. For instance, a Tup1 polypeptide may be tested for its ability to bind to SSN6. Redd et al. (1997) *J. Biol. Chem.* 272: 11193–11197. As another example, a Tup1 polypeptide may be tested for its ability to restore TUP1 function in an *S. cerevisiae* cell that lacks TUP1 function due to, for example, genetic manipulation (Example 3). For these assays, a polynucleotide encoding the Tup1 polypeptide of interest is introduced into an *S. cerevisiae* cell lacking TUP1 function (tup1). The transformed cell is analyzed for any characteristic that is associated with TUP1 function, including, but not limited to, repression of TUP1-regulated genes, non-flocculence, non-temperature sensitivity (at 37° C.), wild type cell shape, and rapid (normal) growth. An experiment in which a deletion of the COOH region of *C. albicans* full-length Tup1 is discussed in Example 3.

For characterizing a Tup1 polypeptide by testing its ability to complement *C. albicans* TUP1 function in *C. albicans*, a Tup1 polypeptide assayed for its ability to confer at least one characteristic associated with *C. albicans* TUP1 function, such as filamentous formation under conditions that otherwise promote blastophore growth, growth at 42° C., slower growth rate on glycerol, increased infectivity compared to *C. albicans* cells with compromised TUP1 function, as well as any other characteristics that are discovered. As an example, a polynucleotide encoding a Tup1 polypeptide of interest is introduced into a *C. albicans* cell which has compromised TUP1 function (see description of such cells and how to make such cells below), and the cell is assayed for any one or more of the above characteristics. Further, as an adjunct to the above-described tests in *S. cerevisiae*, a Tup1 polypeptide that has exhibited an ability to complement *S. cerevisiae* TUP1 function (i.e., substitute for *S. cerevisiae* Tup1), may then be tested in *C. albicans*. Reporter (such as lacZ) or non-reporter (assayable to RT-PCR)gene systems may be used to evaluate an ability to de-repress genes. Such systems are known in the art.

For characterizing a Tup1 polypeptide for its ability to elicit an immune response (whether humoral or cellular) in an individual, standard assays exist in the art. For instance, the ability of a Tup1 polypeptide to generate a humoral response can be determined by testing for the presence of an antibody that binds to the Tup1 polypeptide(s) after administration of the Tup1 polypeptide(s). It is understood that this antibody was not present, or was present in lower amounts, before administration of the Tup1 polypeptide(s). Immunogenicity is preferably tested in individuals without a previous anti-Tup1 response. Examples of suitable individual include, but are not limited to, mice, rats, rabbits, goats, monkeys and humans. For this test, an individual is administered a Tup1-polypeptide(s). The amount per administration and the number of administrations will vary, depending on the individual. Presence of an antibody elicited in response to administration of a Tup1 polypeptide(s) is determined by standard assays in the art, such as ELISA or RIA. Tup1 polypeptide(s) may be further characterized by their ability to elicit an antibody that is cytotoxic, or to elicit an antibody that participates in an ADCC response using standard assays in the art.

A Tup1 polypeptide can also be characterized by its ability to elicit a cellular immune response, using, for example, assays that detect proliferation of peripheral blood mononuclear cells (PBMs) incubated with a Tup1 polynucleotide. Another way of detecting a cellular immune response is to test for T cell cytotoxicity (CTL) activity. Both of these responses are detected using standard assays in the art.

Compositions containing TUP1 polypeptides are encompassed by this invention. When these compositions are to be used pharmaceutically, they are combined with a pharmaceutically acceptable excipient. Examples of pharmaceutically acceptable excipients are known in the art. When these compositions are to be used for detection, they are combined with a suitable substance such as a buffer, and they contain an amount effective to allow detection.

Preparation of Polypeptides of this Invention

The polypeptides of this invention can be made by procedures known in the art. The polypeptides can be produced by recombinant methods (i.e., single or fusion polypeptides) or by chemical synthesis. Polypeptides, especially shorter polypeptides up to about 50 amino acids, are conveniently made by chemical synthesis. Methods of chemical synthesis are known in the art and are commercially available. For example, a polypeptide could be produced by an automated polypeptide synthesizer employing the solid phase method. Polypeptides can also be made by chemical synthesis using techniques known in the art.

Polypeptides can also be made by expression systems, using recombinant methods. The availability of polynucleotides encoding polypeptides permits the construction of expression vectors encoding intact (i.e., native) polypeptide, functionally equivalent fragments thereof, or recombinant forms. A polynucleotide encoding the desired polypeptide, whether in fused or mature form, and whether or not containing a signal sequence to permit secretion, may be ligated into expression vectors suitable for any convenient host. Both eukaryotic and prokaryotic host systems can be used. The polypeptide is then isolated from lysed cells or from the culture medium and purified to the extent needed for its intended use. Purification or isolation of the polypeptides expressed in host systems can be accomplished by any method known in the art. For example, cDNA encoding a polypeptide intact or a fragment thereof can be operatively linked to a suitable promoter, inserted into an expression vector, and transfected into a suitable host cell. The host cell is then cultured under conditions that allow transcription and translation to occur, and the desired polypeptide is recovered. Other controlling transcription or translation segments, such as signal sequences that direct the polypeptide to a specific cell compartment (i.e., for secretion), can also be used. Examples of prokaryotic host cells are known in the art and include, for example, E. coli and B. subitilis. Examples of eukaryotic host cells are known in the art and include yeast, avian, insect, plant, and animal cells such as COS7, HeLa, CHO and other mammalian cells.

When using an expression system to produce Tup1 polypeptides, it is often preferable to construct a fusion protein that facilitates purification. Examples of components for these fusion proteins include, but are not limited to myc, HA, FLAG, His-6, glutathione S-transferease, maltose binding protein or the Fc portion of immunoglobulin. These methods are known in the art and some of them have been used successfully to isolate *S. cerevisiae* Tup1 and Tup1 fragments. Redd et al. (1997) *J. Biol. Chem.* 272:11193–11197.

Preferably, especially if used for diagnostic purposes, the polypeptides are at least partially purified or isolated from other cellular constituents. Preferably, the polypeptides are at least 50% pure. In this context, purity is calculated as a weight percent of the total protein content of the preparation. More preferably, the proteins are 50–75% pure. More highly purified polypeptides may also be obtained and are encompassed by the present invention. For clinical use, the polypeptides are preferably highly purified, at least about 80% pure, and free of pyrogens and other contaminants. Methods of protein purification are known in the art and are not described in detail herein.

Uses of Polypeptides

The polypeptides of this invention have a variety of uses. They can be used, for example, to detect the presence of an antibody that binds to these polypeptide(s) or fragment(s) thereof. They may also be used to raise antibodies in a suitable host, which may be rabbit, mouse, rat, goat, or human, as non-inclusive examples. It is possible that such antibodies, when present in humans, may confer some degree of protection or resistance against *C. albicans* pathogenesis, including initial infection and spread. It is also possible that these antibodies may provide a therapeutic function against *C. albicans* infection. The polypeptides of this invention thus may well prove to be useful in pharmaceutical applications, such as in therapeutic and/or prophylactic vaccines. Accordingly, the invention provides compositions comprising full-length Tup1 and/or Tup1 polypeptides and a pharmaceutically acceptable excipient, said compositions capable of eliciting an immune response in an individual when administered in an effective amount. In this context, an "effective amount" is an amount sufficient to elicit an immune response (whether humoral or cellular), and an effective amount may be administered in one or more administrations.

Tup1 polypeptides may also be used an agent to screen pharmaceutical candidates (both in vitro and in vivo), for rational (i.e., structure-based) drug design, as well as possible therapeutic uses as described above. Uses in pharmaceutical development will be described in more detail below. The Tup1 polypeptides may also be used to identifying proteins, especially those from *C. albicans* that bind (or interact physically) with Tup1 and could thus themselves be drug targets.

Antibodies and their Preparation

Also provided by this invention are antibodies capable of specifically binding to Tup1 polypeptide(s) of this invention. The antibodies can be useful for, for example, diagnostic purposes, as described more fully below. Antibodies of this invention can also be used for purification and/or isolation of polypeptides described herein.

In one embodiment, the invention provides a purified antibody capable of specifically binding to a polypeptide of this invention. As noted in the definition of "antibody" above, this includes fragments of antibodies, such as Fab fragments. In another embodiment, a monoclonal antibody is provided that is capable of specifically binding to a polypeptide of this invention.

Laboratory methods for producing polyclonal antibodies and monoclonal antibodies, as well as deducing their corresponding nucleic acid sequences, are known in the art. For example, see Harlow and Lane, *Antibodies: A Laboratory Manual*, Cold Spring Harbor Laboratory, New York (1988) and Sambrook et al. (1989).

The antibodies of this invention may be polyclonal or monoclonal. Monoclonal antibodies of this invention can be biologically produced by introducing a polypeptide (or fragment of a polypeptide) of this invention into an animal, e.g., mouse or rat. The antibody producing cells in the animal are isolated and fused with myeloma cells or heteromyeloma cells to produce hybrid cells or hybridomas. Accordingly, the invention also includes hybridoma cells producing the monoclonal antibodies of this invention.

Particular isotypes of a monoclonal antibody can be prepared either directly by selecting from the initial fusion, or prepared secondarily, from a parental hybridoma secreting a monoclonal antibody of different isotype by using the sib selection technique to isolate class switch variants using the procedure described in Steplewski et al. (1985) *Proc. Natl. Acad. Sci.* 82:8653 or Spira et al. (1984) *J. Immunol. Methods* 74:307.

Thus, using the polypeptide(s) of this invention or fragment(s) thereof, and well known methods, one of skill in the art can produce and screen the hybridoma cells and antibodies of this invention for antibodies having the ability to bind polypeptide(s) of this invention.

If a monoclonal antibody being tested binds with a Tup1 polypeptide(s) of this invention, then the antibody being tested and the antibodies provided by the hybridomas of this invention are equivalent. It is also possible to determine without undue experimentation whether an antibody has the same specificity as a monoclonal antibody of this invention by determining whether the antibody being tested prevents a monoclonal antibody of this invention from binding the polypeptide(s) with which the monoclonal antibody is normally reactive. If the antibody being tested competes with the monoclonal antibody of the invention as shown by a decrease in binding by the monoclonal antibody of this invention, then it is likely that the two antibodies bind to the same or a closely related epitope. Alternatively, one can pre-incubate the monoclonal antibody of this invention with the polypeptide(s) with which it is normally reactive, and determine if the monoclonal antibody being tested is inhibited in its ability to bind the antigen. If the monoclonal antibody being tested is inhibited, then, in all likelihood, it has the same, or a closely related, epitopic specificity as the monoclonal antibody of this invention.

As noted above, this invention also provides biological active fragments of the polyclonal and monoclonal antibodies described above. These antibody fragments retain some ability to selectively bind with its antigen or immunogen. Examples of antibody fragments are known in the art and include, but are not limited to, CDR regions, Fab, Fab', F(ab')$_2$, Fv, and single chain methods. Methods of making these fragments are known in the art, see for example, Harlow and Lane, (1988).

The antibodies of this invention also can be modified to create chimeric antibodies and humanized antibodies (Oi et al. (1986) *BioTechniques* 4(3):214). Chimeric antibodies are those in which the various domains of the antibodies' heavy and light chains are coded for by DNA from more than one species.

The isolation of other hybridomas secreting monoclonal antibodies with the specificity of the monoclonal antibodies of the invention can also be accomplished by one skilled in the art by producing anti-idiotypic antibodies (Herlyn, et al. (1986) *Science*, 232:100). An anti-idiotypic antibody is an antibody which recognizes unique determinants present on the monoclonal antibody produced by the hybridoma of interest. These determinants are located in the hypervariable region of the antibody. It is this region which binds to a given epitope and, thus, it is responsible for the specificity of the antibody. The anti-idiotypic antibody can be prepared by immunizing an animal with the monoclonal antibody of interest. The animal immunized will recognize and respond to the idiotypic determinants of the immunizing antibody by producing an antibody to these idiotypic determinants. By using the anti-idiotypic antibodies of the second animal, which are specific for the monoclonal antibodies produced by a single hybridoma which was used to immunize the second animal, it is now possible to identify other clones with similar idiotypes as the antibody of the hybridoma used for immunization.

Idiotypic identity between monoclonal antibodies of two hybridomas demonstrates that the two monoclonal antibodies are the same with respect to their recognition of the same epitopic determinant. Thus, by using antibodies to the epitopic determinants on a monoclonal antibody it is possible to identify other hybridomas expressing monoclonal antibodies of the same epitopic specificity.

It is also possible to use the anti-idiotype technology to produce monoclonal antibodies which mimic an epitope. For example, an anti-idiotypic monoclonal antibody made to a first monoclonal antibody will have a binding domain in the hypervariable region which is the mirror image of the epitope bound by the first monoclonal antibody. Thus, in this instance, the anti-idiotypic monoclonal antibody could be used for immunization for production of these antibodies.

The antibodies of this invention can be linked (i.e., conjugated) to a detectable agent or a hapten. The complex is useful to detect the polypeptide(s) (or polypeptide fragments) to which the antibody specifically binds in a sample, using standard immunochemical techniques such as immunohistochemistry as described by Harlow and Lane (1988). supra. Examples of types of immunoassays which can utilize monoclonal antibodies of the invention are competitive and non-competitive immunoassays in either a direct or indirect format. Examples of such immunoassays are the enzyme linked immunoassay (ELISA) radioimmunoassay (RIA) and the sandwich (immunometric) assay. Detection of using the monoclonal antibodies of the invention can be done by utilizing immunoassays which are run in either the forward, reverse, or simultaneous modes, including immunohistochemical assays on physiological samples. Those of skill in the art will know, or can readily discern, other immunoassay formats without undue experimentation.

Another technique which may also result in greater sensitivity consists of coupling the antibodies to low molecular weight haptens. These haptens can then be specifically detected by means of a second reaction. For example, it is common to use such haptens as biotin, which reacts avidin, or dinitropherryl, pyridoxal, and fluorescein, which can react with specific anti-hapten antibodies. See Harlow and Lane (1988) supra.

The monoclonal antibodies of the invention can be bound to many different carriers. Thus, this invention also provides compositions containing antibodies and a carrier. Carriers can be active and/or inert. Examples of well-known carriers include glass, polystyrene, polypropylene, polyethylene, dextran, nylon, amylases, natural and modified celluloses, polyacrylamides, agaroses and magnetite. The nature of the carrier can be either soluble or insoluble for purposes of the invention. Those skilled in the art will know of other suitable carriers for binding monoclonal antibodies, or will be able to ascertain such, using routine experimentation.

There are many different labels and methods of labeling known to those of ordinary skill in the art. Examples of the types of labels which can be used in the present invention include enzymes, radioisotopes, fluorescent compounds, colloidal metals, chemiluminescent compounds, and bioluminescent compounds. Those of ordinary skill in the art will know of other suitable labels for binding to the monoclonal antibody, or will be able to ascertain such, using routine experimentation. Furthermore, the binding of these labels to the monoclonal antibody of the invention can be done using standard techniques common to those of ordinary skill in the art.

For purposes of the invention, polypeptides of this invention may be detected by the monoclonal antibodies of the invention when present in biological samples, such as fluids and tissues. This use of antibodies is discussed in more detail below.

Compositions containing the antibodies, fragments thereof or cell lines which produce the antibodies, are encompassed by this invention. When these compositions are to be used pharmaceutically, they are combined with a pharmaceutically acceptable excipient.

*Candida albicans* Cells Having Compromised TUP1 Function

The invention also provides isolated *C. albicans* cells in which TUP1 function is compromised. As noted above in the definition of "compromise" of TUP1 function, it is understood that compromise of TUP1 function also includes, but is not limited to, complete loss of TUP1 function (i.e., knockout). Because *C. albicans* is diploid, compromise of TUP1 function may be effected by compromising TUP1 function in either or both TUP1 genes. These cells are useful for providing a known standard for compromise of TUP1 function. Such a standard may be used for comparative purposes when employing the screening methods described herein. Further, because the tup1 knockout cell has low infectivity and thus may be viewed as "inactivated", it is possible that such a cell could be used to elicit an immune response by administration of an amount effective to generate an immune response in an individual. Because these cells are constitutively making all of the hyphal surface proteins, it is possible that antibodies against the filamentous form will be elicited without a significant concomitant risk of infection. As used herein, an "effective amount" can be administered in one or more than one dose. Accordingly, the invention also provides compositions of these cells, including compositions comprising these cells and a pharmaceutical excipient, as well pharmaceutical compositions comprising these cells. Pharmaceutical excipients are well known in the art and need not be described in detail herein. See, for example, *Remington: The Science and Practice of Pharmacy* (19th edition, 1995), Gennaro, ed.

In some embodiments, compromise of TUP1 function is due to alteration at the DNA level. In one embodiment, compromise of TUP1 function is due to disruption of a single TUP1 gene (i.e., heterozygous), as described in Example 3. In another embodiment, compromise of TUP1 function is due to disruption of both TUP1 genes (i.e., homozygous knockout), as described in Example 3. In another embodiment, disruption of TUP1 is due to site-directed mutagenesis in which the resultant amino acid sequence of Tup1 is altered. In other embodiments, compromise of TUP1 function is due to alteration of function on, for example, the level of transcription (such as anti-sense). "Anti-sense" as used herein refers to a nucleic acid capable of hybridizing to a portion of a TUP1 RNA (preferably MRNA) by virtue of some sequence complementarity.

Generally, these cells also contain a selectable marker, such as URA and others described herein. A selectable marker encodes a protein that, for example, confers drug resistance or complements an auxotrophy.

Methods for making such cells, and including techniques for making appropriate genetic manipulations, are known in the art. See, for example, Sherer et al. (1990) Microb. Rev. 54:226–241 and Example 3.

Methods Using TUP1 Polynucleotides, Polypeptides and Antibodies: Detection Systems The invention also provides methods using the TUP1 polynucleotides, polypeptides, and/or antibodies of the invention to detect suitable targets in a biological sample. Procedures for conducting diagnostic (i.e., detection) tests using polynucleotides, polypeptides or antibodies are extensively known in the art and are routine for a practitioner or ordinary skill. Generally, to perform a diagnostic method of this invention, one of the compositions of this invention is provided as a reagent to detect a target with which it reacts in a biological sample. The target is supplied by obtaining a suitable biological sample from an individual for whom the diagnostic parameter is to be measured. Many types of samples are suitable for this purpose, including those that are obtained at or near the suspected site of infection. If desired, the target may be partially purified from the sample or amplified before the assay is conducted.

Presently, diagnostic methods for *C. albicans* are cumbersome, requiring culturing and microscopic examination for germ tube formation. See, for example, Warren et al. (1991) *Manual of Clin. Micro* (5th ed.) at 617–629. Thus, the invention includes methods for detecting a polynucleotide from *C. albicans* in a sample comprising the steps of contacting a polynucleotide from *C. albicans* in a sample with any of the polynucleotides of this invention under conditions that permit formation of a stable duplex and detecting the stable duplex formed, if any.

For patients already diagnosed with *C. albicans* infection, detection of these sequences may assist with clinical management. For example, presence of a sequence particularly associated with an aspect of infection, such as aggressiveness or anti-fungal drug resistance, may be a useful predictor of susceptibility to various regimens of standard therapy, the extent of disease, and/or its aggressiveness. Any or all of these determinations can be important in helping a clinician choose and adjust available treatment options.

Polynucleotides

TUP1 polynucleotides can also be used as hybridization probes for detection of, for example, the presence of TUP1 polynucleotides in a cell. For instance, a TUP1 polynucleotide could be used as a probe to determine the presence of *C. albicans* polynucleotide sequences in cells suspected of being infected by *C. albicans*. Accordingly, the invention provides methods for detecting a polynucleotide from *C. albicans* in a biological sample comprising the steps of (a)

contacting the polynucleotide from *C. albicans* from the sample with a polynucletoide of this invention under conditions that permit the formation of a stable duplex and (b) detecting the stable duplex. formed in step (a), if any. In another embodiment, the invention provides methods for detecting a polynucleotide from *C. albicans* in a biological sample comprising the steps of (a) conducting an amplification reaction on a polynucleotide in the sample using a primer consisting of a fragment of the polynucletoide sequence of SEQ ID NO:1 and (b) detecting the presence of amplified copies of the polynucletoide, if any.

For these methods, a suitable cell sample or a sample derived from cells (either of which are suspected of containing TUP1 polynucleotide sequences) is obtained and tested for the presence of TUP1 polynucleotide by contacting the polynucleotides from the sample with the TUP1 polynucleotide probe. The method is conducted to allow hybridization to occur between the TUP1 probe and TUP1 polynucleotide of interest, and the resultant (if any) hybridized complex is detected. Such methods entail procedures well known in the art, such as cell culture, polynucleotide preparation, hybridization, and detection of hybrid complexes formed, if any. Using similar methods, the probes can also be used to detect vectors which are in turn used to produce TUP1 polypeptides, intact TUP1, or recombinant, variant forms of TUP1.

The reaction is performed by contacting a TUP1 polynucleotide under conditions that will allow a stable complex to form between the TUP1 polynucleotide and a polynucleotide target. Complex formation is detected by a number of techniques known in the art.

The assay result is preferably compared with a similar assay conducted on a control sample, preferably a sample from an uninfected source (negative control). It is often preferable to conduct the assay on the test sample and control sample simultaneously.

These diagnostic assays may be rendered specific by, for example (a) performing a hybridization reaction with a specific probe; (b) performing an amplification with a specific primer; or (c) combination of (a) and (b). To perform an assay that is specific due to hybridization with a specific probe, a polynucletoide is chosen with the required degree of complementarity for the intended target polynucleotide. Preferred probes include polynucletoides of at least about 15 nucleotides in length. These probes may contain the coding or non-coding sequence of TUP1. Increasingly preferred are probes comprising at least about 20, 25, 30, 50 or 100 polynucleotides.

The probe may be provided with a label. Some of the labels often used include radioisotopes such as $^{32}$P and $^{33}$P, chemiluminscent or fluorescent reagents such as fluorescein, and enzymes such as alkaline phosphatase that are capable of producing a colored solute or precipitant. The label may be intrinsic to the reagent, it may be attached by direct chemical linkage, or it may be connected through a series of intermediate reactive molecules, such as a biotin-avidin complex, or a series of inter-reactive polynucleotides. The label may be added to the reagent before hybridization with the target polynucleotide, or afterwards. To improve the sensitivity of the assay, it is often desirable to increase the signal ensuing from hybridization. This can be accomplished by using a combination of serially hybridizing polynucleotides or branched polynucleotides in such a way that multiple label components become incorporated into each complex. See U.S. Pat. No. 5,124,426.

If desired, the target polynucleotide may be extracted from the sample, and may also be partially purified. The target polynucleotide may be optionally subjected to any combination of additional treatments, including digestion with restriction endonucleases, size separation (by electrophoresis in agarose or polyacrylamide, for example), and affixation to a reaction matrix, such as a blotting material.

Hybridization is allowed to occur by mixing the TUP1 polynucleotide with a sample suspected of containing target polynucleotide under appropriate reaction conditions. This may be followed by washing or separation to remove unreacted reagent. Generally, both target polynucleotide and TUP1 polynucleotide are at least partly equilibrated into the single-stranded form (i.e., denatured) in order for complementary sequences to hybridize efficiently.

The level of hybridization stringency depends, inter alia, upon the objective of the test and the particular TUP1 polynucleotide used. For example, a preferred set of conditions for used with a preferred probe of 50 nucleotides or more is 6×SSC at 37° C. in 50% formamide, followed by a wash at low ionic strength. This will generally require that the polynucleotide target be at least about 90% identical with the TUP1 polynucleotide for a stable duplex to form. The specificity of the reaction may also be increased by increasing the length of the TUP1 polynucleotide used.

Appropriate hybridization conditions are determined to permit hybridization of the probe only to *C. albicans* sequences. Conditions may be estimated beforehand using the formula given above. Preferably, the exact conditions are confirmed by testing the TUP1 polynucleotide with separate samples known to contain target *C. albicans* polynucleotides as well as polynucleotides that are not desired to be detected. Such samples may be provided either by synthesizing the polynucleotides from published sequences, or by extracting and amplifying DNA from tissues known to be infected with *C. albicans*. Preferably, probes share little to no sequence homology with human sequences. However, even if there are shared sequences, such a probe may still be useful if detection systems allow discrimination between signal due to hybridization to *C. albicans* sequences and signal due to hybridization to human sequences. If it is additionally desirable to distinguish between and/or among various Candida species, the probe (due to length and/or sequence content) and/or hybridization conditions should be adjusted and selected such that these sequences may be distinguished.

Another method of detecting polynucleotide target is by using PCR. All processes of producing replicate copies of the same polynucleotide, such as PCR or gene cloning, are collectively referred to herein as "replication". PCR primers consisting of sequences unique to TUP1 may be used to amplify any such sequences in the sample. Preferably, a sample known not to contain any *C. albicans* sequences is used as a negative control. PCR methods are well known in the art and need not be described herein. For these methods, DNA or RNA is prepared from a sample. Optionally, target polynucleotide is pre-amplified by PCR using primers which are specific to Candida, preferably *C. albicans*. The target is then amplified using TUP1-specific primers. Preferably, two rounds of amplification are performed using oligonucleotide primers in a nested fashion, i.e., non-specific in the first round followed by *C. albicans* in the second round. This provides an assay which is both sensitive and specific.

The primers used consist of fragments of SEQ ID NO:1. Preferably, at least one, preferably both, of the primers are sequences unique to *C. albicans*. Alternatively, if the expected size of the amplified *C. albicans* reaction product is known and different from that of the non-target (for example, host) polynucleotides, the sequences of the primers need not be unique. Generally, the primer is about 15 to 20 nucleotides in length, although longer primer of 30 to 50 nucleotides may be used.

A positive test may be indicated by the presence of sufficient reaction product at the end of the amplification series. Amplified polynucleotide may be detected on an agrose gel upon staining with ethidium bromide. Alternatively, a radiolabeled substrate may be added to the mixture during the final amplification cycle. The incorporated label may be separated from unincorporated label (e.g., by blotting or by size separation) and the label may be detected by, for example, counting or autoradiography. If run on a gel of agarose or polyacrylamide,. the size of the product may help confirm the identify of the amplified fragment. Specific amplification may also be followed by specific hybridization, by using the amplification mixture obtained from the foregoing procedure as a target source for the hybridization reaction outlined above.

Polypeptides

A polypeptide embodied in this invention can also be used as a reagent for determining $C.\ albicans$ that may be present via the detection of antibodies that specifically bind to Tup1 polypeptides of this invention. For example, $C.\ albicans$ DNA and/or RNA in affected cells may result in the corresponding polypeptide(s) being produced by the cells. This in turn may result in stimulation of the immune response of the host to produce its own antibody molecules that are specific for the polypeptide(s).

Accordingly, the invention includes methods for detecting an anti-$Candida\ albicans$ antibody in a biological samples, in which the steps are (a) contacting antibody from the sample with a Tup1 polypeptide (i.e., a polypeptide of this invention) under conditions which permit formation of a stable antigen-antibody complex, and (b) detecting stable complex formed, if any.

To use the polypeptide(s) of this invention in the detection of such antibodies in an individual suspected of having $C.\ albicans$ infection, an immunoassay is conducted. The polypeptide(s) is provided as a reagent, and the antibody is the target in the biological sample. For example, human IgG antibody molecules present in a serum sample may be captured with solid-phase protein A, and then overlaid with the labeled polypeptide reagent. The amount of antibody would then be proportional to the label attached to the solid phase. Alternatively, cells or tissue sections expressing the polypeptide may be overlaid first with the test sample containing the antibody, and then with a detecting reagent such as labeled anti-immunoglobulin. The amount of antibody would then be proportional to the label attached to the cells. The amount of antibody detected in the sample would be compared with the amount detected in a control sample.

Antibodies

An antibody embodied in this invention can also be used as a reagent in diagnosis and/or clinical management to detect target Tup1 polypeptides from $C.\ albicans$. Any such polypeptide can be detected in clinical samples by immunochemical and/or immunohistological techniques that will be apparent to a practitioner of ordinary skill. Accordingly, the invention includes methods for detecting a $C.\ albicans$ Tup1 polypeptide (i.e., a polypeptide of this invention) in a biological sample, in which the steps are: (a) contacting polypeptide from the sample with an anti-Tup 1 antibody described herein under conditions that permit the formation of a stable antigen-antibody complex and (b) detecting stable complexes formed, if any.

The antibody used as a reagent may be provided directly with a suitable label. More frequently, the antibody is detected using one of a number of developing reagents which are easily produced or available commercially. Typically, these developing reagents are anti-immunoglobulin or protein A, and they typically bear labels which include, but are not limited to, fluorescent markers such as fluorescein, enzymes such as peroxidase that are capable of precipitating a suitable chemical compound, or that emits light by way of a chemical reaction, electron dense markers such as colloidal gold, or radioisotopes such as $^{125}I$, $^{32}P$, or $^{35}S$.

The amount of polypeptide may be detected in a standard quantitative immunoassay. If the protein is secreted or shed from the cell in any appreciable amount, or is present in white blood cells, it may be detectable in plasma or serum samples. Alternatively, the target protein may be solubilized or extracted from a solid tissue sample. Before quantitating, the protein may optionally be affixed to a solid phase, such as by a blot technique or using a capture antibody.

A number of immunoassay methods are established in the art for performing the quantitation. For example, the protein may be mixed with a pre-determined non-limiting amount of the reagent antibody specific for the protein. The reagent antibody may contain a directly attached label, such as an enzyme or a radioisotope, or a second labeled reagent may be added, such as anti-immunoglobulin or protein A. For a solid-phase assay, unreacted reagents are removed by washing. For a liquid-phase assay, unreacted reagents are removed by some other separation technique, such as filtration or chromatography. The amount of label captured in the complex is positively related to the amount of target protein present in the test sample. A variation of this technique is a competitive assay, in which the target protein competes with a labeled analog for binding sites on the. specific antibody. In this case, the amount of label captured is negatively related to the amount of target protein present in a test sample. Results obtained using any such assay on a sample from a suspected infected source are compared with those from a non-infected source.

Kits Comprising TUP1 Polynucleotides, Polypeptides/or and Antibodies

The present invention also encompasses kits containing TUP1 polynucleotide(s), polypeptide(s), and/or antibodies of this invention, preferably diagnostic kits. Diagnostic procedures using TUP1 polynucleotides, polypeptides and/or antibodies of this invention can be performed by diagnostic laboratories, experimental laboratories, practitioners, or private individuals. Kits embodied by this invention include those that allow someone to conduct an assay for the presence of TUP1 sequences, Tup1 polypeptides and/or anti-Tup1 antibodies, such as any of those disclosed herein, thus detecting an/or quantitating those activities. The kits embodied by this invention also include kits that allow detection of TUP1 polynucleotides in, for example, ex vivo or in vivo transfected cells. These kits can be used for detection or quantitation of a polynucleotide that comprises a polynucleotide encoding a TUP1 or a portion thereof. Accordingly, the invention includes (a) a kit for detection or quantification of a polynucleotide comprising a polynucleotide encoding $C.\ albicans$ Tup1 or a portion thereof in a biological sample; (b) a kit containing anti-Tup 1 antibodies for detection or quantification of a $C.\ albicans$ polypeptide in a biological sample; (c) a kit containing Tup1 polypeptide for detection or quantification of an anti-$C.\ albicans$ antibody in a biological sample.

The kits of this invention are in suitable packaging, and may optionally provide additional components that are useful in the procedure. These optional components include, but are not limited to, buffers, capture reagents, developing reagents, labels, reacting surfaces, means for detection, control samples, instructions, and interpretive information.

Methods Using TUP1 Polynucleotides and Polypeptides: Screening Assays

The present invention also encompasses methods of identifying agents that may have anti-fungal activity based on their ability to elicit a characteristic associated with compromise of C. albicans TUP1 function. These methods may be practiced in a variety of embodiments. We have observed that loss of TUP1 function results in significantly lower infectivity of C. albicans in a mouse model. While not being bound to any one theory, this observation suggests that a pathway(s) involving TUP1 function may play a role in infectivity. This further suggests that modulation of TUP1 function may result in control of the pathogenesis of C. albicans, while not affecting host cells. This is especially true since TUP1 genes are highly diverged between human (i.e., the TUP1 homolog) and fungi. Thus, an agent identified by the methods of the present invention may be useful in the treatment of C. albicans infection.

The methods described herein are in vitro and cell-based screening assays. In the in vitro embodiments, an agent is tested for its ability to modulate function of a Tup1 polypeptide. In the cell-based embodiments, living cells having TUP1 function are used for testing agents. For purposes of this invention, an agent may be identified on the basis of only partial loss of TUP1 function, although characteristics associated with total loss of TUP1 function may be preferable.

In all of these methods, compromise of TUP1 function may occur at any level that negatively affects TUP1 function. An agent may compromise TUP1 function by reducing or preventing transcription of TUP1. An example of such an agent is one that binds to the upstream controlling region, including a polynucleotide sequence or polypeptide. An agent may compromise TUP1 function by reducing or preventing translation of TUP1 mRNA. An example of such an agent is one that binds to the mRNA, such as an anti-sense polynucleotide, or an agent which selectively degrades the mRNA. An agent may compromise TUP1 function by binding to Tup1 or a Tup1 polypeptide. An example of such an agent is a polypeptide or a chelator. An agent may compromise TUP1 function by affecting gene expression of a gene that is regulated by TUP1. An example of such an agent is one that alters expression of a TUP1-regulated gene on any of the levels discussed above.

In Vitro Screening Methods

In in vitro screening assays of this invention, an agent is screened in an in vitro system, which may be any of the following: (1) an assay that determines whether an agent is inhibiting transcription of TUP1; (2) an assay for an agent which interferes with translation of TUP1 MRNA or a polynucleotide encoding Tup1 or a Tup1 polypeptide; (3) an assay for an agent that binds to C. albicans Tup1 or Tup1 polypeptide.

For an assay that determines whether an agent inhibits transcription of TUP1, an in vitro transcription or transcription/translation system may be used. These systems are available commercially, and generally contain a coding sequence as a positive, preferably internal, control. A polynucleotide encoding C. albicans Tup1 (or a Tup1 polypeptide), preferably containing TUP1 flanking sequences, is introduced and transcription is allowed to occur. Comparison of transcription products between an in vitro expression system that does not contain any agent (negative control) with an in vitro expression system that does contain agent indicates whether an agent is affecting TUP1 transcription. Comparison of transcription products between control and TUP1 indicates whether the agent, if acting on this level, is selectively affecting transcription of TUP1 (as opposed to affecting transcription in a general, non-selective or specific fashion).

For an assay that determines whether an agent inhibits translation of TUP1 mRNA or a polynucleotide encoding Tup1 (or a Tup1 polypeptide), an in vitro transcription/translation assay as described above may be used, except the translation products are compared. Comparison of translation products between an in vitro expression system that does not contain any agent (negative control) with an in vitro expression system that does contain agent indicates whether an agent is affecting TUP1 transcription. Comparison of translation products between control and TUP1 indicates whether the agent, if acting on this level, is selectively affecting translation of TUP1 (as opposed to affecting translation in a general, non-selective or specific fashion).

For an assay for an agent that binds to C. albicans Tup1 or Tup1 polypeptide, C. albicans TUP1 is first recombinantly expressed in a prokaryotic or eukaryotic expression system as a native or as a fusion protein in which the full length Tup1 or fragments of Tup1 is conjugated with a well-characterized epitope or protein as described above under "Preparation of polypeptides of this invention". Recombinant Tup1 is then purified by, for instance, immunoprecipitation using anti-Tup1 antibodies or anti-epitope antibodies or by binding to immobilized ligand of the conjugate. An affinity column made of Tup1 or Tup1 fusion protein is then used to screen a mixture of compounds which have been appropriately labeled. Suitable labels include, but are not limited to flurochromes, radioisotopes, enzymes and chemiluminescent compounds. The unbound and bound compounds can be separated by washes using various conditions (e.g. high salt, detergent) that are routinely employed by those skilled in the art. Non-specific binding to the affinity column can be minimized by pre-clearing the compound mixture using an affinity column containing merely the conjugate or the epitope. A similar method can be used for screening for agents that competes for binding to Tup1 polypeptides. In addition to affinity chromatography, there are other techniques such as measuring the change of melting temperature or the fluorescence anisotropy of a protein which will change upon binding another molecule. For example, a BlAcore assay using a sensor chip (supplied by Pharmacia Biosensor, Stitt et al. (1995) *Cell* 80: 661–670) that is covalently coupled to native Tup1 or Tup 1-fusion proteins, may be performed to determine the Tup1 binding activity of different agents.

In another embodiment, an in vitro screening assay detects agents that compete with another substance (most likely a polypeptide) that binds C. albicans Tup1 or a Tup1 polypeptide. For instance, it is known that S. cerevisiae Tup1 is complexed with the protein SSN6 within the cell. If C. albicans Tup1 exerts similar functionality (and may even bind to at least one protein with which S. cerevisiae has been observed to interact), an assay could be conducted such that an agent is tested for its ability to compete with binding to C. albicans Tup1 or Tup1 polypeptide. Competitive binding assays are known in the art and need not be described in detail herein. Briefly, such an assay entails measuring the amount of Tup1 complex formed in the presence of increasing amounts of the putative competitor. For these assays, one of the reactants is labeled using, for example, $^{32}$P.

It is also understood that the in vitro screening methods of this invention include structural, or rational, drug design, in which the amino acid sequence, three-dimensional atomic structure or other property (or properties) of Tup1 (or Tup1 polypeptide) provides a basis for designing an agent which is expected to bind to Tup1 (or Tup1 polypeptide). Generally, the design and/or choice of agents in this context is governed by several parameters, such as the perceived function of the Tup1 (or Tup1 polypeptide) target, its three-dimensional structure (if known or surmised), and other aspects of rational drug design. Techniques of combinatorial chemistry can also be used to generate numerous permutations of candidate agents. For purposes of this invention, an agent designed and/or obtained by rational drug designed may also be tested in the cell-based assays described below.

Cell-based Screening Methods

In cell-based screening assays, a living cell containing a functioning TUP1 gene that is functionally equivalent to (i.e., is complemented by) C. albicans TUP1, or a living cell containing a polynucleotide construct comprising a C. albicans Tup1 encoding sequence are exposed to an agent. In contrast (as described above), conventional drug screening assays have typically measured the effect of a test agent on an isolated component, such as an enzyme or other functional protein.

The cell-based screening assays described herein have several advantages over conventional drug screening assays: 1) if an agent must enter a cell to achieve a desired therapeutic effect, a cell-based assay can give an indication as to whether the agent can enter a cell; 2) a cell-based screening assay can identify agents that, in the state in which they are added to the assay system are ineffective to elicit at least one characteristic which is associated with compromise of C. albicans TUP1 function, but that are modified by cellular components once inside a cell in such a way that they become effective agents; 3) most importantly, a cell-based assay system allows identification of agents affecting any component of a pathway that ultimately results in characteristics that are associated with TUP1 function.

In one embodiment, an agent is identified by its ability to elicit a characteristic associated with compromise of host TUP1 function in a suitable host cell. A suitable host cell in this context is any host cell in which C. albicans TUP1 complements a defect of host cell TUP1 function. For example, our observation that C. albicans TUP1 gene complements S. cerevisiae TUP1 gene provides a new and convenient basis for screening. S. cerevisiae TUP1 function accordingly serves as a substitute (i.e., proxy) for C. albicans TUP1 function. Preferably, the host cell is a fungal cell. Even more preferably, the host cell is a yeast cell. Suitable host cells include, but are not limited to, S. cerevisiae, C. albicans and C. glabrata, Kluyveromyces lactis (K. lactis), Schizosaccharomyces pombe (S. pombe), Neurospora crassa, Aspergillus nidulans, Pichiapastoris, and Yarowia lipolytica.

Determining whether C. albicans TUP1 product can substitute for the host cell's TUP1 (or homology gene product is within the skill of the art. For example, the host cell's TUP1 (or homolog) function may be deleted by, for instance, recombinant methods. C. albicans TUP1, or a polynucleotide encoding a functional C. albicans Tup1 polynucleotide, is then introduced into the cell using methods known in the art, such as electroporation, $CaCl_2$ precipitation, and lithium acetate treatment, spheroplasting of the yeast cells, and the ability of C. albicans TUP1 to restore the lost function is measured by assessing various parameters associated with host cell TUP1 function. Determination of complementarity of C. albicans TUP1 for S. cerevisiae TUP1 is described in Example 3.

In one embodiment, the invention provides methods for identifying an agent that may control virulence in C. albicans comprising the following steps: (a) contacting at least one agent to be tested with a suitable host cell that has TUP1 function; and (b) analyzing at least one characteristic which is associated with loss of TUP1 function in said host cell, wherein an agent is identified by its ability to elicit at least one such characteristic. For these methods, the host cell may be any cell in which TUP1 function has been demonstrated. Examples of host cells include, but are not limited to, S. cerevisiae, C. albicans, other species of Candida (see, e.g., those listed herein), and K. lactis.

In one embodiment, an S. cerevisiae cell exhibiting TUP1 function is contacted with at least one agent to be tested. The ability of this agent(s) to elicit at least one characteristic associated with compromise of S. cerevisiae TUP1 function is then analyzed, and an agent is identified if at least one such characteristic is observed. Characteristics associated with loss of TUP1 function in S. cerevisiae include, but are not limited to, temperature sensitivity at 37° C. (i.e., inability to grow at temperatures at or above 37° C.), slow growth, lack of glucose repression, poor growth on glycerol, inability of alpha cell to mate, inability to sporulate, flocculence, irregular cell shape, lack of repression of various other genes. Examples of genes that are controlled (i.e., repressed) by TUP1 include, but are not limited to, (a) α-specific gene such as MFa1, MFa2, and BAR1; (b) haploid-specific gene such as RME1, STE2, STE3, STE4, STE6, STE5, STE12, STE18, HO, GPA1, FUS3, KSS1, or MATα1; (c) glucose-repressed gene such as RIM15, IME1, SUC2, CYC1, CYC7, COX6, GAL4, GAL1, GAL7, GAL10, GAL2, GAL3, MAL 62, MAL63, MAL61, ICL1, CAT8, GLK1, ADH2, HXT1, HXT2, HXT3, or HXT4; (d) sporulation-specific gene such as DIT1, or DIT2; (e) DNA-damage induced gene such as RNR1, or RNR3; (f) oxygen repressed gene such as ROX1, CYC7, HEM13, ANB1, TIF51B, COX5B, ACC3, ERG11, OLE1, or CPR1; (g) flocculation-specific gene such as FLO1, or FLO5.

For genes that are de-repressed upon loss of TUP1 function, loss of TUP1 function may be measured using a reporter system, in which a reporter gene sequence is operatively linked to the TUP1-repressed gene of interest. As used herein, the term "reporter gene" means a gene that encodes a gene product that can be identified (i.e., a reporter protein). Reporter genes include, but are not limited to, alkaline phosphatase, chloramphenicol acetyl transferase, β-galactosidase, luciferase and green fluorescence protein. Identification methods for the products of reporter genes include, but are not limited to, enzymatic assays and fluorimetric assays. Reporter genes and assays to detect their products are well known in the art and are described, for example in Current Protocols in Molecular Biology, eds. Ausubel et al., Greene Publishing and Wiley-Interscience: New York (1987) and periodic updates. Reporter genes, reporter gene assays and reagent kits are also readily available from commercial sources (Strategene, Invitrogen and etc.)

In another embodiment, the host cell is a C. albicans cell. Characteristics associated with loss of TUP1 function in C.

albicans include, but are not limited to, temperature sensitivity at 42° C. (i.e., no growth above 42° C.), faster growth rate on glycerol compared to wild type growth, exclusively in the form of filaments as opposed to single cells as in the wild type in a variety of nutritive media such as YPD and SD (minimal plus glucose). In one embodiment, the host cell is *C. albicans* in which one of the TUP1 genes has been disrupted, as is described in Example 3. This heterozygous form (i.e., +/−) of TUP1 has been shown to exhibit certain properties which are different from those of the tup1 knockout (i.e., −/−). Thus, compromise of TUP1 function could be observed in these cells.

In another embodiment, these methods comprise the following steps: (a) introducing a polynucleotide encoding *C. albicans* Tup1 (or a functional fragment thereof) into a suitable host cell that otherwise lacks TUP1 function, wherein TUP1 function is restored in said host cell; (b) contacting said cell of step (a) with at least one agent to be tested; (c) analyzing at least one characteristic which is associated with loss of TUP1 function, wherein an agent is identified by its ability to elicit at least one said characteristic.

The host cell used for these methods initially lacks TUP1 function (i.e., lacks TUP1 function before introduction of polynucleotide encoding *C. albicans* Tup1). Lacking TUP1 function may be partial to total. For example, a heterozygous mutant in which one TUP1 gene has been disrupted is described in Example 3 and above. Devising host cells that lack TUP1 (or its homolog) function may be achieved in a variety of ways, including, but not limited to, genetic manipulation such as deletion mutagenesis, recombinant substitution of a functional portion of the gene, frameshift mutations, conventional or classical genetic techniques pertaining to mutant isolation, or alterations of the regulatory domains. For example, *S. cerevisiae* tup1 was constructed as described in Keleher et al. (1992) *Cell* 68:709–719; Williams et al. (1990) IMol. Cell. Biol. 10:6500–6511. For cells in which loss of TUP1 (or its homolog) function is lethal, a plasmid containing a wild type copy of the TUP1 is in the cell during the disruption, or mutagenesis, process. If the cells cannot survive without the plasmid containing the wild-type gene, then it is assumed that the loss of TUP1 function is lethal.

Introduction of polynucleotides encoding *C. albicans* Tup1 or a functional fragment thereof depend on the particular host cell used and may be by any of the many methods known in the art, such as spheroplasting, electroporation, $CaCl_2$ precipitation, lithium acetate treatment, and lipofectamine treatment. For *S. cerevisiae*, introduction of these polynucleotides is preferably accomplished by lithium acetate treatment or electroporation. For *K. lactis*, introduction of these polynucleotides is preferably accomplished by electroporation or spheroplasting. For *C. albicans*, polynucleotides are preferably introduced by lithium acetate treatment, electroporation or spheroplasting.

Polynucleotides introduced into a suitable host cell(s) are polynucleotide constructs comprising a polynucleotide encoding Tup1 or a functional fragment thereof. These constructs contain elements (i.e., functional sequences) which, upon introduction of the construct, allow expression (i.e., transcription, translation, and post-translational modifications, if any) of TUP1 amino acid sequence in the host cell. The composition of these elements will depend upon the host cell being used. For introduction into *S. cerevisiae*, polynucleotide constructs will generally contain an origin of replication, a selectable marker such as URA, LEU, TRP, or ADE and the polynucleotide encoding Tup1 (or a functional fragment thereof) operatively linked to a suitable promoter, such as GAL, MET, or ADH1. For introduction into *C. albicans*, polynucleotide constructs will generally contain a selectable marker such as URA3, ADE2 and the polynucleotide encoding TUP1 (or a functional fragment thereof) operatively linked to a suitable promoter, such as MAL2, or URA3, the promoter sequence naturally associated with TUP1, the promoter associated with a TUP1 gene from an organism other than *C. albicans* such as the *S. cerevisiae* TUP1 promoter. For introduction into *K. lactis*, polynucleotide constructs will generally contain an origin of replication such as KLARS1B, a selectable marker such as HIS3, and the polynucleotide encoding Tup1 (or a functional fragment thereof) operatively linked to a suitable promoter, such as HIS3 or actin. Suitable selectable markers for fungal cells are those that enable the identification of cells that have taken up the nucleic acid, such as axtotrophic markers URA, LEU, ADE. The cell transfectants are placed under selection pressure in which only those transfectants uniquely adapted to survive are those that have taken up and are expressing the marker.

Restoring TUP1 (or its homolog) function in the host cell(s) may be determined by analyzing the host cell(s) for detectable parameters associated with TUP1 function (i.e., wild type). These parameters depend upon the particular host cell used. For *S. cerevisiae*, TUP1 function is associated with any of the following: (a) non-temperature sensitivity (i.e., will grow normally at 37° C.); (b) non-flocculent; (c) regular (spherical) cell shape; (d) rapid growth; (e) ability to grow in glycerol medium; (f) repression of certain genes in the presence of glucose; (f) ability to sporulate; (g) ability of the α cells to mate. Genes known to be repressed in the presence of TUP1 gene product in *S. cerevisiae* have been described above. Williams et al. (1990) *Mol. Cell. Biol.* 10:6500; Keleher et al. (1992) Cell 68:709; Lemontt (1980) *Genetics* 94:899. Given methods well known in the art for making reporter constructs (see above), any of these genes could be altered to accommodate a reporter system. Examples of suitable reporter systems have been discussed above.

Alternatively, in another embodiment, introduction of *C. albicans* TUP1 sequences into a wild type host cell acts as a dominant negative mutation. In this context, an agent would be identified by the ability to partially to fully restore TUP1 function as observed in that host cell.

The host cell(s) in which TUP1 function has been restored is contacted with an agent to be tested. An agent is identified by its ability to elicit at least one characteristic associated with loss of host cell TUP1 function. These characteristics depend upon the host cell used and have been described above. Komachi et al. (1994) *Genes Devel.* 8:2857–2867; Redd et al (1997) *J. Biol. Chem.* 272:11193–11197.

Preferably, a TUP1 polynucleotide is operatively linked to an inducible promoter. Use of an inducible promoter provides a means to determine whether the agent is acting via a TUP1 pathway. If an agent causes a characteristic indicative of loss of TUP1 function to appear in a cell in which the inducible promoter is activated, an observation that the agent fails to elicit the same result in a cell in which the inducible promoter is not activated indicates that the agent is affecting at least one step or aspect of TUP1 function. Conversely, if the characteristic indicating loss of TUP1 function is also observed in a cell in which the inducible promoter is not activated, then it can be assumed that the agent is not necessarily acting solely via the TUP1 functional pathway.

Cell-based screening assays of the present invention can be designed, e.g., by constructing cell lines in which the expression of a reporter protein, ie., an easily assayable protein, such as β-galactosidase, chloramphenicol acetyltransferase (CAT), green fluorescent protein (GFP) or luciferase, is dependent on TUP1 function. For example, a gene under TUP1 control may have reporter sequences inserted within the coding region as described in Example 2. The cell is exposed to a test agent, and, after a time sufficient to effect β-galactosidase expression and sufficient to allow for depletion of previously expressed β-galactosidase, the cells are assayed for the production of β-galactosidase under standard assaying conditions.

Assay methods generally require comparison to a control sample to which no agent is added. Additionally, it may be desirable to use a cell partially or completely lacking TUP1 function as a control. For instance, if an agent were acting along a TUP1 pathway, one might expect to see the same phenotype as tup1 cells treated with agents. If an agent were not acting along a TUP1 pathway, one may expect to see other characteristics that occur in the tup1 when treated with the agent.

The screening methods described above represent primary screens, designed to detect any agent that may exhibit anti-fungal activity. The skilled artisan will recognize that secondary tests will likely be necessary in order to evaluate an agent further. For example, a secondary screen may comprise testing the agent(s) in C. albicans if the initial screen has been performed in a host cell other than C. albicans. A further screen is to perform an infectivity assay using the cells that have been treated with the agent(s). An infectivity assay using mice is described in Example 4, and other animal models (such as rat) are known in the art. In addition, a cytotoxicity assay would be performed as a further corroboration that an agent which tested positive in a primary screen would be suitable for use in living organisms. Any assay for cytotoxicity would be suitable for this purpose, including, for example the MTT assay (Promega).

Methods Using TUP1 Polynucleotides and Peptides: Cloning Genes and Gene Products Along the TUP1 Functional Pathway The invention also provides methods for cloning genes and gene products that are involved in, and/or associated with, a TUP1 function (i.e., a TUP1 functional pathway). Because TUP1 function has been shown to play an important role in filamentous formation, and the tup1 knockout is poorly infective, genes that are involved in a TUP1 pathway may well be suitable and useful drug targets. Further, these gene(s) and gene product(s) may provide even more precise, specific targets for drug discovery and development, and hence therapy. The polynucleotides encoding these genes may also be less conserved among fungi and even among various species of Candida, and thus may be especially suitable diagnostic reagents.

Accordingly, the invention provides methods of isolating genes involved in a TUP1 pathway which entail the following step: (a) identification of polynucleotide sequences which are repressed upon TUP1 expression. For these methods, the polynucleotides are identified using standard techniques in the art for determining differential expression, such as representational difference analysis (RDA).

Preferably, the methods include an additional step of identifying those sequences from step (a) above which are expressed when C. albicans is induced to enter filamentous growth formation. Presumably, this sequence is then considered to be required for filamentous growth. Filamentous growth may be induced, for example, by serum, high temperature, high $CO_2$: $O_2$ ratio, neutral pH, or nutrient-poor media. In this embodiment, the sequence(s) so identified may be said to be associated with filamentous growth as well as associated with TUP1 function, particularly in C. albicans.

Still more preferably, the methods include an additional step of identifying those sequences from step (a) and/or step (b) above which, when deleted, mutated, substituted, or otherwise altered such that the function of the expression product is compromised, inhibits filamentous growth in C. albicans. In this embodiment, the sequence(s) so identified may be said to be required for filamentous growth as well as associated with TUP1 function, particularly in C. albicans.

Methods of and Compositions for Controlling Virulence of C. albicans

The invention also provides methods of inhibiting virulence of C. albicans which entail compromising TUP1 function in C. albicans. Our observation that a C. albicans tup1 knockout has low infectivity in mice (Example 4) indicates that compromising TUP1 function would inhibit C. albicans virulence.

For these methods, compromise of TUP1 function could be achieved by any of a number of ways. Compromise of TUP1 function can occur as a result of disruption of TUP1 expression, due to, for example, genetic manipulations, such as anti-sense polynucleotides, or agents which alter transcription of TUP1 by binding, for instance, to an upstream controlling region of the TUP1 gene. Compromise of TUP1 function can also occur by agents (such as those described above) which bind or otherwise physically interact with Tup1 (or Tup1 polypeptide(s)) and/or any other protein that is regulated by Tup1 (or Tup1 polypeptide).

The invention also includes compositions for controlling C. albicans virulence comprising any of the agents which effect compromise of C. albicans TUP1 function, particularly those agents which, when contacted with C. albicans, result in C. albicans cells which are poorly infective. The agents of these compositions include, but are not limited to: agents which selectively compromise transcription of the TUP1 gene, agents which selectively compromise translation of TUP1 (such as anti-sense polynucleotide sequences), agents which bind (or physically interact) with Tup1, and agents which effect alteration of any gene or gene product involved in a TUP1 pathway (i.e., a pathway regulated by TUP1). If used pharmaceutically, these compositions also preferably include a pharmaceutical excipient, which is known in the art.

The following examples are provided to illustrate but not limit the present invention.

EXAMPLES

Example 1

Cloning TUP1 from Candida albicans

As a first step in searching for homologs of S. cerevisiae TUP1, a gene from the closely related yeast K. lactis was isolated by its ability to complement a tup1 deletion mutation in S. cerevisiae cells. The K. lactis TUP1 gene was similar to S. cerevisiae TUP1, and the shared sequence information was used to design degenerate PCR (polymerase chain reaction) primers to amplify conserved regions in the COOH-terminus of TUP1 from other organisms including C. albicans.

PCR primers used to amplify a fragment of C. albicans TUP1 were:

5'GGGGTACCYTTCCADATNCKNGCYTTR-CARTCNCC (SEQ ID NO:4) coding in reverse for C-terminal GDCKARIWK (SEQ ID NO:5), (A. Cornish-Bowden (1985) *Nucl. Acids Res.* 13:3021), and 5'GGCTGCAGGGNCAYGARCARGAYATHTAYTC (SEQ ID NO:6) coding for N-terminal GHEQDIYS (SEQ ID NO:7).

Cycling parameters were 1 min. at 95° C., 1 min. 55° C., 1 min. ramp to 73° C., and 3 min. at 73° C. (Perkin Elmer Cetus 480 cycler). The resulting 659 bp PCR fragment was cloned via the Pst I and Kpn I sites on the ends into Bluescript-derived pVZ1 to produce p348. A 1 library of C. albicans genomic DNA generously provided by Nina Agabian and colleagues (UCSF), was screened with labeled insert from p348. A 7 kb TUP1-containing Kpn I-Xba I fragment from 1363 was cloned into pVZ1 to form p371. Both strands of the TUP1 open reading frame were sequenced. The C. albicans TUP1 DNA and protein sequences have been deposited in GenBank AF005741.

Sequencing and conceptual translation revealed an open reading frame similar to TUP1 from S. cerevisiae (67% identity over the entire amino acid sequence; FIG. 2A).

Example 2

C. albicans TUP1 Complements S. cerevisiae TUP1

To determine whether the C. albicans TUP1 gene had functional as well as structural similarity to S. cerevisiae TUP1, C. albicans TUP1 was expressed under galactose control in tup1 S. cerevisiae cells. The C. albicans TUP1 open reading frame was amplified with Pfu polymerase and the primers:

5'CGCGGATCCCCACCAGCAATGTCCATGTAT (SEQ ID NO:8);

5'GCGGGTACCGCGATGTTGACGGGTGCTGT (SEQ ID NO:9).

The product was cloned into the CEN/ARS/URA3/Gal1-10 expression vector pRD53 (gift of R. Deshaies, Cal Tech) to form the S. cerevisiae expression plasmid pMH1. C. albicans TUP1 contains no CUG codons, which encode serine in C. albicans, but encode leucine in S. cerevisiae and elsewhere. T. Ohama et al., (1993) *Nucleic Acids Res.* 21:4039. The same PCR product was cloned into pDBV52 (gift of C. Kumimoto and D. Brown, Tufts) to form the maltose-regulated expression plasmid p455 which was transformed into BCa2–9. Transformations of S. cerevisiae were done by a modified lithium acetate technique (R. D. Gietz et al. (1995) *Yeast* 11:355; J. Hill et al. (1991) *Nucleic Acids Res.* 19:5791). pAJ181 has been described Keleher et al. (1992) *Cell* 68:709. KKY110 (Mata, tup1, mfa2::lacZ, leu2, ura3, trp1, his4; a gift of K. Komachi, UCSF) had a β-galactosidase reporter gene under a2/MCM1/TUP1 control integrated at the MFA2 gene.

To assess TUP1 function, β-galactosidase activity was assayed from tup1 S. cerevisiae (KKY110) carrying the plasmids described above. The expressed C. albicans gene restored repression of a genomic a-specific gene reporter, Mfa2: lacZ to wild-type levels. The results are shown in Table 1.

TABLE 1

Analysis of C. albicans TUP1 functions in S. cerevisiae.

| | Vector only pRD53 | Native S. cerevisiae TUP1 pAJ181 | Cal-driven C. albicans TUP1 pMH1 |
|---|---|---|---|
| Glucose | 82 ± 16 | 3.8 ± 0.9 | 32 ± 5 |
| Galactose | 83 ± 27 | 0.7 ± 0.5 | 0.5 ± 0.4 |

Beta-galactosidase activity was assayed from tup1 S. cerevisiae carrying the indicated plasmids. On glucose, the vector (pRD53) conferred 82, ±16 units, (no repression), pAJ. 181 (S. cerevisiae TUP1) conferred 3.8, ±0.9 units, and pMH1 (Gal-driven C. albicans TUP1) conferred 32, ±5 units. On a galactose, the vector conferred 83, ±27 units (no repression), pAJ181, 0.7, ±0.5 units, and pMH1, 0.5, ±0.4 units (full repression).

Additionally, tup1 S. cerevisiae cells over-expressing the C. albicans TUP1 were non-flocculent, non-temperature sensitive, exhibited wild-type cell shape, and grew rapidly, indicating that several other phenotypes characteristic of tup1 cells had also been corrected by the C. albicans gene.

Example 3

Construction of up Knockout Mutant in Candida albicans

Figure 3A:
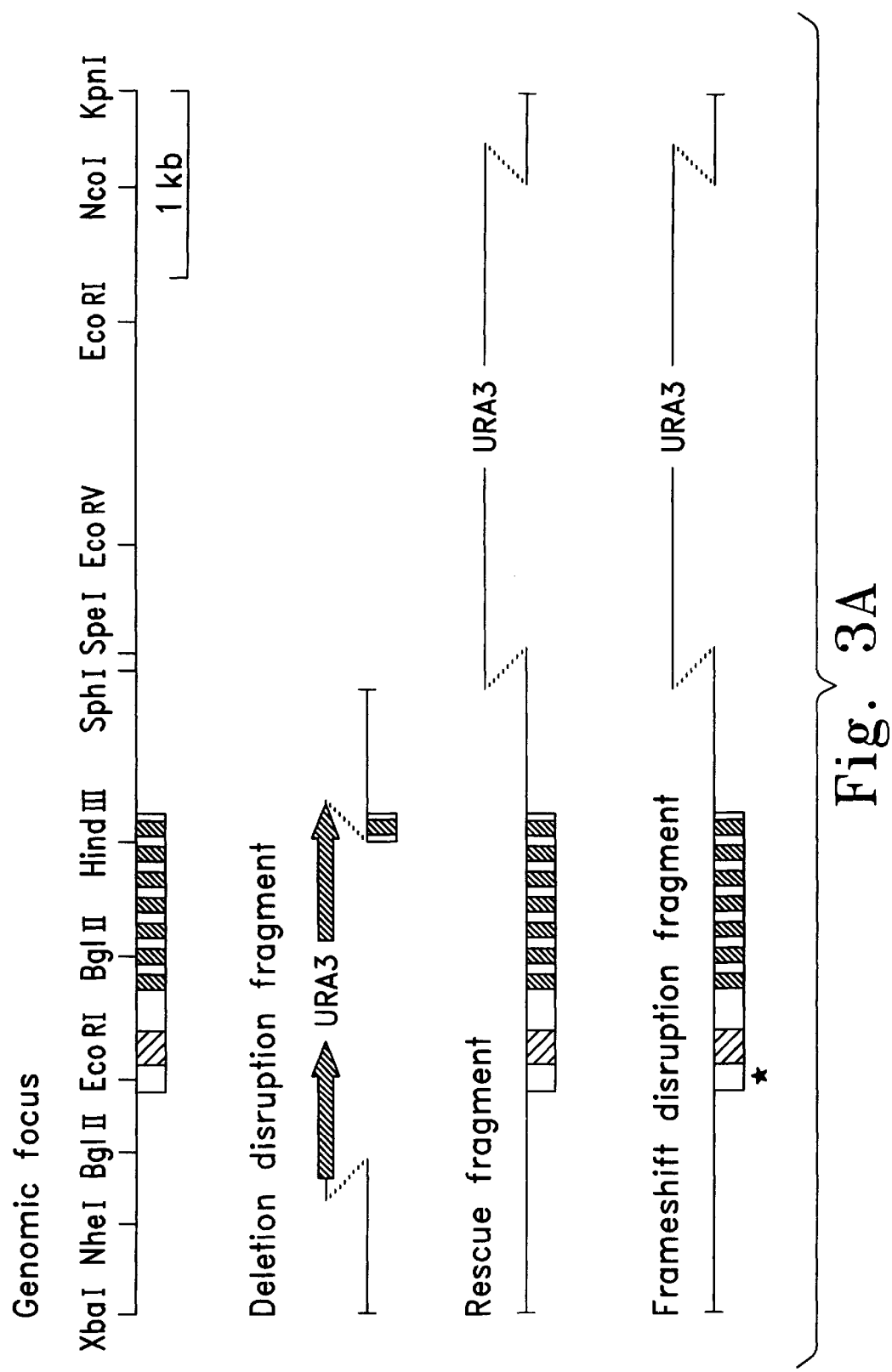
FIGS. 3A (SEQ ID NO:2 and SEQ ID NO:3) and 3B depict the disruption of *C. albicans* TUP1 gene and construction of the tup1 knockout.
Figure 3B:
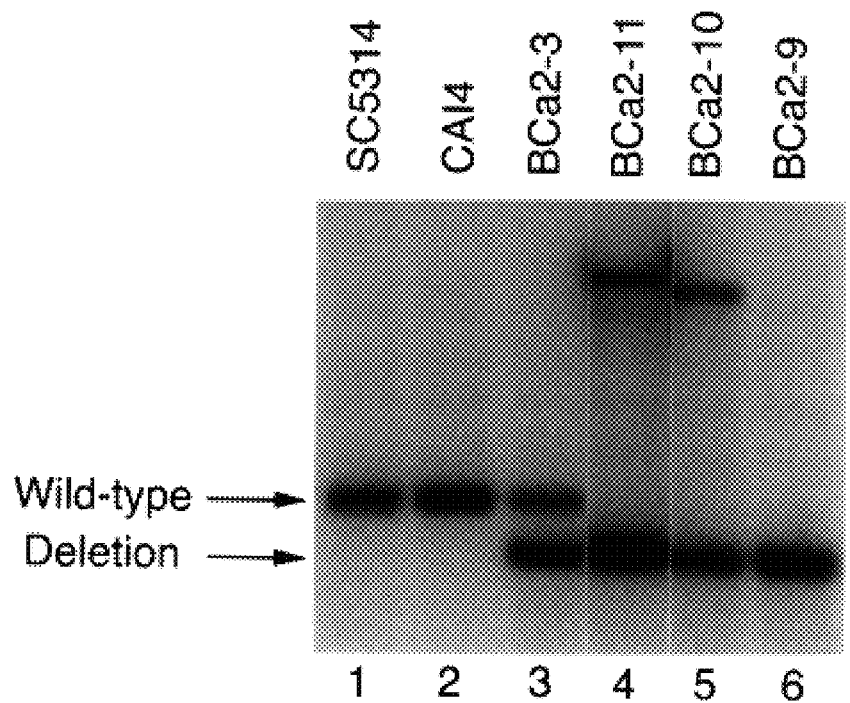
FIG. 3B is a half-tone reproduction of a DNA blot of *C. albicans* genomic DNA (cut with Nhe I-Spe I) probed with the Hind III-Spe I fragment from the TUP1 genomic locus (top line of (A). Lanes 1 and 2, DNA from TUP1/TUP1 strains (length equals 3 kilobasepairs (kbp)); lane 3, DNA from a heterozygous tup1/TUP1 strain(3 kbp and 2.3 kbp); lane 6, DNA from a homozygous tup1/tup1 mutant strain. Lanes 4 and 5 show integration of the p405 rescuing fragment (third line from top in A) into the TUP1 locus. Integration of the sub-portion of the fragment with URA3 but without TUP1 resulted in the slightly smaller band shown in lane 5 (approximately 9 kbp) and did not restore TUP1 function, whereas integration of the entire fragment, shown in lane 4 (approximately 9.7 kbp), did restore TUP1 function.

Both copies of TUP1 were disrupted (C. albicans is diploid) in two rounds as described (W. A. Fonzi and M. Y. Irwin, (1993) *Genetics* 134:717). The C. albicans URA3 gene, flanked by tandemly repeated DNA sequences, was inserted in place of TUP1 within the genomic clone (FIG. 3A) to form p383C, which was cut with Sph I to remove the vector and transformed into ura3 C. albicans cells. Transformation of C. albicans was identical to that of S. cerevisiae, except that DMSO was omitted, incubation times at 30° C. and 42° C. were extended to 3 hr and 1 hr, respectively, and 25 μg/ml uridine was added to the plating solution. URA3 transfonnants were screened by DNA blotting for disruption of one TUP1 gene by homologous recombination. After selecting on 5-FOA (5-fluoroarotic acid) plates for ura3 "pop-out" revertants, a second cycle of transformation was performed. DNA blotting demonstrated the successive disruption of both copies of the TUP1 gene (FIG. 3B, compare lanes 2, 3, and 6). All C. albicans strains shared the SC5314 background. The C. albicans allele tup1:hisG (i.e., heterozygous) described here is referred to as tup1E-1.

The disruption consisted of a large deletion that excised most of the TUP1 gene as well as 330 bp of DNA upstream of the open reading frame. To ensure that the phenotypes described below resulted from loss of TUP1 function rather than loss of the upstream DNA or other features of the locus separate from the TUP1 open reading frame, the second round of disruption was also carried out with a DNA fragment that carried tup1 C. albicans with an N-terminal frame-shift mutation instead of a large deletion (FIG. 3A). The resulting strains were phenotypically identical in all respects to the homozygous mutant strains carrying the large deletions of TUP1, which are described below. Wild-type C. albicans phenotypes were fully restored by insertion of a wild-type copy of the TUP1 gene linked to an adjacent URA3 marker (FIG. 3A) back into the disrupted locus (FIG. 3B, lane 4). Additionally, insertion of a wild-type copy of the gene under the control of a recently described maltase promoter into the genome also rescued the tup1 deletion mutant phenotypes in a maltose-dependent manner.

Figures 4A, 4B, 4C, 4D, 4E, 4F:
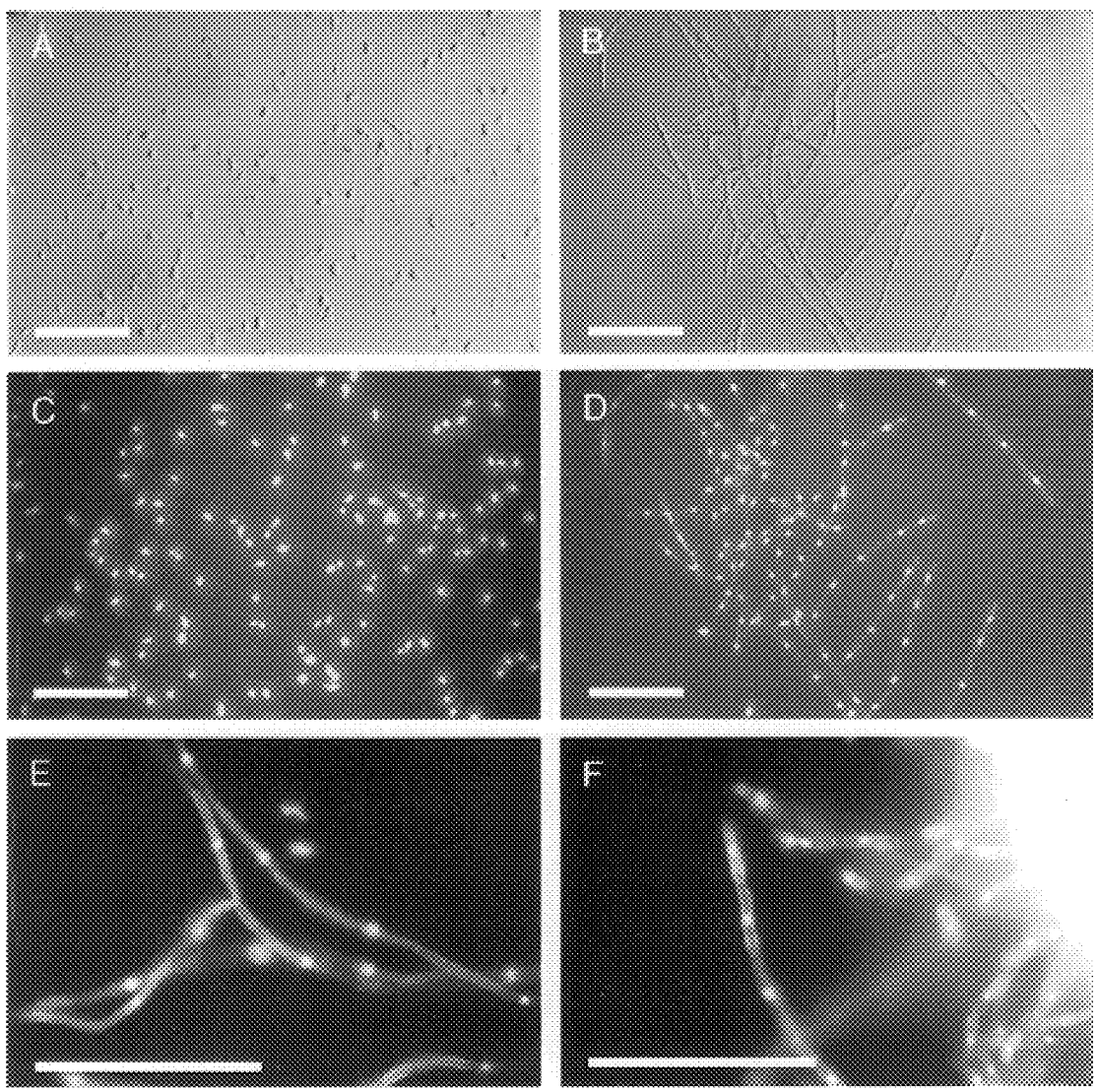
FIGS. 4A through 4F are half-tone reproductions of photographs depicting morphological characteristics of wild-type *C. albicans* cells SC5314 (A, C and E) and tup1 (knockout) cells BCa2–10 (B, D and F). The scale bar equals 50 $\mu$M.
Figure 5A:
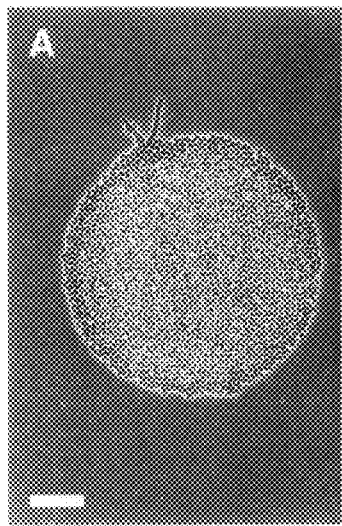
FIGS. 5A through 5C are half-tone reproductions of photographs depicting morphological characteristics of homozygous and heterozygous tup1 strains. The scale bar equals 50 $\mu$M.
Figure 5B:
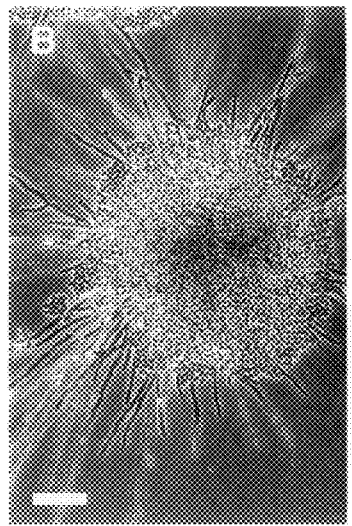
Figure 5C:
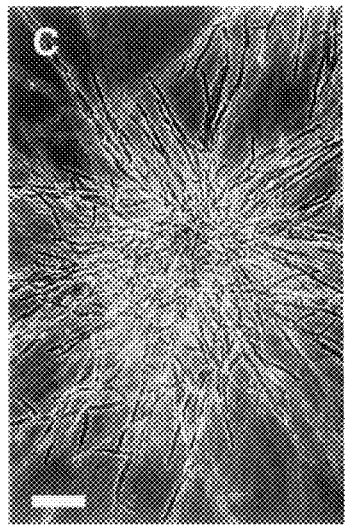

Dramatic differences were observed when tup1 and wild-type *C. albicans* were compared under the microscope (FIG. 4) Wild type and tup1 *C. albicans* cells were grown in YEPD at 30° C. to late log phase and stained with DAPI to highlight the DNA before being photographed at 40× through differential interference contrast (FIGS. 4A and B) and fluorescence optics (FIGS. 4C and D). Wild-type cells SC5314 (FIG. 4E) and tup1 cells BCa2–10 (FIG. 4F) were grown in Lee's medium, pH 6.7, at 37° C., conditions that promote germ tube formation and hyphal growth, and then stained with calcofluor and DAPI to highlight both the cell walls and DNA before being photographed at 100× through fluorescence optics. For FIGS. 4 A–D, both strains were grown under conditions (YEPD) that favor the blastospore form of growth, and as expected, the wild-type strain exhibited the blastospore form under these conditions (A and C). In contrast, the homozygous tup1/tup1 mutant strain was completely filamentous (B and D). In fact, the mutant strain formed only filaments on all media tested, including a variety of common and specialized media: YEPD, YD, Sabourad, cornmeal,Tween 80, Spider, 20% calf serum, Lee's defined, and minimal S medium with a variety of fermentable and non-fermentable carbon sources. On most media, mutant cells grew as pseudohyphae rather than true hyphae, but under certain hyphal-inducing conditions, they attained highly elongated and straight-walled shapes indistinguishable from those of true hyphae (FIGS. 4B and D, and FIG. 5). Some of these conditions included growth on nutrient-poor media such as cornmeal agar, microaerobic growth under glass coverslips and growth on YPED plates for several weeks. The distinction between true hyphae and pseudohyphae is based solely on cell shape, and a spectrum of intermediate morphologies are observed in wild-type *C. albicans* cells (Odds (1988); Odds (1984) *Crit. Rev. Microbiol.* 22:137).

Closer examination of homozygous tup1 mutant cells revealed that aside from their overall altered morphology, they resembled filamentous wild-type cells in most respects (FIGS. 4E and F). In particular, DNA was centrally located in non-mitotic cells, filaments branched several septal compartments behind the growing hyphal tip, and branches were situated near the apical septa, as is normally seen in wild-type *C. albicans*. One minor difference was that the mutant cells often had slightly misshapen cell walls relative to wild-type hyphal cells (FIG. 4F). Heterozygous TUP1/tup1 strains showed a morphological phenotype intermediate between the wild-type and homozygous strains. While their cells resembled wild-type cells in morphology, on most media heterozygous colonies developed a higher proportion of filaments compared to wild-type colonies (FIG. 5B), confirming the filament-repressing role of TUP1 and suggesting that its gene product is present in limiting amounts. For these experiments, Wild-type SC5314 (FIG. 5A), heterozygous BCa2–3' (FIG. 5B), and homozygous BCa2–10 (FIG. 5C) cells were placed on a corn meal agar+Tween 80 plate under a coverslip and grown for 25 hours at 25° C. before being photographed at 40× with phase optics.

While deletion of the TUP1 gene caused constitutive filamentous growth in *C. albicans*, there was a surprising lack of response of tup1 cells to some strong germ tube and filamentous growth inducers such as mammalian serum and Lee's medium. Germ tube formation from the blastospore state is a special property of *C. albicans* and is widely used for clinical identification. Wild-type and TUP1/tup1 heterozygous blastospores exhibited rapid germ tube formation progressing to true hyphae on YEPD or minimal media containing 10–20% calf serum. However, in these same media the homozygous tup1 mutant cells showed no detectable change in their filamentous morphology; in particular, they showed no sign of germ tubes or of increased transformation towards true hyphae.

Example 4

Low Infectivity of tup Knockout Mutants in Mice

Groups of 4 inbred CAB/J(H-2K) mice were inoculated vaginally ($5\times10^5$ CFU) or orally ($1\times107$ CFU) with wild type *C. albicans* SC5314 Fonzi et al. (1993) *Genetics* 134:717–728; Gillum et al. (1984) *Mol. General Genetics* 198:179. or tup knockout *C. albicans* strain BCa2–10 (described above in Example 2). de Bernardis (1993) *Infect. Immun.* 61:1500–1508; Marquis (1986) *J. Infect. Dis.* 154:906–909; Shepherd (1985) *Infect. Immun.* 50:541–544. Fidel et al. 91993)*Immun.* 61:1990–1995; Fidel et al (1996) *J. Infec. Disease* 173 (2):425–43 1. The results are shown in Table 2.

TABLE 2

Effect Of TUP1 Mutant *C. albicans* strains on infectivity

| | | | Vaginal Infections | | | | | |
|---|---|---|---|---|---|---|---|---|
| | | Week 1 - Vaginal | | | Week 2 - Vaginal | | Inoculum | |
| Group | | Mouse | CFU | Mean ± SEM | | CFU | Mean ± SEM | CFU/Ml | CFU/Mouse |
| Group I | SC5314 + Estrogen | 1 | $29 \times 10^4$ | $2.99 \times 10^4$ | 1 | $3.77 \times 10^4$ | $198 \times 10^4$ | $113 \times 10^7$ | $2.26 \times 10^6$ |
| | | 2 | $854 \times 10^4$ | $\pm 1.95 \times 10^4$ | 2 | $1.67 \times 10^4$ | $\pm 6.34 \times 10^2$ | | |
| | | 3 | $1.75 \times 10^2$ | | 3 | $1.69 \times 10^4$ | | | |
| | | 4 | $5.02 \times 10^3$ | | 4 | $7.8 \times 10^3$ | | | |
| Group II | SC5314 − Estrogen | 1 | 0 | $5 \pm 2.89$ | 1 | 0 | 0 | | |
| | | 2 | $1 \times 10^1$ | | 2 | 0 | | | |
| | | 3 | 0 | | 3 | 0 | | | |
| | | 4 | $1 \times 10^1$ | | 4 | 0 | | | |
| Group III | BCa 2-10 + Estrogen | 1 | 0 | $9.5 \times 10^2$ | 1 | 0 | 0 | $5.36 \times 10^7$ | $4.29 \times 10^6$ |
| | | 2 | 0 | $\pm 19.5 \times 10^2$ | 2 | 0 | | | |
| | | 3 | $3.8 \times 10^3$ | | 3 | 0 | | | |
| | | 4 | 0 | | 4 | 0 | | | |
| Group IV | BCa 2-10 − | 1 | 0 | 0 | 1 | 0 | 0 | | |
| | | 2 | 0 | | 2 | 0 | | | |

TABLE 2-continued

Effect Of TUP1 Mutant C. albicans strains on infectivity

| | | | | | | | |
|---|---|---|---|---|---|---|---|
| Estrogen | 3 | 0 | | 3 | 0 | | |
| | 4 | 0 | | 4 | 0 | | |

Gastro-Intestinal Infections

| | | Stool Week 1 - GI | | Stool Week 2 - GI | | Stool Week 3 - GI | | Week 3 gut homogenate |
|---|---|---|---|---|---|---|---|---|
| Group | Mouse | CFU/g | Mean ± SEM | CFU/g | Mean ± SEM | CFU/g | Mean ± SEM | CFU |
| Group V SC5314 | 1 | $5.2 \times 10^5$ | $1.16 \times 10^5$ | $2.93 \times 10^5$ | $1.17 \times 10^5$ | $2.2 \times 10^5$ | $1.59 \times 10^5$ | $9 \times 10^3$ |
| | 2 | $3.5 \times 10^4$ | $\pm 1.24 \times 10^5$ | $5.93 \times 10^4$ | $\pm 6.32 \times 10^4$ | $5.6 \times 10^4$ | $\pm 8.1 \times 10^4$ | |
| | 3 | 0 | 0 | 0 | | 0 | | 0 |
| | 4 | $2.9 \times 10^4$ | | $1.18 \times 10^5$ | | $3.6 \times 10^5$ | | |
| Group VI BCa 2-10 | 1 | 0 | $1.4 \times 10^4$ | 0 | 0 | 0 | 0 | 0 |
| | 2 | $2.8 \times 10^4$ | $\pm 4.9 \times 10^3$ | 0 | | 0 | | 0 |
| | 3 expired | — | | — | | — | | |
| | 4 expired | — | | — | | — | | |

Inoculum - GI

| | CFU/ml | CFU/ms |
|---|---|---|
| SC5314 | $1.39 \times 10^8$ | $1.4 \times 10^7$ |
| BCa 2-10 | $2.12 \times 10^8$ | $2.12 \times 10^7$ |

Four groups of mice were used for vaginal infectivity experiments. Groups I (with pre-treatment of estrogen) and II (without pre-treatment of estrogen) were inoculated with $113 \times 10^7$ CFU (colony forming units) per ml ($2.26 \times 10^6$ CFU per mouse) of wild type strain SC5314. Groups III (with pre-treatment of estrogen) and IV (without pre-treatment of estrogen) received $5.36 \times 10^7$ CFU per ml and $4.29 \times 10^6$ CFU per mouse of tup1 knockout strain Bca2–10. Mice that were not pre-treated with estrogen did not develop C. albicans infection (Table 1). Estrogen-treated mice that received wild type SC5314 developed and maintained C. albicans infection after 1 and 2 weeks as assayed by vaginal lavage (Table 1). In contrast, estrogen-treated mice receiving tup1 knockout strain BCa2–10 had very low titers on days 3–7 post-inoculation and no evidence of infection by day 14 as assayed by vaginal lavage (Table 1). The only mouse that displayed CFU (mouse #3) in the first week after infection had no CFU after the second week after inoculation.

Two groups of mice were used for gastro-intestinal infections. Group V received $1.39 \times 10^8$ CFU/ml ($1.4 \times 10^7$ CFU/mouse) wild type strain SC5314. Group VI received $2.12 \times 10^8$ CFU/ml ($2.12 \times 10^7$/mouse) tup1 knockout strain BCa2–10. Because of the large mass of BCa2–10 cells that were required for infection (due to their large size), two mice in Group VI died before the end of the first week after infection. Three of four mice receiving wild type SC5314 all developed and maintained high titers ($10^4$ to $10^5$ CFU) for three weeks as assayed by stool homogenization (Table 1). Of the two mice that survived inoculation with tup1 knockout BCa2–10, one mouse displayed signs of infection after the first week which disappeared after the second and third weeks (Table 1). The other mouse showed no signs of infection, even after the first week (Table 1).

Based on these experiments, the tup1 knockout strain has significantly lower infectivity than wild type C. albicans.

Example 4

Screening Candidate Anti-fungal Agents Using TUP1

In S. cerevisiae

For one assay in S. cerevisiae, cells are cultured in suspension, and an agent to be tested is added (control cells receive no agent). After a suitable time, cells are grown at 37° C. An agent is identified when non-control cells are unable to grow at this temperature. As a further screen, the cells which are unable to grow at 37° C. are allowed to grow at room temperature, and the shape of these cells is examined microscopically. Irregular cell shape is further confirmation of selection of a suitable agent for further study.

Alternatively, a green fluorescent protein reporter system is incorporated into a TUP1-repressed gene, such as SUC2. An agent to be tested is added (no agent added to control cells). After a suitable time, the cell suspensions are checked for appearance of fluorescence. Agents are identified by ability to elicit fluoresence.

These assays may also be conveniently performed in microtiter plates, in which a small amount of media is placed in each well, along with cells treated with various agents to be tested.

In another assay, a DNA sequence containing a region that encodes C. albicans TUP1 is ligated to a S. cerevisiae promoter, such as GAL1. The plasmid is transformed into S. cerevisiae in which S. cerevisiae TUP1 has been deleted and stable transformants selected. The host S. cerevisiae also contains a β-gal reporter system integrated into to a MFa2 gene, as described in Example 2. An agent to be tested is added to suspensions of the stably transformed cells. After a suitable time, the culture medium is tested for lacZ activity. Control samples include no test agent.

In C. albicans

C. albicans cells are grown in standard media and agent to be tested is added (control cells receive no agent). After a suitable time, cells are grown at 42° C. An agent is identified when non-control cells are unable to grow at this temperature. As a further screen, the cells which are unable to grow at 42° C. are allowed to grow on glycerol. Cells that grow faster in glycerol than control cells is further confirmation of selection of a suitable agent for further study.

Although the foregoing invention has been described in some detail by way of illustration and example for purposes of clarity of understanding, it will be apparent to those skilled I the art that certain changes and modifications can be practiced. Therefore, the description and examples should not be construed as limiting the scope of the invention, which is delineated by the appended claims.

We claim:

1. An isolated polypeptide comprising a thymidine uptake 1 (Tup1) polypeptide sequence from *Candida albicans*, wherein the polypeptide complements a thymidine uptake 1 (tup1) gene mutation in a yeast cell and wherein said polypeptide does not have the same amino acid sequence as *Saccharomyces cerevisiae* Tup1.

2. An isolated polypeptide of claim 1, wherein the yeast cell is *S. cerevisiae*.

3. An isolated polypeptide of claim 1, wherein the yeast cell is *C. albicans*.

4. An isolated polypeptide of claim 1, wherein complementation is evidenced by repression of a gene that is regulated by TUP1.

5. An isolated polypeptide of claim 3, wherein complementation is evidenced by reduction of filamentous growth.

6. An isolated polypeptide of claim 3, wherein complementation is evidenced by an increase in virulence.

7. An isolated polypeptide of claim 1, wherein the polypeptide comprises about amino acid residue 190 to about amino acid residue 465 of SEQ ID NO: 2.

8. An isolated polypeptide of claim 1, wherein the polypeptide comprises about amino acid residue 1 to about amino acid residue 465 of SEQ ID NO: 2.

9. An isolated polypeptide of claim 1, wherein the polypeptide comprises the sequence of SEQ ID NO: 2.

10. A composition comprising the polypeptide of claim 1.

11. A composition comprising the polypeptide of claim 8.

12. A kit for detection or quantification of a *Candida albicans* polypeptide in a biological sample, said kit comprising an antibody that specifically binds a polypeptide of claim 1 in suitable packaging.

13. A kit for detection or quantification of an anti-*Candida albicans* antibody in a biological sample, said kit comprising the polypeptide of claim 1 in suitable packaging.

14. The kit of claim 12 wherein said antibody is a monoclonal antibody.

15. A method for detecting an anti-*Candida albicans* thymidine uptake 1 (Tup1) antibody in a biological sample, comprising the steps of: (a) contacting antibody from the sample with the polypeptide of claim 1 under conditions which permit formation of a stable antigen-antibody complex; and (b) detecting said stable complexes formed in step (a).

16. The method of claim 15, wherein the polypeptide comprises about amino acid residue 190 to about amino acid residue 465 of SEQ ID NO: 2.

17. The method of claim 15, wherein the polypeptide comprises about amino acid residue 1 to about amino acid residue 465 of SEQ ID NO: 2.

18. The method of claim 15, wherein the polypeptide comprises the sequence of SEQ ID NO: 2.

19. An isolated polypeptide comprising a thymidine uptake 1 (Tup1) polypeptide sequence from *Candida albicans*, wherein the polypeptide complements a thymidine uptake 1 (tup1) gene mutation in a yeast cell and wherein said polypeptide comprises at least 25 contiguous amino acids of SEQ ID NO: 2.

20. The isolated polypeptide of claim 19, wherein said polypeptide sequence comprises at least 30 contiguous amino acids of SEQ ID NO: 2.

21. The isolated polypeptide of claim 19, wherein said polypeptide sequence comprises at least 40 contiguous amino acids of SEQ ID NO: 2.

22. An isolated polypeptide of claim 19, wherein the yeast cell is *S. cerevisiae*.

23. An isolated polypeptide of claim 19, wherein the yeast cell is *C. albicans*.

24. An isolated polypeptide of claim 19, wherein complementation is evidenced by repression of a gene that is regulated by TUP1.

25. An isolated polypeptide of claim 23, herein complementation is evidenced by reduction of filamentous growth.

26. An isolated polypeptide of claim 23, wherein complementation is evidenced by an increase in virulence.

27. A composition comprising the polypeptide of claim 19.

28. A kit for detection or quantification of a *Candida albicans* polypeptide in a biological sample, said kit comprising an antibody that specifically binds a polypeptide of claim 19 in suitable packaging.

29. A kit for detection or quantification of an anti-*Candida albicans* antibody in a biological sample, said kit comprsing the polypeptide of claim 19 in suitable packaging.

30. The kit of claim 28 wherein said antibody is a monoclonal antibody.

31. A method for detecting an anti-*Candida albicans* Tup1 antibody in a biological sample, comprising the steps of: (a) contacting antibody from the sample with the thymidine uptake 1 polypeptide of claim 19 under conditions which permit formation of a stable antigen-antibody complex; and (b) detecting said stable complexes formed in step (a).

32. The method of claim 31, wherein said polypeptide comprises at least 30 contiguous amino acids of SEQ ID NO: 2.

33. The method of claim 31, wherein said polypeptide comprises at least 40 contiguous amino acids of SEQ ID NO: 2.

* * * * *

```
                        SEQUENCE LISTING

<160> NUMBER OF SEQ ID NOS: 9

<210> SEQ ID NO 1
<211> LENGTH: 2272
<212> TYPE: DNA
<213> ORGANISM: Candida albicans
<220> FEATURE:
<221> NAME/KEY: CDS
<222> LOCATION: (337)..(1878)

<400> SEQUENCE: 1
agatcttggg cagtgacagc tttactactc ttgtggtagc tacagtcaaa cccctcttct      60
aaacattgtc actacattct ttattaatta gattgcaagt tactatgcaa aaactatatg     120
tagagtaaat aaaaacaaag aggggccga taatagatca ctcgatatac cccatgacag     180
ttgtgtgtct aactacactc ctgattagag ttcgcaagaa attgtgctcc acacgactat    240
tccaattcgt aaaaaatctg ccatttgaaa aaagcgcacc ccctgttcaa aaaaccaac     300 gaaaaaacaa cacaacttct tccatcccca ccagca atg tcc atg tat ccc caa       354
                                        Met Ser Met Tyr Pro Gln
                                          1               5 cgc acc cag cac caa caa cgt ttg aca gag ttg ttg gat gca atc aaa      402
Arg Thr Gln His Gln Gln Arg Leu Thr Glu Leu Leu Asp Ala Ile Lys
         10                  15                  20 act gaa ttc gac tac gcc tca aac gaa gca agc agt ttc aaa aag gtc     450
Thr Glu Phe Asp Tyr Ala Ser Asn Glu Ala Ser Ser Phe Lys Lys Val
     25                  30                  35 caa gaa gat tat gac tca aag tac caa caa caa gct gcc gaa atg caa     498
Gln Glu Asp Tyr Asp Ser Lys Tyr Gln Gln Gln Ala Ala Glu Met Gln
 40                  45                  50 caa atc cgc caa aca gtg tat gac ttg gag ttg gcc cat aga aaa atc     546
Gln Ile Arg Gln Thr Val Tyr Asp Leu Glu Leu Ala His Arg Lys Ile
 55                  60                  65                  70 aaa gag gca tac gag gaa gag ata ttg agg tta aag aac gag ttg gac     594
Lys Glu Ala Tyr Glu Glu Glu Ile Leu Arg Leu Lys Asn Glu Leu Asp
                 75                  80                  85 act aga gac agg caa atg aag aat ggc ttc caa caa caa cag caa cag     642
Thr Arg Asp Arg Gln Met Lys Asn Gly Phe Gln Gln Gln Gln Gln Gln
             90                  95                 100 caa caa cag caa caa caa cag caa cag cag caa caa caa cag att gtg    690
Gln Gln Gln Gln Gln Gln Gln Gln Gln Gln Gln Gln Gln Ile Val
            105                 110                 115 gca cca cct gcc gcc cca cct gct cca cca acc ccg gtc aca tca tta    738
Ala Pro Pro Ala Ala Pro Pro Ala Pro Pro Thr Pro Val Thr Ser Leu
        120                 125                 130 tcg gtt atc gac aag tca caa tac att gtc aac ccc acc caa aga gct    786
Ser Val Ile Asp Lys Ser Gln Tyr Ile Val Asn Pro Thr Gln Arg Ala
135                 140                 145                 150 aac cac gtc aag gaa atc cca cca ttc ttg caa gat tta gac att gcc    834
Asn His Val Lys Glu Ile Pro Pro Phe Leu Gln Asp Leu Asp Ile Ala
                155                 160                 165 aaa gcc aac ccc gag ttc aag aaa cag cac ctc gaa tac tat gtg ttg    882
Lys Ala Asn Pro Glu Phe Lys Lys Gln His Leu Glu Tyr Tyr Val Leu
```

-continued

|  |  |  |  |  |  |  |  |  |  |  |  |  |  |  |  |
|---|---|---|---|---|---|---|---|---|---|---|---|---|---|---|---|
|  |  | 170 |  |  |  | 175 |  |  |  | 180 |  |  |  |  |  |
| tac | aac | cca | gcg | ttc | tcc | aaa | gac | ttg | gat | att | gac | atg | gtc | cac | tcc | 930 |
| Tyr | Asn | Pro | Ala | Phe | Ser | Lys | Asp | Leu | Asp | Ile | Asp | Met | Val | His | Ser |  |
|  |  | 185 |  |  |  | 190 |  |  |  | 195 |  |  |  |  |  |
| tta | gac | cac | tcg | tca | gtt | gtt | tgc | tgc | gtg | aga | ttt | tcc | aga | gac | ggc | 978 |
| Leu | Asp | His | Ser | Ser | Val | Val | Cys | Cys | Val | Arg | Phe | Ser | Arg | Asp | Gly |  |
|  | 200 |  |  |  | 205 |  |  |  | 210 |  |  |  |  |  |  |
| aag | ttc | atc | gcc | acc | ggt | tgc | aac | aaa | acc | acc | caa | gtg | ttc | aat | gtc | 1026 |
| Lys | Phe | Ile | Ala | Thr | Gly | Cys | Asn | Lys | Thr | Thr | Gln | Val | Phe | Asn | Val |  |
| 215 |  |  |  | 220 |  |  |  | 225 |  |  |  | 230 |  |  |  |
| acc | acc | gga | gag | ttg | gtc | gcc | aaa | ttg | att | gac | gag | tcc | tcc | aac | gaa | 1074 |
| Thr | Thr | Gly | Glu | Leu | Val | Ala | Lys | Leu | Ile | Asp | Glu | Ser | Ser | Asn | Glu |  |
|  |  |  | 235 |  |  |  | 240 |  |  |  | 245 |  |  |  |  |
| aac | aaa | gac | gac | aac | acc | acc | gcc | tca | ggc | gac | ttg | tac | atc | aga | tct | 1122 |
| Asn | Lys | Asp | Asp | Asn | Thr | Thr | Ala | Ser | Gly | Asp | Leu | Tyr | Ile | Arg | Ser |  |
|  |  | 250 |  |  |  | 255 |  |  |  | 260 |  |  |  |  |  |
| gtg | tgt | ttc | tcc | cct | gac | gga | aaa | ctc | ttg | gcg | aca | ggt | gca | gaa | gac | 1170 |
| Val | Cys | Phe | Ser | Pro | Asp | Gly | Lys | Leu | Leu | Ala | Thr | Gly | Ala | Glu | Asp |  |
|  | 265 |  |  |  | 270 |  |  |  | 275 |  |  |  |  |  |  |
| aag | ttg | att | aga | atc | tgg | gat | ttg | agc | aca | aag | aga | att | atc | aaa | atc | 1218 |
| Lys | Leu | Ile | Arg | Ile | Trp | Asp | Leu | Ser | Thr | Lys | Arg | Ile | Ile | Lys | Ile |  |
|  | 280 |  |  |  | 285 |  |  |  | 290 |  |  |  |  |  |  |
| ttg | agg | ggc | cac | gaa | caa | gac | att | tac | tcg | tta | gac | ttt | ttc | cct | gat | 1266 |
| Leu | Arg | Gly | His | Glu | Gln | Asp | Ile | Tyr | Ser | Leu | Asp | Phe | Phe | Pro | Asp |  |
| 295 |  |  |  | 300 |  |  |  | 305 |  |  |  | 310 |  |  |  |
| ggc | gat | agg | ttg | gtt | tca | ggc | tcc | ggc | gat | agg | tca | gtc | aga | atc | tgg | 1314 |
| Gly | Asp | Arg | Leu | Val | Ser | Gly | Ser | Gly | Asp | Arg | Ser | Val | Arg | Ile | Trp |  |
|  |  |  | 315 |  |  |  | 320 |  |  |  | 325 |  |  |  |  |
| gac | ttg | aga | acc | tcc | cag | tgt | tcc | ttg | act | ttg | tcg | atc | gaa | gac | ggc | 1362 |
| Asp | Leu | Arg | Thr | Ser | Gln | Cys | Ser | Leu | Thr | Leu | Ser | Ile | Glu | Asp | Gly |  |
|  |  | 330 |  |  |  | 335 |  |  |  | 340 |  |  |  |  |  |
| gtc | acc | acc | gtg | gcc | gtc | tcc | ccc | gac | ggc | aaa | ctc | att | gct | gcc | ggc | 1410 |
| Val | Thr | Thr | Val | Ala | Val | Ser | Pro | Asp | Gly | Lys | Leu | Ile | Ala | Ala | Gly |  |
|  |  | 345 |  |  |  | 350 |  |  |  | 355 |  |  |  |  |  |
| tca | tta | gat | aga | acc | gtt | aga | gtg | tgg | gac | tca | act | acc | ggg | ttc | ttg | 1458 |
| Ser | Leu | Asp | Arg | Thr | Val | Arg | Val | Trp | Asp | Ser | Thr | Thr | Gly | Phe | Leu |  |
|  | 360 |  |  |  | 365 |  |  |  | 370 |  |  |  |  |  |  |
| gtc | gaa | cgc | tta | gac | tcc | ggc | aac | gaa | aac | ggc | aat | ggc | cac | gaa | gat | 1506 |
| Val | Glu | Arg | Leu | Asp | Ser | Gly | Asn | Glu | Asn | Gly | Asn | Gly | His | Glu | Asp |  |
| 375 |  |  |  | 380 |  |  |  | 385 |  |  |  | 390 |  |  |  |
| tca | gtc | tac | tct | gtc | gcc | ttc | tcc | aac | aac | ggc | gaa | caa | atc | gct | tcc | 1554 |
| Ser | Val | Tyr | Ser | Val | Ala | Phe | Ser | Asn | Asn | Gly | Glu | Gln | Ile | Ala | Ser |  |
|  |  |  | 395 |  |  |  | 400 |  |  |  | 405 |  |  |  |  |
| ggg | tcc | tta | gac | aga | acc | gtc | aag | ttg | tgg | cac | ttg | gaa | ggc | aag | tcc | 1602 |
| Gly | Ser | Leu | Asp | Arg | Thr | Val | Lys | Leu | Trp | His | Leu | Glu | Gly | Lys | Ser |  |
|  |  | 410 |  |  |  | 415 |  |  |  | 420 |  |  |  |  |  |
| gac | aaa | aag | tcg | acc | tgc | gag | gta | acc | tac | att | ggc | cac | aag | gac | ttt | 1650 |
| Asp | Lys | Lys | Ser | Thr | Cys | Glu | Val | Thr | Tyr | Ile | Gly | His | Lys | Asp | Phe |  |
|  |  | 425 |  |  |  | 430 |  |  |  | 435 |  |  |  |  |  |
| gtt | ttg | tcg | gtc | tgc | tgt | acc | ccc | gac | aac | gag | tac | att | ttg | tcg | ggc | 1698 |
| Val | Leu | Ser | Val | Cys | Cys | Thr | Pro | Asp | Asn | Glu | Tyr | Ile | Leu | Ser | Gly |  |
|  |  | 440 |  |  |  | 445 |  |  |  | 450 |  |  |  |  |  |
| tca | aag | gac | cgt | ggt | gtc | att | ttc | tgg | gac | caa | gct | tca | ggt | aac | cca | 1746 |
| Ser | Lys | Asp | Arg | Gly | Val | Ile | Phe | Trp | Asp | Gln | Ala | Ser | Gly | Asn | Pro |  |
| 455 |  |  |  | 460 |  |  |  | 465 |  |  |  | 470 |  |  |  |
| ttg | ttg | atg | ttg | cag | ggc | cac | cgc | aac | tcg | gtc | atc | tca | gtc | gct | gta | 1794 |
| Leu | Leu | Met | Leu | Gln | Gly | His | Arg | Asn | Ser | Val | Ile | Ser | Val | Ala | Val |  |
|  |  |  | 475 |  |  |  | 480 |  |  |  | 485 |  |  |  |  |
| tcc | cta | aac | tca | aag | gga | acc | gaa | ggt | atc | ttc | gct | aca | ggt | agt | ggc | 1842 |

```
Ser Leu Asn Ser Lys Gly Thr Glu Gly Ile Phe Ala Thr Gly Ser Gly
            490                 495                 500 gat tgt aaa gcc aga att tgg aaa tgg acc aaa aaa taagtgtgta                    1888
Asp Cys Lys Ala Arg Ile Trp Lys Trp Thr Lys Lys
            505                 510 gtatatatat atgtgagaaa aaaaaacacc accaaaaaaa aaaattttt tcgtaacaac              1948 ccaccatcaa tgtactctgc ttctgtcaca gcacccgtca acatcgccgt aagtaaaaac             2008
aagaccaacc atcaattgaa tgtctactaa cgtacttaga cccttaagta ttgggggaaa             2068
cgagacaagt cgttgaactt gcccaccaac tcgtccatct ccgtcacctt atcccaagac             2128
gatttgcgaa cccttgacaa ccgccttctg catctggaat cattcgaaaa aagaccaatt             2188
gcggctcaat ggcaaagtcg ggaatcatta gattcctcca cgtccctcaa gcgtgtttta             2248
gcaggacttg gagaaaagtt tacg                                                    2272

<210> SEQ ID NO 2
<211> LENGTH: 514
<212> TYPE: PRT
<213> ORGANISM: Candida albicans

<400> SEQUENCE: 2

Met Ser Met Tyr Pro Gln Arg Thr Gln His Gln Gln Arg Leu Thr Glu
1               5                   10                  15

Leu Leu Asp Ala Ile Lys Thr Glu Phe Asp Tyr Ala Ser Asn Glu Ala
            20                  25                  30

Ser Ser Phe Lys Lys Val Gln Glu Asp Tyr Asp Ser Lys Tyr Gln Gln
        35                  40                  45

Gln Ala Ala Glu Met Gln Gln Ile Arg Gln Thr Val Tyr Asp Leu Glu
    50                  55                  60

Leu Ala His Arg Lys Ile Lys Glu Ala Tyr Glu Glu Ile Leu Arg
65                  70                  75                  80

Leu Lys Asn Glu Leu Asp Thr Arg Asp Arg Gln Met Lys Asn Gly Phe
            85                  90                  95

Gln Gln Gln Gln Gln Gln Gln Gln Gln Gln Gln Gln Gln Gln Gln Gln
            100                 105                 110

Gln Gln Gln Gln Ile Val Ala Pro Pro Ala Ala Pro Pro Ala Pro Pro
        115                 120                 125

Thr Pro Val Thr Ser Leu Ser Val Ile Asp Lys Ser Gln Tyr Ile Val
130                 135                 140

Asn Pro Thr Gln Arg Ala Asn His Val Lys Glu Ile Pro Pro Phe Leu
145                 150                 155                 160

Gln Asp Leu Asp Ile Ala Lys Ala Asn Pro Glu Phe Lys Lys Gln His
            165                 170                 175

Leu Glu Tyr Tyr Val Leu Tyr Asn Pro Ala Phe Ser Lys Asp Leu Asp
        180                 185                 190

Ile Asp Met Val His Ser Leu Asp His Ser Ser Val Val Cys Cys Val
    195                 200                 205

Arg Phe Ser Arg Asp Gly Lys Phe Ile Ala Thr Gly Cys Asn Lys Thr
    210                 215                 220

Thr Gln Val Phe Asn Val Thr Thr Gly Glu Leu Val Ala Lys Leu Ile
225                 230                 235                 240

Asp Glu Ser Ser Asn Glu Asn Lys Asp Asp Asn Thr Thr Ala Ser Gly
            245                 250                 255

Asp Leu Tyr Ile Arg Ser Val Cys Phe Ser Pro Asp Gly Lys Leu Leu
        260                 265                 270
```

-continued

```
Ala Thr Gly Ala Glu Asp Lys Leu Ile Arg Ile Trp Asp Leu Ser Thr
            275                 280                 285
Lys Arg Ile Ile Lys Ile Leu Arg Gly His Glu Gln Asp Ile Tyr Ser
        290                 295                 300
Leu Asp Phe Phe Pro Asp Gly Asp Arg Leu Val Ser Gly Ser Gly Asp
305                 310                 315                 320
Arg Ser Val Arg Ile Trp Asp Leu Arg Thr Ser Gln Cys Ser Leu Thr
                325                 330                 335
Leu Ser Ile Glu Asp Gly Val Thr Thr Val Ala Val Ser Pro Asp Gly
            340                 345                 350
Lys Leu Ile Ala Ala Gly Ser Leu Asp Arg Thr Val Arg Val Trp Asp
        355                 360                 365
Ser Thr Thr Gly Phe Leu Val Glu Arg Leu Asp Ser Gly Asn Glu Asn
370                 375                 380
Gly Asn Gly His Glu Asp Ser Val Tyr Ser Val Ala Phe Ser Asn Asn
385                 390                 395                 400
Gly Glu Gln Ile Ala Ser Gly Ser Leu Asp Arg Thr Val Lys Leu Trp
                405                 410                 415
His Leu Glu Gly Lys Ser Asp Lys Lys Ser Thr Cys Glu Val Thr Tyr
            420                 425                 430
Ile Gly His Lys Asp Phe Val Leu Ser Val Cys Cys Thr Pro Asp Asn
        435                 440                 445
Glu Tyr Ile Leu Ser Gly Ser Lys Asp Arg Gly Val Ile Phe Trp Asp
        450                 455                 460
Gln Ala Ser Gly Asn Pro Leu Leu Met Leu Gln Gly His Arg Asn Ser
465                 470                 475                 480
Val Ile Ser Val Ala Val Ser Leu Asn Ser Lys Gly Thr Glu Gly Ile
                485                 490                 495
Phe Ala Thr Gly Ser Gly Asp Cys Lys Ala Arg Ile Trp Lys Trp Thr
                500                 505                 510
Lys Lys

<210> SEQ ID NO 3
<211> LENGTH: 713
<212> TYPE: PRT
<213> ORGANISM: Candida albicans

<400> SEQUENCE: 3

Met Thr Ala Ser Val Ser Asn Thr Gln Asn Lys Leu Asn Glu Leu Leu
1               5                   10                  15
Asp Ala Ile Arg Gln Glu Phe Leu Gln Val Ser Gln Glu Ala Asn Thr
            20                  25                  30
Tyr Arg Leu Gln Asn Gln Lys Asp Tyr Asp Phe Lys Met Asn Gln Gln
        35                  40                  45
Leu Ala Glu Met Gln Gln Ile Arg Asn Thr Val Tyr Glu Leu Glu Leu
    50                  55                  60
Thr His Arg Lys Met Lys Asp Ala Tyr Glu Ala Glu Ile Lys His Leu
65                  70                  75                  80
Lys Leu Gly Leu Glu Gln Arg Asp His Gln Ile Ala Ser Leu Thr Val
                85                  90                  95
Gln Gln Gln Gln Gln Gln Gln Gln Gln Val Gln Gln His Leu
            100                 105                 110
Gln Gln Gln Gln Gln Leu Ala Ala Ala Ser Ala Ser Val Pro Val
        115                 120                 125
```

-continued

```
Ala Gln Gln Pro Pro Ala Thr Thr Ser Ala Thr Ala Thr Pro Ala Ala
    130                 135                 140

Asn Thr Thr Thr Gly Ser Pro Ser Ala Phe Pro Val Gln Ala Ser Arg
145                 150                 155                 160

Pro Asn Leu Val Gly Ser Gln Leu Pro Thr Thr Thr Leu Pro Val Val
                165                 170                 175

Ser Ser Asn Ala Gln Gln Leu Pro Gln Gln Leu Gln Gln Gln
            180                 185                 190

Gln Leu Gln Gln Gln Gln Pro Pro Gln Val Ser Val Ala Pro Leu
    195                 200                 205

Ser Asn Thr Ala Ile Asn Gly Ser Pro Thr Ser Lys Glu Thr Thr Thr
210                 215                 220

Leu Pro Ser Val Lys Ala Pro Glu Ser Thr Leu Lys Glu Thr Glu Pro
225                 230                 235                 240

Glu Asn Asn Asn Thr Ser Lys Ile Asn Asp Thr Gly Ser Ala Thr Thr
                245                 250                 255

Ala Thr Thr Thr Thr Ala Thr Glu Thr Glu Ile Lys Pro Lys Glu Glu
            260                 265                 270

Asp Ala Thr Pro Ala Ser Leu His Gln Asp His Tyr Leu Val Pro Tyr
    275                 280                 285

Asn Gln Arg Ala Asn His Ser Lys Pro Ile Pro Pro Phe Leu Leu Asp
290                 295                 300

Leu Asp Ser Gln Ser Val Pro Asp Ala Leu Lys Lys Gln Thr Asn Asp
305                 310                 315                 320

Tyr Tyr Ile Leu Tyr Asn Pro Ala Leu Pro Arg Glu Ile Asp Val Glu
                325                 330                 335

Leu His Lys Ser Leu Asp His Thr Ser Val Val Cys Val Lys Phe
            340                 345                 350

Ser Asn Asp Gly Glu Tyr Leu Ala Thr Gly Cys Asn Lys Thr Thr Gln
    355                 360                 365

Val Tyr Arg Val Ser Asp Gly Ser Leu Val Ala Arg Leu Ser Asp Asp
370                 375                 380

Ser Ala Ala Asn Asn His Arg Asn Ser Ile Thr Glu Asn Asn Thr Thr
385                 390                 395                 400

Thr Ser Thr Asp Asn Asn Thr Met Thr Thr Thr Thr Thr Thr Thr Ile
                405                 410                 415

Thr Thr Thr Ala Met Thr Ser Ala Ala Glu Leu Ala Lys Asp Val Glu
            420                 425                 430

Asn Leu Asn Thr Ser Ser Ser Pro Ser Ser Asp Leu Tyr Ile Arg Ser
    435                 440                 445

Val Cys Phe Ser Pro Asp Gly Lys Phe Leu Ala Thr Gly Ala Glu Asp
450                 455                 460

Arg Leu Ile Arg Ile Trp Asp Ile Glu Asn Arg Lys Ile Val Met Ile
465                 470                 475                 480

Leu Gln Gly His Glu Gln Asp Ile Tyr Ser Leu Asp Tyr Phe Pro Ser
                485                 490                 495

Gly Asp Lys Leu Val Ser Gly Ser Gly Asp Arg Thr Val Arg Ile Trp
            500                 505                 510

Asp Leu Arg Thr Gly Gln Cys Ser Leu Thr Leu Ser Ile Glu Asp Gly
    515                 520                 525

Val Thr Thr Val Ala Val Ser Pro Gly Asp Gly Lys Tyr Ile Ala Ala
530                 535                 540
```

```
Gly Ser Leu Asp Arg Ala Val Arg Val Trp Asp Ser Glu Thr Gly Phe
545                 550                 555                 560

Leu Val Glu Arg Leu Asp Ser Glu Asn Glu Ser Gly Thr Gly His Lys
            565                 570                 575

Asp Ser Val Tyr Ser Val Val Phe Thr Arg Asp Gly Gln Ser Val Val
        580                 585                 590

Ser Gly Ser Leu Asp Arg Ser Val Lys Leu Trp Asn Leu Gln Asn Ala
    595                 600                 605

Asn Asn Lys Ser Asp Ser Lys Thr Pro Asn Ser Gly Thr Cys Glu Val
610                 615                 620

Thr Tyr Ile Gly His Lys Asp Phe Val Leu Ser Val Ala Thr Thr Gln
625                 630                 635                 640

Asn Asp Glu Tyr Ile Leu Ser Gly Ser Lys Asp Arg Gly Val Leu Phe
            645                 650                 655

Trp Asp Lys Lys Ser Gly Asn Pro Leu Leu Met Leu Gln Gly His Arg
        660                 665                 670

Asn Ser Val Ile Ser Val Ala Val Ala Asn Gly Ser Ser Leu Gly Pro
    675                 680                 685

Glu Tyr Asn Val Phe Ala Thr Gly Ser Gly Asp Cys Lys Ala Arg Ile
690                 695                 700

Trp Lys Tyr Lys Lys Ile Ala Pro Asn
705                 710

<210> SEQ ID NO 4
<211> LENGTH: 35
<212> TYPE: DNA
<213> ORGANISM: Candida albicans
<220> FEATURE:
<221> NAME/KEY: modified_base
<222> LOCATION: 18, 21, 33
<223> OTHER INFORMATION: N can be any nucleotide

<400> SEQUENCE: 4
ggggtaccyt tccadatnck ngcyttrcar tcncc                              35

<210> SEQ ID NO 5
<211> LENGTH: 9
<212> TYPE: PRT
<213> ORGANISM: Candida albicans

<400> SEQUENCE: 5

Gly Asp Cys Lys Ala Arg Ile Trp Lys
1               5

<210> SEQ ID NO 6
<211> LENGTH: 31
<212> TYPE: DNA
<213> ORGANISM: Candida albicans
<220> FEATURE:
<221> NAME/KEY: modified_base
<222> LOCATION: 21
<223> OTHER INFORMATION: N can be any nucleotide

<400> SEQUENCE: 6
ggctgcaggg ncaygarcar gayathtayt c                                  31

<210> SEQ ID NO 7
<211> LENGTH: 8
<212> TYPE: PRT
<213> ORGANISM: Candida albicans

<400> SEQUENCE: 7
```

```
Gly His Glu Gln Asp Ile Tyr Ser
1               5

<210> SEQ ID NO 8
<211> LENGTH: 30
<212> TYPE: DNA
<213> ORGANISM: Candida albicans

<400> SEQUENCE: 8
cgcggatccc caccagcaat gtccatgtat                                      30

<210> SEQ ID NO 9
<211> LENGTH: 29
<212> TYPE: DNA
<213> ORGANISM: Candida albicans

<400> SEQUENCE: 9
gcgggtaccg cgatgttgac gggtgctgt                                       29
```